United States Patent
Yamada et al.

(10) Patent No.: US 11,198,894 B2
(45) Date of Patent: Dec. 14, 2021

(54) METHOD OF PRODUCING AN L-AMINO ACID INVOLVING A CAROTENOID BIOSYNTHESIS ENZYME

(71) Applicant: AJINOMOTO CO., INC., Tokyo (JP)

(72) Inventors: Kazuteru Yamada, Kanagawa (JP); Ye Zhang, Kanagawa (JP); Kenji Abe, Kanagawa (JP); Naoki Iwanaga, Kanagawa (JP); Ryo Takeshita, Kanagawa (JP); Yuri Uehara, Kanagawa (JP); Chika Hikichi, Kanagawa (JP); Yasuhiro Oota, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 75 days.

(21) Appl. No.: 16/268,082

(22) Filed: Feb. 5, 2019

(65) Prior Publication Data

US 2019/0161780 A1 May 30, 2019

Related U.S. Application Data

(63) Continuation of application No. PCT/JP2017/029050, filed on Aug. 10, 2017.

(30) Foreign Application Priority Data

Aug. 10, 2016 (JP) .............................. JP2016-157800

(51) Int. Cl.
| | |
|---|---|
| *C12P 13/20* | (2006.01) |
| *C12P 13/08* | (2006.01) |
| *C12P 13/04* | (2006.01) |
| *C12N 15/09* | (2006.01) |
| *A23K 50/80* | (2016.01) |
| *A23K 10/18* | (2016.01) |
| *A01K 61/10* | (2017.01) |
| *A01K 61/59* | (2017.01) |
| *C12N 1/20* | (2006.01) |
| *C12P 13/14* | (2006.01) |

(52) U.S. Cl.
CPC .............. *C12P 13/08* (2013.01); *A01K 61/10* (2017.01); *A01K 61/59* (2017.01); *A23K 10/18* (2016.05); *A23K 50/80* (2016.05); *C12N 1/20* (2013.01); *C12N 15/09* (2013.01); *C12P 13/04* (2013.01); *C12P 13/14* (2013.01); *C12P 13/20* (2013.01)

(58) Field of Classification Search
None
See application file for complete search history.

(56) References Cited

U.S. PATENT DOCUMENTS

| | | | | |
|---|---|---|---|---|
| 5,811,273 | A  * | 9/1998 | Misawa | C12N 9/0004 |
| | | | | 435/148 |
| 6,087,152 | A | 7/2000 | Hohmann et al. | |
| 6,524,811 | B1 * | 2/2003 | Cunningham, Jr. | C12N 9/90 |
| | | | | 435/67 |
| 6,703,227 | B2 * | 3/2004 | Jakel | C08L 99/00 |
| | | | | 435/72 |
| 2004/0253663 | A1 | 12/2004 | Cheng et al. | |
| 2006/0031963 | A1 | 2/2006 | Schopfer et al. | |
| 2006/0194274 | A1 | 8/2006 | Flachmann et al. | |
| 2007/0015237 | A1 | 1/2007 | Bailey et al. | |
| 2009/0175911 | A1 | 7/2009 | Cutting et al. | |
| 2009/0221027 | A1 * | 9/2009 | Zelder | C12P 13/04 |
| | | | | 435/69.1 |
| 2010/0062496 | A1 | 3/2010 | Takikawa et al. | |
| 2010/0319077 | A1 | 12/2010 | Hirasawa et al. | |
| 2014/0170700 | A1 | 6/2014 | Umeno et al. | |

FOREIGN PATENT DOCUMENTS

| | | |
|---|---|---|
| JP | 9-23888 A | 1/1997 |
| JP | 2007-516697 A | 6/2007 |
| JP | 2008-537878 A | 10/2008 |
| JP | 2009-501547 A | 1/2009 |
| JP | 2009-521212 A | 6/2009 |
| JP | 5706056 B2 | 3/2015 |
| WO | WO03/101184 A2 | 12/2003 |
| WO | WO03/101184 A3 | 12/2003 |
| WO | WO2006/078039 A1 | 7/2006 |
| WO | WO2008/090770 A1 | 7/2008 |
| WO | WO2012/169623 A1 | 12/2012 |
| WO | WO2014/013489 A1 | 1/2014 |
| WO | WO2014/013489 A8 | 1/2014 |

OTHER PUBLICATIONS

International Search Report for PCT Patent App. No. PCT/JP2017/029050 (dated Nov. 7, 2017).
International Preliminary Report on Patentability for PCT Patent App. No. PCT/JP2017/029050 dated Feb. 12, 2019.
Frohwitter, J., et al., "Production of the sesquiterpene (+)-valencene by metabolically engineered *Corynebacterium glutamicum*," J. Biotechnol. 2014;191:205-213.
Extended European Search Report for European Patent App. No. 17839574.5 (dated Mar. 27, 2020).

* cited by examiner

*Primary Examiner* — Hope A Robinson
(74) *Attorney, Agent, or Firm* — Cermak Nakajima & McGowan LLP; Shelly Guest Cermak

(57) ABSTRACT

A method for producing an L-amino acid such as L-lysine is provided. An L-amino acid is produced by culturing a bacterium having an L-amino acid-producing ability, which has been modified so that the activity of a carotenoid biosynthesis enzyme is increased, in a medium, and collecting the L-amino acid from the medium.

11 Claims, 10 Drawing Sheets

Specification includes a Sequence Listing.

METHOD OF PRODUCING AN L-AMINO ACID INVOLVING A CAROTENOID BIOSYNTHESIS ENZYME This application is a Continuation of, and claims priority under 35 U.S.C. § 120 to, International Application No. PCT/JP2017/029050, filed Aug. 10, 2017, and claims priority therethrough under 35 U.S.C. § 119 to Japanese Patent Application No. 2016-157800, filed Aug. 10, 2016, the entireties of which are incorporated by reference herein. Also, the Sequence Listing filed electronically herewith is hereby incorporated by reference (File name: 2019-02-05T_US-589_Seq_List; File Size: 79 KB; Date recorded: Feb. 5, 2019).

BACKGROUND OF THE INVENTION

Field of the Invention

The present invention relates to a method for producing an L-amino acid such as L-lysine by fermentation using a bacterium. L-Amino acids are industrially useful as raw materials of seasonings, feed additives, and so forth.

Brief Description of the Related Art

L-Amino acids are industrially produced by, for example, fermentation using microorganisms such as bacteria having an L-amino acid-producing ability (Akashi, K. et al., Amino Acid Fermentation. Japan Scientific Societies Press, p. 195 to 215, 1986). Examples of such microorganisms, for example, can include strains isolated from the nature and mutant strains thereof. Also, the ability of the microorganisms to produce L-amino acid can be improved by using recombinant DNA techniques.

Carotenoids are compounds having a basic structure of $C_{40}H_{56}$ consisting of 8 isoprene units, and typically exhibit a color of orange, red, or the like. Carotenoids are biosynthesized by various organisms such as plants, algae, and bacteria. The relationship between the biosynthesis of carotenoids and production of L-amino acids has not been previously reported.

A method has been reported for producing fresh salmon having moderate red-orange colored by feeding salmon with a carotenoid during cultivation (JP patent No. 5706056).

SUMMARY OF THE INVENTION

It is an aspect of the present invention to develop a novel technique for improving the ability of a bacterium to produce an L-amino acid, and thereby provide a method for efficiently producing an L-amino acid.

It has been found that the ability of a bacterium to produce an L-amino acid can be improved by modifying the bacterium so that the expression of gene(s) encoding carotenoid biosynthesis enzyme(s) is increased.

It is an aspect of the present invention to provide a method for producing an L-amino acid, the method comprising culturing a bacterium having an L-amino acid-producing ability in a medium to accumulate an L-amino acid in the medium; and collecting the L-amino acid from the medium, wherein the bacterium has been modified so that the activity of a carotenoid biosynthesis enzyme is increased as compared with a non-modified bacterium.

It is a further aspect of the present invention to provide the method as described above, wherein the carotenoid biosynthesis enzyme is selected from the group consisting of geranylgeranyl pyrophosphate synthase, phytoene synthase, phytoene desaturase, lycopene beta-cyclase, carotene ketolase, carotene hydroxylase, and combinations thereof.

It is a further aspect of the present invention to provide the method as described above, wherein at least the activity or activities of one or more of said carotenoid biosynthesis enzymes is/are increased.

It is a further aspect of the present invention to provide the method as described above, wherein at least the activities of geranylgeranyl pyrophosphate synthase, phytoene synthase, phytoene desaturase, and lycopene beta-cyclase are increased.

It is a further aspect of the present invention to provide the method as described above, wherein the activity or activities of carotene ketolase and/or carotene hydroxylase is/are further increased.

It is a further aspect of the present invention to provide the method as described above, wherein the geranylgeranyl pyrophosphate synthase is a protein selected from the group consisting of: (a) a protein comprising the amino acid sequence of SEQ ID NO: 12 or 24; (b) a protein comprising the amino acid sequence of SEQ ID NO: 12 or 24, but which includes substitution, deletion, insertion, and/or addition of 1 to 10 amino acid residues, and having geranylgeranyl pyrophosphate synthase activity; and (c) a protein comprising an amino acid sequence having an identity of 90% or higher to the amino acid sequence of SEQ ID NO: 12 or 24, and having geranylgeranyl pyrophosphate synthase activity.

It is a further aspect of the present invention to provide the method as described above, wherein the phytoene synthase is a protein selected from the group consisting of: (a) a protein comprising the amino acid sequence of SEQ ID NO: 14 or 26; (b) a protein comprising the amino acid sequence of SEQ ID NO: 14 or 26, but which includes substitution, deletion, insertion, and/or addition of 1 to 10 amino acid residues, and having phytoene synthase activity; and (c) a protein comprising an amino acid sequence having an identity of 90% or higher to the amino acid sequence of SEQ ID NO: 14 or 26, and having phytoene synthase activity.

It is a further aspect of the present invention to provide the method as described above, wherein the phytoene desaturase is selected from the group consisting of: (a) a protein comprising the amino acid sequence of SEQ ID NO: 16 or 28; (b) a protein comprising the amino acid sequence of SEQ ID NO: 16 or 28, but which includes substitution, deletion, insertion, and/or addition of 1 to 10 amino acid residues, and having phytoene desaturase activity; and (c) a protein comprising an amino acid sequence having an identity of 90% or higher to the amino acid sequence of SEQ ID NO: 16 or 28, and having phytoene desaturase activity.

It is a further aspect of the present invention to provide the method as described above, wherein the lycopene beta-cyclase is a protein selected from the group consisting of: (a) a protein comprising the amino acid sequence of SEQ ID NO: 18; (b) a protein comprising the amino acid sequence of SEQ ID NO: 18, but which includes substitution, deletion, insertion, and/or addition of 1 to 10 amino acid residues, and having lycopene beta-cyclase activity; and (c) a protein comprising an amino acid sequence having an identity of 90% or higher to the amino acid sequence of SEQ ID NO: 18, and having lycopene beta-cyclase activity.

It is a further aspect of the present invention to provide the method as described above, wherein the carotene ketolase is a protein selected from the group consisting of: (a) a protein comprising the amino acid sequence of SEQ ID NO: 20, 30, or 61; (b) a protein comprising the amino acid sequence of SEQ ID NO: 20, 30, or 61, but which includes substitution, deletion, insertion, and/or addition of 1 to 10 amino acid residues, and having carotene ketolase activity; and (c) a protein comprising an amino acid sequence having an identity of 90% or higher to the amino acid sequence of SEQ ID NO: 20, 30, or 61, and having carotene ketolase activity.

The method mentioned above, wherein the carotene hydroxylase is a protein selected from the group consisting of: (a) a protein comprising the amino acid sequence of SEQ ID NO: 22, 58, 59, or 60; (b) a protein comprising the amino acid sequence of SEQ ID NO: 22, 58, 59, or 60, but which includes substitution, deletion, insertion, and/or addition of 1 to 10 amino acid residues, and having carotene hydroxylase activity; and (c) a protein comprising an amino acid sequence having an identity of 90% or higher to the amino acid sequence of SEQ ID NO: 22, 58, 59, or 60, and having carotene hydroxylase activity.

It is a further aspect of the present invention to provide the method as described above, wherein the activity of the carotenoid biosynthesis enzyme is increased by increasing the expression of a gene encoding the carotenoid biosynthesis enzyme.

It is a further aspect of the present invention to provide the method as described above, wherein the expression of the gene is increased by increasing the copy number of the gene and/or modifying an expression control sequence of the gene.

It is a further aspect of the present invention to provide the method as described above, wherein the bacterium is a bacterium belonging to the family Enterobacteriaceae or a coryneform bacterium.

It is a further aspect of the present invention to provide the method as described above, wherein the bacterium is a bacterium belonging to the genus *Pantoea* or *Escherichia*.

It is a further aspect of the present invention to provide the method as described above, wherein the bacterium is *Pantoea ananatis* or *Escherichia coli*.

It is a further aspect of the present invention to provide the method as described above, wherein the bacterium is a bacterium belonging to the genus *Corynebacterium*.

It is a further aspect of the present invention to provide the method as described above, wherein the bacterium is *Corynebacterium glutamicum*.

It is a further aspect of the present invention to provide the method as described above, wherein the L-amino acid is an L-amino acid of the aspartate family and/or an L-amino acid of the glutamate family.

It is a further aspect of the present invention to provide the method as described above, wherein the L-amino acid is selected from the group consisting of L-lysine, L-threonine, L-glutamic acid, and combinations thereof.

It is a further aspect of the present invention to provide the method as described above, wherein the bacterium is able to produce a carotenoid, and said carotenoid accumulates in cells of the bacterium as a result of the culturing.

It is a further aspect of the present invention to provide the method as described above, wherein the cells contain the carotenoid in an amount of 10 µg/g-DCW or more.

It is a further aspect of the present invention to provide the method as described above, wherein the carotenoid selected from the group consisting of beta-carotene, zeaxanthin, canthaxanthin, astaxanthine, and combinations thereof.

It is a further aspect of the present invention to provide the method as described above, which further comprises collecting cells of the bacterium.

It is a further aspect of the present invention to provide a method for producing bacterial cells containing a carotenoid, the method comprising culturing a bacterium that is able to produce an L-amino acid and a carotenoid in a medium to accumulate a carotenoid in cells of the bacterium; and collecting the cells, wherein the bacterium has been modified so that the activity of a carotenoid biosynthesis enzyme is increased as compared with a non-modified bacterium.

It is a further aspect of the present invention to provide the method as described above, wherein the cells contain the carotenoid in an amount of 10 µg/g-DCW or more.

It is a further aspect of the present invention to provide the method as described above, wherein the carotenoid is selected from the group consisting of beta-carotene, zeaxanthin, canthaxanthin, astaxanthine, and combinations thereof.

Cells of a bacterium, wherein the cells contain a carotenoid, wherein the bacterium is able to produce an L-amino acid and a carotenoid, and wherein the bacterium has been modified so that the activity of a carotenoid biosynthesis enzyme is increased as compared with a non-modified bacterium.

It is a further aspect of the present invention to provide the cells as described above, wherein the cells contain the carotenoid in an amount of 10 µg/g-DCW or more.

It is a further aspect of the present invention to provide the cells as described above, wherein the carotenoid is selected from the group consisting of beta-carotene, zeaxanthin, canthaxanthin, astaxanthine, and combinations thereof.

It is a further aspect of the present invention to provide a composition for culturing an aquatic organism, the composition containing the cells mentioned above, wherein the aquatic organism is salmon, shrimp, or seabream.

It is a further aspect of the present invention to provide a feed for an aquatic organism, the feed containing the cells as described above, wherein the aquatic organism is salmon, shrimp, or seabream.

It is a further aspect of the present invention to provide a method for culturing an aquatic organism, the method comprising feeding cells produced by the method as described above, the cells mentioned above, the composition mentioned above, or the feed mentioned above to an aquatic organism, wherein the aquatic organism is salmon, shrimp, or seabream.

Control, WC196LC;
crtZ(Pa), WC196LC_crtEYIB(ML)_ΔyhfK::P4071_crtZ(Pa);
crtZ(Br), WC196LC_crtEYIB(ML)_ΔyhfK::P4071_crtZ(Br);
crtZ(Pc), WC196LC_crtEYIB(ML)_ΔyhfK::P4071_crtZ(Pc);
crtZ(Al), WC196LC_crtEYIB(ML)_ΔyhfK::P4071_crtZ(Al).

Figure 3:
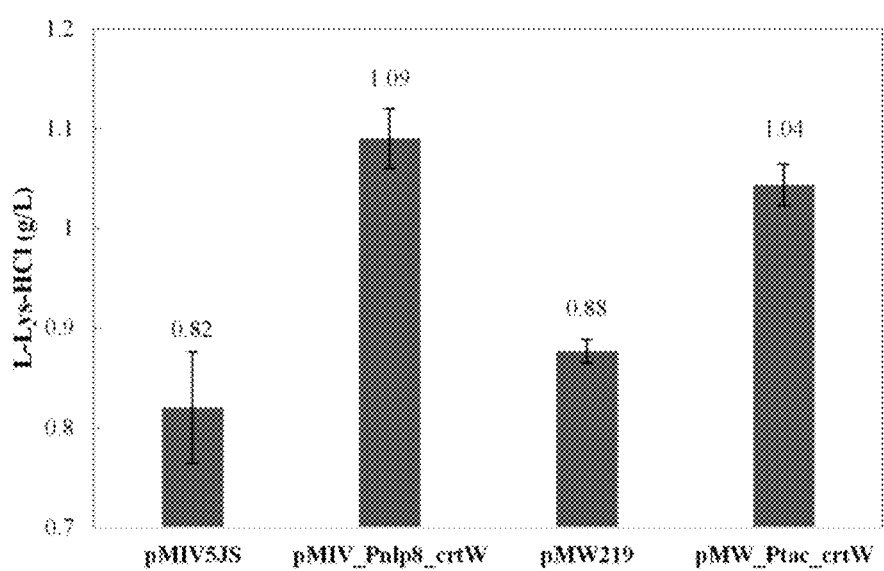

FIG. 3 shows a graph of the results of L-lysine production culture using *E. coli* strains having an enhanced expression of carotenoid biosynthesis enzyme genes (crtEYIB, crtZ, and crtW) (n=3):

pMIV5JS, WC196LC/pMIV5JS;
pMIV_Pnlp8_crtW, WC196LC_crtEYIB(ML)_ΔyhfK::P4071_crtZ(Pa)/pMIV-Pnlp8-crtW;
pMW219, WC196LC/pMW219;
pMW_Ptac_crtW, WC196LC_crtEYIB(ML)_ΔyhfK::P4071_crtZ(Pa)/pMW_Ptac_crtW.

Figure 4:
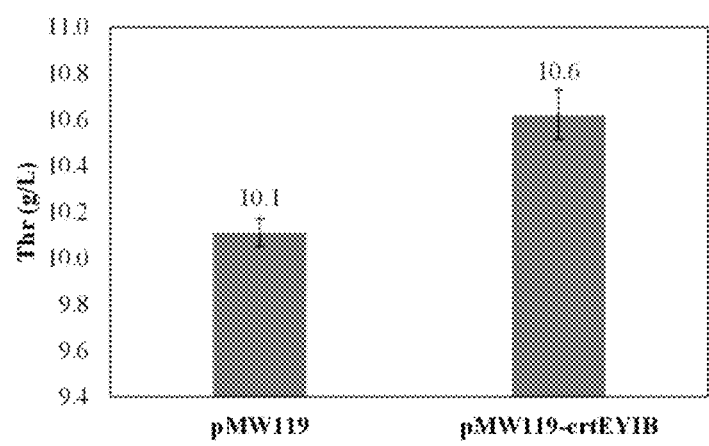

FIG. 4 shows a graph of the results of L-threonine production culture using an *E. coli* strain having an enhanced expression of carotenoid biosynthesis enzyme genes (crtEYIB):
pMW119, VKPM B-3996/pMW119 (n=4);
pMW119-crtEYIB, VKPM B-3996/pMW119-crtEYIB (n=10).

Figure 5:
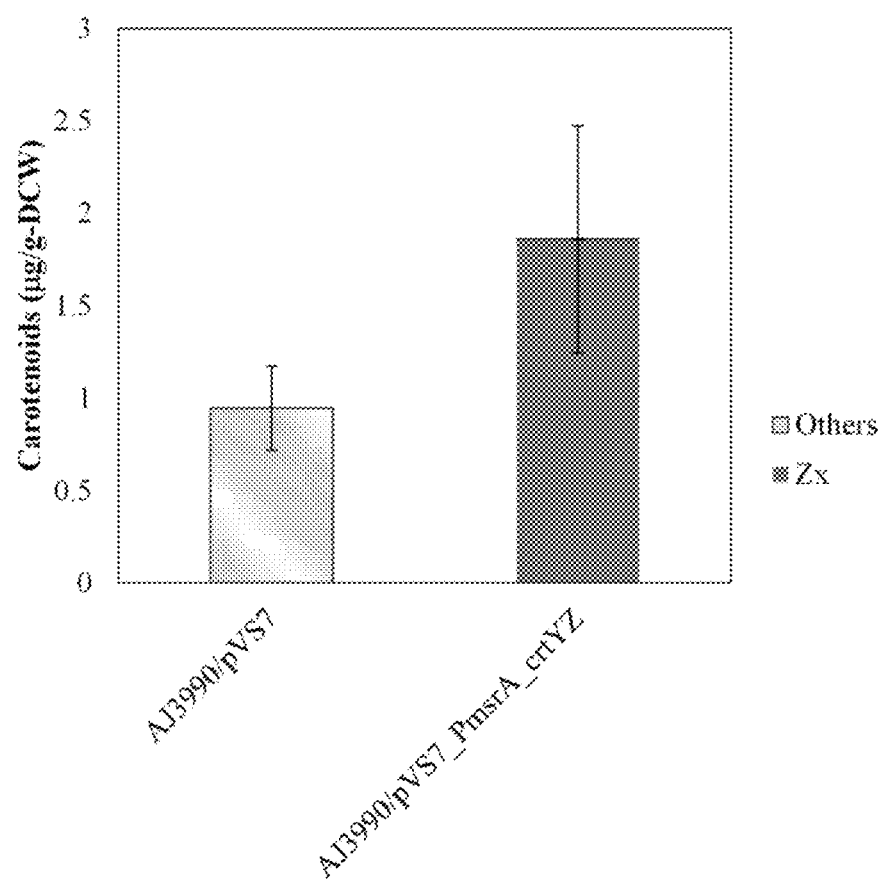

FIG. 5 shows a graph of the quantification results of carotenoids in a *C. glutamicum* strain having an enhanced expression of carotenoid biosynthesis enzyme genes (crtY and crtZ) (n=3). The concentrations of substances corresponding to peaks detected by HPLC other than zeaxanthin (Zx) were estimated on the basis of the peak area of a Zx standard solution, and the sum total of them was indicated as "Others".

Figure 6:
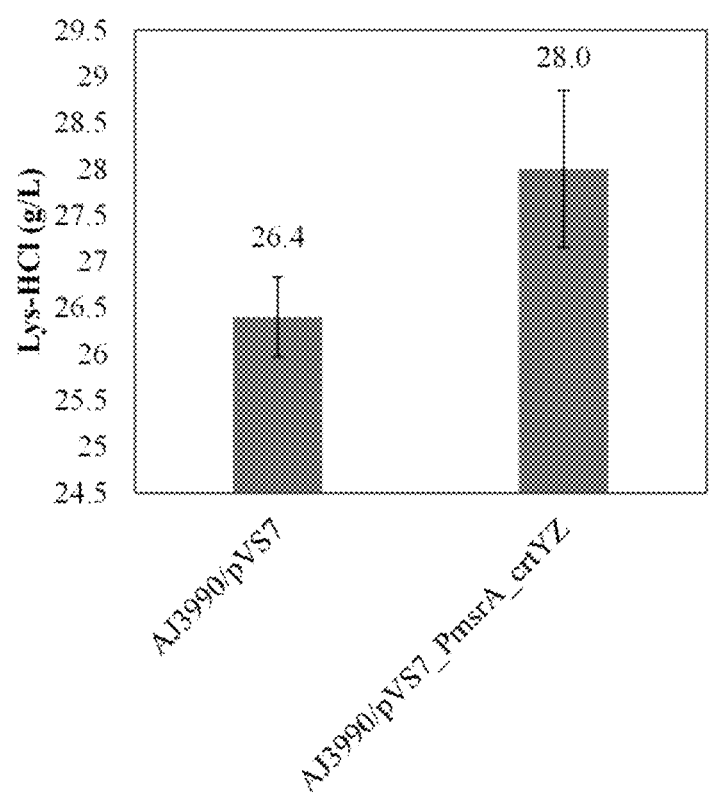

FIG. 6 shows graph of the results of L-lysine production culture using a *C. glutamicum* strain having an enhanced expression of carotenoid biosynthesis enzyme genes (crtY and crtZ) (n=4).

Figure 7:
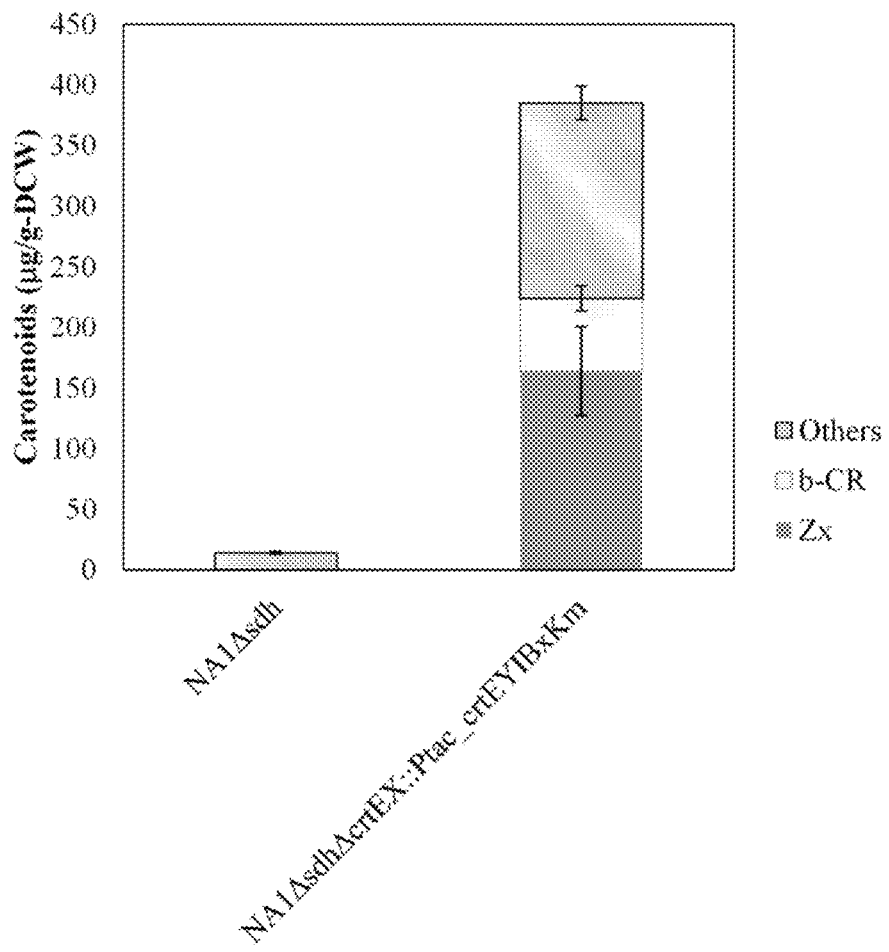

FIG. 7 shows a graph of the quantification results of carotenoids in a *P. ananatis* strain having an enhanced expression of a carotenoid biosynthesis enzyme gene (crtE) (n=3). Standard solutions of astaxanthin (Ax), canthaxanthin (Cx), zeaxanthin (Zx), and beta-carotene (b-CR) were used for HPLC, and the concentrations of these substances were calculated on the basis of the respective peak areas. The concentrations of substances corresponding to detected peaks other than these substances were estimated on the basis of the peak area of the Ax standard solution, and the sum total of them was indicated as "Others".

Figure 8:
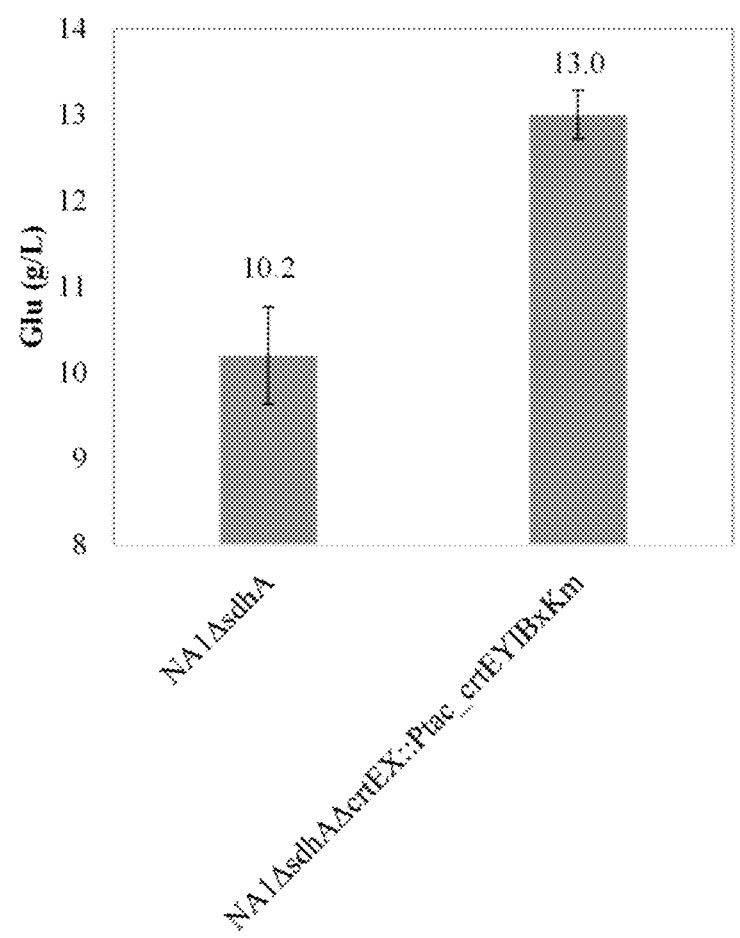

FIG. 8 shows a graph of the results of L-glutamic acid production culture using a *P. ananatis* strain having an enhanced expression of a carotenoid biosynthesis enzyme gene (crtE).

Figure 9:
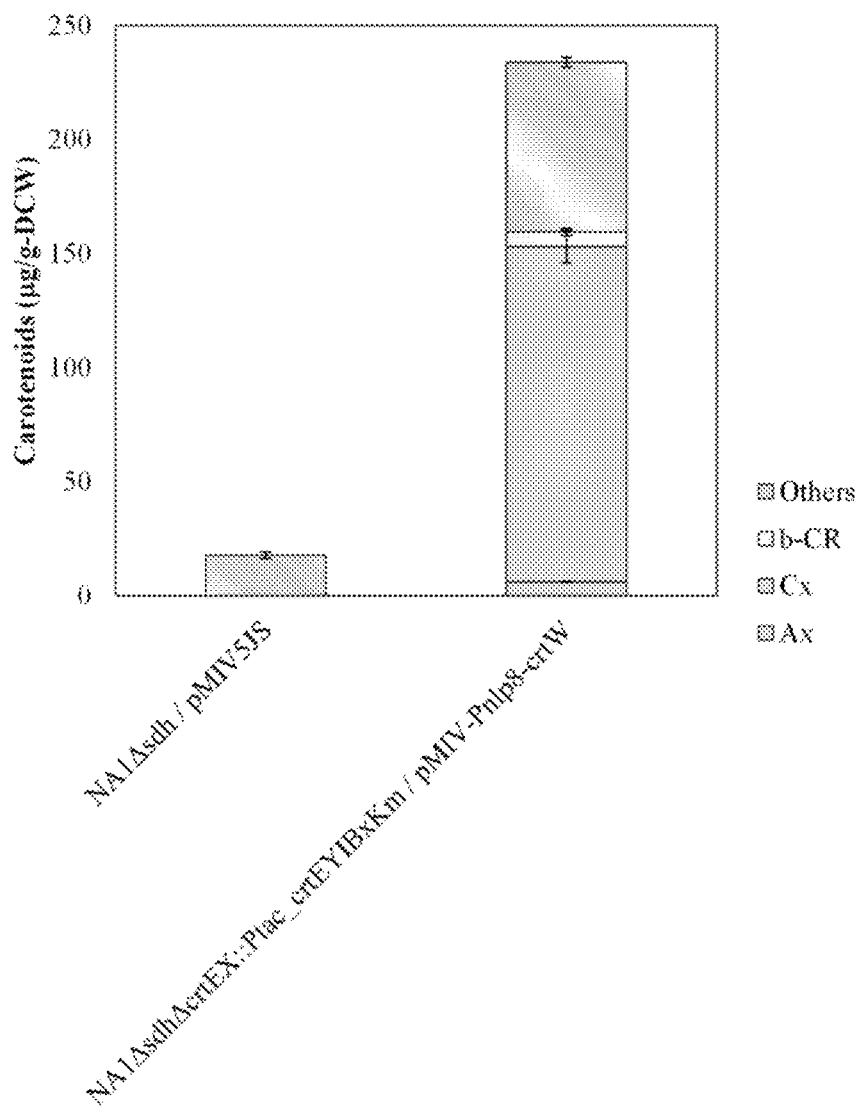

FIG. 9 shows a graph of the quantification results of carotenoids in a *P. ananatis* strain having an enhanced expression of carotenoid biosynthesis enzyme genes (crtE and crtW) (n=3). Standard solutions of astaxanthin (Ax), canthaxanthin (Cx), zeaxanthin (Zx), and beta-carotene (b-CR) were used for HPLC, and the concentrations of these substances were calculated on the basis of the respective peak areas. The concentrations of substances corresponding to detected peaks other than these substances were estimated on the basis of the peak area of the Ax standard solution, and the sum total of them was indicated as "Others".

Figure 10:
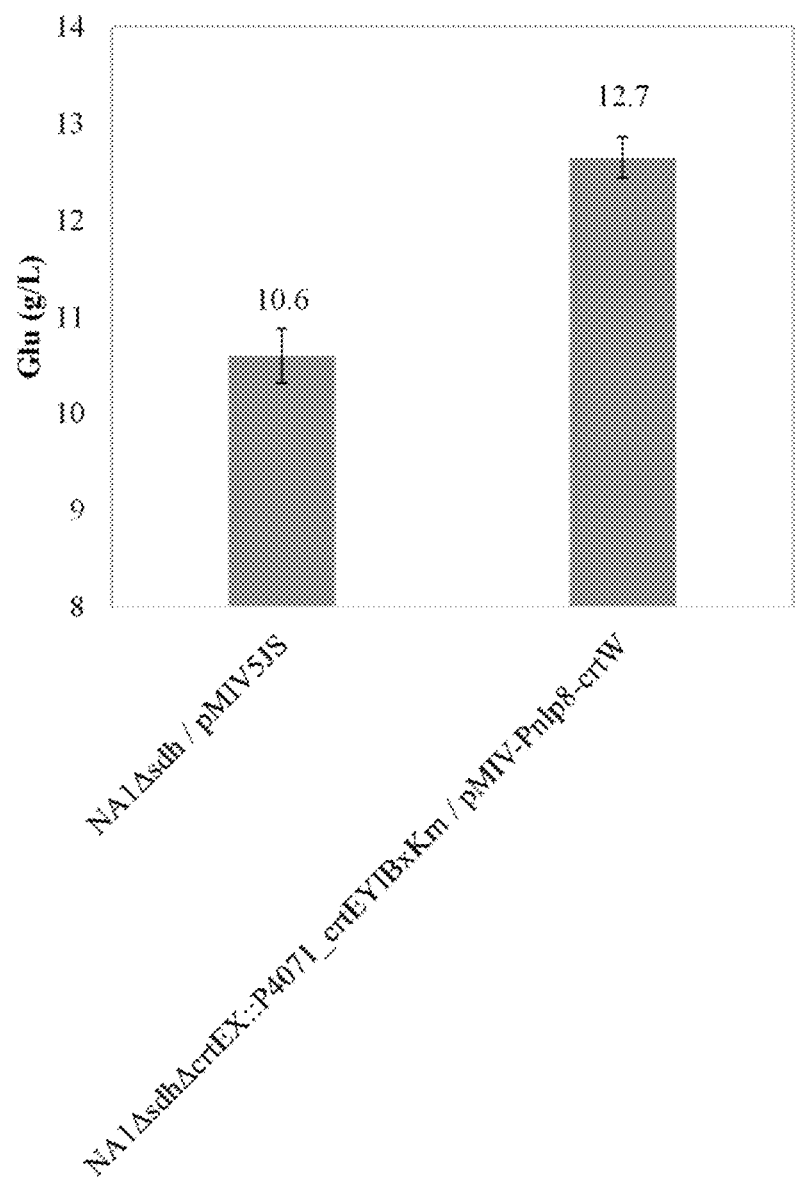

FIG. 10 shows a graph of the results of L-glutamic acid production culture using a *P. ananatis* strain having an enhanced expression of carotenoid biosynthesis enzyme genes (crtE and crtW).

DETAILED DESCRIPTION OF EXEMPLARY EMBODIMENTS

<1> Bacterium

The bacterium as described herein is a bacterium having an ability to produce an L-amino acid, which has been modified so that the activity of a carotenoid biosynthesis enzyme is increased.

<1-1> Bacterium Having an Ability to Produce an L-Amino Acid

The phrase "bacterium having an ability to produce an L-amino acid" can refer to a bacterium having an ability to generate and accumulate an objective L-amino acid in a medium to such a degree that the L-amino acid can be collected, when the bacterium is cultured in the medium. The bacterium having an ability to produce an L-amino acid may be a bacterium that is able to accumulate an objective L-amino acid in a medium in an amount larger than that obtainable with a non-modified strain of the bacterium. The term "non-modified strain of the bacterium" can refer to a control strain that has not been modified so that the activity of a carotenoid biosynthesis enzyme is increased. That is, examples of the non-modified strain of the bacterium can include a wild-type strain and parental strain. The bacterium having an ability to produce an L-amino acid may be a bacterium that is able to accumulate an objective L-amino acid in a medium in an amount of 0.5 g/L or more, or 1.0 g/L or more.

Examples of the L-amino acid can include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. Particular examples of the L-amino acid can include L-amino acids of the glutamate family and L-amino acids of the aspartate family. The term "L-amino acids of glutamate family" collectively can refer to L-glutamic acid and L-amino acids that are biosynthesized via L-glutamic acid as an intermediate. Examples of the L-amino acids that are biosynthesized via L-glutamic acid as an intermediate can include L-glutamine, L-proline, L-arginine, L-citrulline, and L-ornithine. The term "L-amino acids of aspartate family" collectively can refer to L-aspartic acid and L-amino acids that are biosynthesized via L-aspartic acid as an intermediate. Examples of the L-amino acids that are biosynthesized via L-aspartic acid as an intermediate include L-lysine, L-threonine, L-isoleucine, and L-methionine. More particular examples of the L-amino acid include L-lysine, L-threonine, and L-glutamic acid. The bacterium may have an ability to produce a single kind of L-amino acid, or two or more kinds of L-amino acids.

The term "amino acid" can refer to an L-amino acid, unless otherwise stated. The term "L-amino acid" can refer to an L-amino acid in a free form, a salt thereof, or a mixture thereof, unless otherwise stated. Examples of salt will be described later.

Examples of the bacterium can include bacteria belonging to the family Enterobacteriaceae and coryneform bacteria.

Examples of bacteria belonging to the family Enterobacteriaceae can include bacteria belonging to the genus *Escherichia, Enterobacter, Pantoea, Klebsiella, Serratia, Erwnia, Photorhabdus, Providencia, Salmonella, Morganella*, or the like. Specifically, bacteria classified into the family Enterobacteriaceae according to the taxonomy used in the NCBI (National Center for Biotechnology Information database ncbi.nlm.nih.gov/Taxonomy/Browser/wwwtax.cgi?id=91347) can be used.

The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* can include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof.

The *Enterobacter* bacteria are not particularly limited, and examples can include those classified into the genus *Enterobacter* according to the taxonomy known to those skilled in the field of microbiology. Examples of the *Enterobacter* bacterium can include, for example, *Enterobacter agglomerans* and *Enterobacter aerogenes*. Specific examples of *Enterobacter agglomerans* can include, for example, the *Enterobacter agglomerans* ATCC 12287 strain. Specific examples of *Enterobacter aerogenes* can include, for example, the *Enterobacter aerogenes* ATCC 13048 strain, NBRC 12010 strain (Biotechnol. Bioeng., 2007, Mar. 27; 98(2):340-348), and AJ110637 strain (FERM BP-10955). Examples of the *Enterobacter* bacteria also can include, for example, the strains described in European Patent Application Laid-open (EP-A) No. 0952221. In addition, *Enterobacter agglomerans* also can include some strains classified as *Pantoea agglomerans*.

The *Pantoea* bacteria are not particularly limited, and examples can include those classified into the genus *Pantoea* according to the taxonomy known to those skilled in the field of microbiology. Examples of the *Pantoea* bacteria can include, for example, *Pantoea ananatis, Pantoea stewartii, Pantoea agglomerans*, and *Pantoea citrea*. Specific examples of *Pantoea ananatis* can include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some of *Enterobacter* bacteria and *Erwinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Int. J. Syst. Bacteriol., 39, 337-345 (1989)). The *Pantoea* bacteria can include those reclassified into the genus *Pantoea* as described above.

Examples of the *Erwinia* bacteria can include *Erwinia amylovora* and *Erwinia carotovora*. Examples of the *Klebsiella* bacteria can include *Klebsiella planticola*.

Examples of the coryneform bacteria can include bacteria belonging to the genus *Corynebacterium, Brevibacterium, Microbacterium*, or the like.

Specific examples of the coryneform bacteria can include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes (Corynebacterium efficiens)*
*Corynebacterium herculis*
*Brevibacterium divaricatum (Corynebacterium glutamicum)*
*Brevibacterium flavum (Corynebacterium glutamicum)*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Corynebacterium ammoniagenes (Corynebacterium stationis)*
*Brevibacterium album*
*Brevibacterium cerinum*
*Microbacterium ammoniaphilum*

Specific examples of the coryneform bacteria can include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens (Corynebacterium thermoaminogenes)* AJ12340 (FERM BP-1539)
*Corynebacterium herculis* ATCC 13868
*Brevibacterium divaricatum (Corynebacterium glutamicum)* ATCC 14020
*Brevibacterium flavum (Corynebacterium glutamicum)* ATCC 13826, ATCC 14067, AJ12418 (FERM BP-2205)
*Brevibacterium immariophilum* ATCC 14068
*Brevibacterium lactofermentum (Corynebacterium glutamicum)* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes (Corynebacterium stationis)* ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria that had previously been classified into the genus *Brevibacterium*, but are presently united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

The bacterium can inherently have the ability to produce an L-amino acid, or may be a bacterium that is modified to have such an ability. The bacterium having the ability to produce an L-amino acid can be obtained by imparting an ability to such a bacterium as mentioned above, or by enhancing an ability of such a bacterium as mentioned above.

To impart or enhance the ability to produce an L-amino acid, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods can include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a usual mutagenesis treatment, and then selecting a strain exhibiting autotrophy, analogue resistance, or a metabolic regulation mutation, and having an L-amino acid-producing ability from the obtained mutant strains. Examples of the usual mutagenesis treatment can include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An ability to produce an L-amino acid can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP1010755A, and so forth. The detailed procedures for enhancing enzyme activity will be described herein.

Furthermore, an ability to produce an L-amino acid can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" can include an enzyme involved in decomposition of the objective amino acid. The method for reducing an enzyme activity will be described herein.

Hereinafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability can include, for example, a method of modifying a bacterium so that the bacterium has an increased activity or activities of one or more of the L-glutamic acid biosynthesis enzymes. Examples of such enzymes can include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (OA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are the name of the genes encoding the enzymes (the same shall apply similarly hereinafter). The activity or activities of one or more of, for example, glutamate dehydrogenase, citrate synthase, phosphoenol pyruvate carboxylase, and methylcitrate synthase, can be enhanced.

Examples of strains belonging to the family Enterobacteriaceae and modified so that the expression of the citrate synthase gene, phosphoenolpyruvate carboxylase gene, and/or glutamate dehydrogenase gene are increased can include those disclosed in EP1078989A, EP955368A, and EP952221A. Furthermore, examples of strains belonging to the family Enterobacteriaceae and modified so that the expression of a gene of the Entner-Doudoroff pathway (edd, eda) is increased can include those disclosed in EP1352966B. Examples of coryneform bacteria modified so that the expression of the glutamate synthetase gene (gltBD) is increased can include those disclosed in WO99/07853.

Examples of methods for imparting or enhancing L-glutamic acid-producing ability also can include, for example, a method of modifying a bacterium so that the bacterium has a reduced activity or activities of one or more of the enzymes that catalyze a reaction branching away from the biosynthesis pathway of L-glutamic acid to generate a compound other than L-glutamic acid. Examples of such enzymes can include, but are not particularly limited to, isocitrate lyase (aceA), α-ketoglutarate dehydrogenase (sucA, odhA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). The activity of, for example, α-ketoglutarate dehydrogenase, can be reduced or deleted.

*Escherichia* bacteria having a reduced α-ketoglutarate dehydrogenase activity or deficient in the α-ketoglutarate dehydrogenase activity, and methods for obtaining such bacteria are described in U.S. Pat. Nos. 5,378,616 and 5,573,945. Furthermore, methods for reducing or deleting the α-ketoglutarate dehydrogenase activity of Enterobacteriaceae bacteria such as *Pantoea* bacteria, *Enterobacter* bacteria, *Klebsiella* bacteria, and *Erwinia* bacteria are disclosed in U.S. Pat. Nos. 6,197,559, 6,682,912, 6,331,419, and 8,129,151, and WO2008/075483. Specific examples of *Escherichia* bacteria having a reduced α-ketoglutarate dehydrogenase activity or deficient in the α-ketoglutarate dehydrogenase activity can include the following strains:

E. coli W3110sucA::Km$^r$
E. coli AJ12624 (FERM BP-3853)
E. coli AJ12628 (FERM BP-3854)
E. coli AJ12949 (FERM BP-4881)
E. coli W3110sucA::Km$^r$ is a strain obtained by disrupting the sucA gene encoding α-ketoglutarate dehydrogenase of E. coli W3110. This strain is completely deficient in the α-ketoglutarate dehydrogenase activity.

Coryneform bacteria in which the α-ketoglutarate dehydrogenase activity is reduced or eliminated, and methods for obtaining those are disclosed in WO2008/075483. Specific examples of coryneform bacteria in which the α-ketoglutarate dehydrogenase activity is reduced or eliminated can include, for example, the following strains:

Corynebacterium glutamicum (Brevibacterium lactofermentum) L30-2 strain (Japanese Patent Laid-open (Kokai) No. 2006-340603)
Corynebacterium glutamicum (Brevibacterium lactofermentum) ΔS strain (WO95/34672)
Corynebacterium glutamicum (Brevibacterium lactofermentum) AJ12821 (FERM BP-4172, French Patent No. 9401748)
Corynebacterium glutamicum (Brevibacterium flavum) AJ12822 (FERM BP-4173, French Patent No. 9401748)
Corynebacterium glutamicum AJ12823 (FERM BP-4174, French Patent No. 9401748)

Examples of L-glutamic acid-producing bacteria and parental strains that can be used to derive such bacteria also can include Pantoea bacteria, such as the Pantoea ananatis AJ13355 strain (FERM BP-6614), Pantoea ananatis SC17 strain (FERM BP-11091), and Pantoea ananatis SC17(0) strain (VKPM B-9246). AJ13355 is a strain isolated from soil in Iwata-shi, Shizuoka-ken, Japan as a strain that can proliferate in a low pH medium containing L-glutamic acid and a carbon source. The SC17 strain was selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depository (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Furthermore, examples of L-glutamic acid-producing bacteria and parental strains that can be used to derive such bacteria also can include Pantoea bacteria having a reduced α-ketoglutarate dehydrogenase activity or deficient in the α-ketoglutarate dehydrogenase activity. Examples of such strains can include the AJ13356 strain (U.S. Pat. No. 6,331, 419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, under an accession number of FERM BP-8646.

The AJ13355 strain was identified as Enterobacter agglomerans when it was isolated, but it was recently reclassified as Pantoea ananatis on the basis of nucleotide sequencing of 16S rRNA and so forth. Therefore, although the AJ13355 and AJ13356 strains are deposited at the aforementioned depository as Enterobacter agglomerans, they are referred to as Pantoea ananatis in this specification.

Furthermore, examples of L-glutamic acid-producing bacteria and parental strains that can be used to derive such bacteria also can include Pantoea bacteria such as the Pantoea ananatis SC17sucA/RSFCPG+pSTVCB strain, Pantoea ananatis AJ13601 strain, Pantoea ananatis NP106 strain, and Pantoea ananatis NA1 strain. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from Escherichia coli, and the plasmid pSTVCB containing the citrate synthase gene (gltA) derived from Brevibacterium lactofermentum, into the SC17sucA strain. The AJ13601 strain was selected from the SC17sucA/RSFCPG+pSTVCB strain as a strain resistant to a high concentration of L-glutamic acid at a low pH. The NP106 strain was obtained from the AJ13601 strain by curing the RSFCPG and pSTVCB plasmids. The NA1 strain was obtained from the NP106 strain by introducing the plasmid RSFPPG thereinto (WO2010/027045). The plasmid RSFPPG has a structure corresponding to the plasmid RSFCPG except that gltA gene thereof has been replaced with a methylcitrate synthase gene (prpC), and hence, contains prpC gene, ppc gene, and gdhA gene (WO2008/020654). The AJ13601 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parental strains that can be used to derive such bacteria also can include strains in which both the α-ketoglutarate dehydrogenase (sucA) activity and the succinate dehydrogenase (sdh) activity are reduced or deleted (Japanese Patent Laid-open (Kokai) No. 2010-041920). Specific examples of such strains can include, for example, a sucAsdhA double-deficient strain of the *Pantoea ananatis* NA1 strain and an odhAsdhA double-deficient strain of the *Corynebacterium glutamicum* ATCC 14067 strain, i.e. the *Corynebacterium glutamicum* 8L3GΔSDH strain (Japanese Patent Laid-open (Kokai) No. 2010-041920).

Examples of L-glutamic acid-producing bacteria and parental strains that can be used to derive such bacteria also can include auxotrophic mutant strains. Specific examples of auxotrophic mutant strains can include, for example, *E. coli* VL334thrC⁺ (VKPM B-8961, EP1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC⁺ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parental strains that can be used to derive such bacteria also can include strains having resistance to an aspartic acid analogue. Such strains can also be deficient in the α-ketoglutarate dehydrogenase activity. Specific examples of strains having resistance to an aspartic acid analogue and deficient in the α-ketoglutarate dehydrogenase activity can include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* AJ13138 (FERM BP-5565, U.S. Pat. No. 6,110,714).

Examples of methods for imparting or enhancing L-glutamic acid-producing ability also can include, for example, a method of enhancing the expression of an L-glutamic acid secretion gene, such as yhfK gene (WO2005/085419) or ybjL gene (WO2008/133161).

Furthermore, examples of methods for imparting or enhancing L-glutamic acid-producing ability to or in coryneform bacteria also can include methods of imparting resistance to an organic acid analogue, respiratory inhibitor, or the like, and methods of imparting sensitivity to a cell wall synthesis inhibitor. Specific examples of such methods can include, for example, the method of imparting monofluoroacetic acid resistance (Japanese Patent Laid-open (Kokai) No. 50-113209), the method of imparting adenine resistance or thymine resistance (Japanese Patent Laid-open (Kokai) No. 57-065198), the method of attenuating urease (Japanese Patent Laid-open (Kokai) No. 52-038088), the method of imparting malonic acid resistance (Japanese Patent Laid-open (Kokai) No. 52-038088), the method of imparting resistance to benzopyrones or naphthoquinones (Japanese Patent Laid-open (Kokai) No. 56-1889), the method of imparting HOQNO resistance (Japanese Patent Laid-open (Kokai) No. 56-140895), the method of imparting α-ketomalonic acid resistance (Japanese Patent Laid-open (Kokai) No. 57-2689), the method of imparting guanidine resistance (Japanese Patent Laid-open (Kokai) No. 56-35981), the method of imparting sensitivity to penicillin (Japanese Patent Laid-open (Kokai) No. 4-88994), and so forth.

Specific examples of such resistant or sensitive bacteria can include the following strains:

*Corynebacterium glutamicum* (*Brevibacterium flavum*) AJ3949 (FERM BP-2632, Japanese Patent Laid-open (Kokai) No. 50-113209)

*Corynebacterium glutamicum* AJ11628 (FERM P-5736, Japanese Patent Laid-open (Kokai) No. 57-065198)

*Corynebacterium glutamicum* (*Brevibacterium flavum*) AJ11355 (FERM P-5007, Japanese Patent Laid-open (Kokai) No. 56-1889)

*Corynebacterium glutamicum* AJ11368 (FERM P-5020, Japanese Patent Laid-open (Kokai) No. 56-1889)

*Corynebacterium glutamicum* (*Brevibacterium flavum*) AJ11217 (FERM P-4318, Japanese Patent Laid-open (Kokai) No. 57-2689)

*Corynebacterium glutamicum* AJ11218 (FERM P-4319, Japanese Patent Laid-open (Kokai) No. 57-2689)

*Corynebacterium glutamicum* (*Brevibacterium flavum*) AJ11564 (FERM BP-5472, Japanese Patent Laid-open (Kokai) No. 56-140895)

*Corynebacterium glutamicum* (*Brevibacterium flavum*) AJ11439 (FERM BP-5136, Japanese Patent Laid-open (Kokai) No. 56-35981)

*Corynebacterium glutamicum* H7684 (FERM BP-3004, Japanese Patent Laid-open (Kokai) No. 04-88994)

*Corynebacterium glutamicum* (*Brevibacterium lactofermentum*) AJ11426 (FERM P-5123, Japanese Patent Laid-open (Kokai) No. 56-048890)

*Corynebacterium glutamicum* AJ11440 (FERM P-5137, Japanese Patent Laid-open (Kokai) No. 56-048890)

*Corynebacterium glutamicum* (*Brevibacterium lactofermentum*) AJ11796 (FERM P-6402, Japanese Patent Laid-open (Kokai) No. 58-158192)

Furthermore, examples of methods for imparting or enhancing L-glutamic acid-producing ability to or in coryneform bacteria also can include a method of enhancing the expression of yggB gene and a method of introducing a mutant yggB gene having a mutation in the coding region (WO2006/070944). That is, the bacterium may have been modified so that the expression of yggB gene is increased, or may have been modified so as to harbor (have) a mutant yggB gene.

The yggB gene is a gene encoding a mechanosensitive channel. Examples of the yggB gene can include yggB genes of coryneform bacteria. Specific examples of the yggB genes of coryneform bacteria can include, for example, yggB genes of *Corynebacterium glutamicum* ATCC13869, *Corynebacterium glutamicum* ATCC13032, *Corynebacterium glutamicum* ATCC14967, and *Corynebacterium melassecola* ATCC17965 (WO2006/070944). The yggB gene of *Corynebacterium glutamicum* ATCC 13032 corresponds to the sequence complementary to the sequence of the nucleotide numbers 1,336,091 to 1,337,692 in the genome sequence registered as Genbank Accession No. NC_003450 in the NCBI database, and is also called NCgl1221. The YggB protein encoded by the yggB gene of *Corynebacterium glutamicum* ATCC 13032 is registered as GenBank accession No. NP_600492. In addition, the nucleotide sequence of the yggB gene of *Corynebacterium glutamicum* 2256 (ATCC 13869) and the amino acid sequence of the YggB protein encoded by the gene are shown in SEQ ID NOS: 7 and 8, respectively.

A yggB gene having the "specific mutation" described herein can also be referred to as "mutant yggB gene", and a protein encoded thereby can also be referred to as "mutant YggB protein". Furthermore, a yggB gene not having the "specific mutation" described herein can also be referred to as "wild-type yggB gene", and a protein encoded thereby can also be referred to as "wild-type YggB protein". Incidentally, as for the YggB protein, a change of the amino acid sequence caused by the "specific mutation" in the yggB gene can also be referred to as "specific mutation". The term "wild-type" is used for convenience to distinguish the "wild-type" yggB gene or YggB protein from the "mutant" yggB gene or YggB protein, and the "wild-type" yggB gene or YggB protein is not limited to those obtained as natural substances, so long as it does not have the "specific mutation". Examples of the wild-type YggB protein can include the YggB proteins exemplified above, such as YggB protein having the amino acid sequence of SEQ ID NO: 8. Examples of the wild-type YggB protein also can include conservative variants (variants in which the original function thereof is maintained) of the YggB proteins exemplified above, provided that the conservative variants do not have the "specific mutation". The "original function" regarding the YggB protein may be, for example, a function as a mechanosensitive channel or a property that an increased expression thereof in a coryneform bacterium provides an improved L-glutamic acid-producing ability of the coryneform bacterium.

The "specific mutation" is not particularly limited, so long as it changes the amino acid sequence of the YggB protein such as those described above to thereby improve an L-glutamic acid-producing ability of a coryneform bacterium. Examples of the "specific mutation" can include mutation on the C-terminus side and mutation in a transmembrane region (WO2006/070944). The "specific mutation" may also be a combination of these.

(1) Mutation on C-Terminus Side

The mutation on the C-terminus side is a mutation introduced into the region of the wild-type yggB gene coding for the amino acid residues of the positions 419 to 533 of the wild-type YggB protein. The mutation on the C-terminus side may be introduced at one or more sites in the region. The type of change of the amino acid sequence induced by the mutation on the C-terminus side is not particularly limited. The mutation on the C-terminus side may be a mutation causing amino acid substitution (missense mutation), insertion of amino acid residue, deletion of amino acid residue, introduction of stop codon (nonsense mutation), frame shift mutation, or a combination of these. The mutation on the C-terminus side can be, for example, a mutation for inserting a nucleotide sequence such as an insertion sequence (henceforth also referred to as "IS") or transposon.

(1-1) Insertion of Nucleotide Sequence

Examples of the mutation on the C-terminus side can include, for example, a mutation that inserts a nucleotide sequence at the site coding for the valine residue at the position 419 of the wild-type YggB protein (2A-1 type mutation). The 2A-1 type mutation may be, for example, a mutation that causes deletion or substitution for a part or all of the amino acid residues of the positions 419 to 533 of the wild-type YggB protein. Specific examples of the mutant yggB gene having the 2A-1 type mutation can include, for example, the yggB gene including IS inserted into the next of "G" at the position 1255 in SEQ ID NO: 7, and thereby coding for a mutant YggB protein having a full length of 423 amino residues, which is shorter than that of the original wild-type YggB protein (SEQ ID NO: 8). The nucleotide sequence of this mutant yggB gene (V419::IS) and the amino acid sequence of the mutant YggB protein encoded by the gene are shown in SEQ ID NOS: 9 and 10, respectively. In the SEQ ID NO: 9, the positions 1 to 1269 correspond to CDS for this mutant YggB protein (V419::IS). Specific examples of the L-glutamic acid-producing bacterium having the mutant yggB gene (V419::IS) can include, for example, the *C. glutamicum* 2256ΔsucAΔldhA yggB* strain (WO2014/185430).

(1-2) Substitution for Proline Residues

Examples of the mutation on the C-terminus side also can include, for example, a mutation that replaces a proline residue present at the positions 419 to 533 of the wild-type YggB protein with another amino acid residue. Examples of such a proline residue can include the proline residues at the positions 424, 437, 453, 457, 462, 469, 484, 489, 497, 515, 529, and 533 of the wild-type YggB protein. It is a particular example to replace the proline residue(s) of the position(s) 424 and/or 437 with other amino acid residue(s). The "other amino acid" is not particularly limited so long as it is a naturally occurring amino acid other than proline. Examples of the "other amino acid" can include Lys, Glu, Thr, Val, Leu, Ile, Ser, Asp, Asn, Gln, Arg, Cys, Met, Phe, Trp, Tyr, Gly, Ala, and His. For example, the proline residue at the position 424 may be replaced with a residue of hydrophobic amino acid (Ala, Gly, Val, Leu, or Ile), or a residue of branched chain amino acid (Leu, Val, or Ile). Furthermore, for example, the proline residue at the position 437 may be replaced with a residue of an amino acid having hydroxyl group in the side chain (Thr, Ser, or Tyr), or with a Ser residue.

(2) Mutation in Transmembrane Region

The YggB protein is estimated to have five transmembrane regions. The transmembrane regions correspond to the amino acid residues of the positions 1 to 23 (first transmembrane region), the positions 25 to 47 (second transmembrane region), the positions 62 to 84 (third transmembrane region), the positions 86 to 108 (fourth transmembrane region), and the positions 110 to 132 (fifth transmembrane region) of the wild-type YggB protein. The mutation in a transmembrane region is a mutation in the regions coding for these transmembrane regions of the wild-type yggB gene. The mutation in transmembrane region may be introduced into one or more sites in the regions. The mutation in transmembrane region can be a mutation that induces substitution, deletion, addition, insertion, or inversion of one or several amino acid residues, but does not include any frame shift mutation or nonsense mutation. The number meant by the term "one or several" can be 1 to 20, 1 to 10, 1 to 5, or 1 to 3. Examples of the mutation in a transmembrane region can include a mutation that inserts one or several amino acid residues, such as Cys-Ser-Leu, between the leucine residue at the position 14 and the tryptophan residue at the position 15; a mutation that replaces the alanine residue at the position 100 with another amino acid residue, such as a residue of an amino acid having hydroxyl group in the side chain, for example, Thr, Ser, or Tyr; a mutation that replaces the alanine residue at the position 111 with another amino acid residue such as a residue of an amino acid having hydroxyl group in the side chain, for example Thr, Ser, or Tyr; in the wild-type YggB protein An "amino acid residue at the position X of the wild-type YggB protein" can mean the amino acid residue corresponding to that of the position X in SEQ ID NO: 8, unless otherwise stated. The "position X" in an amino acid sequence is the X-th position counted from the N-terminus of the amino acid sequence, and the amino acid residue of the N-terminus is the amino acid residue of the position 1. That is, the aforementioned positions of amino acid residues indicate relative positions, and the absolute positions thereof may shift due to deletion, insertion, addition, or the like of an amino acid residue or residues. For example, the "amino acid residue at the position 419 of the wild-type YggB protein" can mean the amino acid residue corresponding to that of the position 419 in SEQ ID NO: 8, and when one amino acid residue is deleted at a position on the N-terminus side of the position 419, the 418th amino acid residue from the N-terminus is "the amino acid residue at the position 419 of the wild-type YggB protein". Furthermore, when one amino acid residue is inserted a position on the N-terminus side of the position 419, the 420th amino acid residue from the N-terminus is "the amino acid residue at the position 419 of the wild-type YggB protein". Specifically, for example, amino acid residues of the positions 419 to 529 of the YggB protein of *Corynebacterium glutamicum* ATCC14967 correspond to amino acid residues of the positions 419 to 533 of the wild-type YggB protein.

Which amino acid residue is "the amino acid residue corresponding to that of the position X in SEQ ID NO: 8" in the amino acid sequence of an arbitrary YggB protein can be determined by alignment between the amino acid sequence of the arbitrary YggB protein and the amino acid sequence of SEQ ID NO: 8. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant yggB gene can be obtained by modifying a wild-type yggB gene so as to have the aforementioned "specific mutation". The modification of DNA can be performed by a known method. For example, an objective mutation can be introduced into an objective site of DNA by the site-specific mutation method. Specific examples of the site-specific mutation method can include, for example, a method of using PCR (Higuchi, R., 61, in PCR Technology, Erlich, H. A. Eds., Stockton Press, 1989; Carter P., Meth. In Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Furthermore, a mutant yggB gene can also be obtained by chemical synthesis.

Such modification of a bacterium that the bacterium has a mutant yggB gene can be attained by introducing the mutant yggB gene into the bacterium. Such modification of a bacterium that the bacterium has a mutant yggB gene can also be attained by introducing a mutation into the yggB gene of the bacterium through natural mutation or a treatment with a mutagen.

The methods for imparting or enhancing L-glutamic acid-producing ability can also be effective for imparting or enhancing an ability to produce L-amino acids that are biosynthesized via L-glutamic acid as an intermediate, such as L-glutamine, L-proline, L-arginine, L-citrulline, and L-ornithine. Hence, a bacterium having an ability to produce any of these L-amino acids that are biosynthesized via L-glutamic acid may have, as required, such a property possessed by an L-glutamic acid-producing bacterium as mentioned above. For example, a bacterium having an ability to produce any of these L-amino acids that are biosynthesized via L-glutamic acid may have been modified so that the activity of α-ketoglutarate dehydrogenase and/or succinate dehydrogenase is reduced.

<L-Glutamine-Producing Bacteria>

Examples of the method for imparting or enhancing L-glutamine-producing ability can include, for example, a method of modifying a bacterium so that the activity or activities of one or more of the L-glutamine biosynthesis enzymes are enhanced. Examples of such enzymes can include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP1229121).

Examples of the method for imparting or enhancing L-glutamine-producing ability also can include, for example, a method of modifying a bacterium so that the activity or activities of one or more enzymes that catalyze a reaction branching away from the biosynthesis pathway of L-glutamine to generate a compound other than L-glutamine are reduced. Examples of such enzymes can include, but not particularly limited to, glutaminase.

Specific examples of L-glutamine-producing bacteria and parental strains that can be used to derive such bacteria can include, for example, coryneform bacteria in which the activity or activities of glutamate dehydrogenase (gdhA) and/or glutamine synthetase (glnA) (EP1229121, EP1424398) are enhanced, and coryneform bacteria in which the glutaminase activity (Japanese Patent Laid-open (Kokai) No. 2004-187684) is reduced. Examples of L-glutamine-producing bacteria and parental strains that can be used to derive such bacteria can include a strain belonging to the genus *Escherichia* and having a mutant glutamine synthetase in which the tyrosine residue of the position 397 of glutamine synthetase has been replaced with another amino acid residue (US2003-0148474A).

Examples of the methods for imparting or enhancing L-glutamine-producing ability to or in coryneform bacteria also can include the method of imparting 6-diazo-5-oxo-norleucine resistance (Japanese Patent Laid-open (Kokai) No. 3-232497), the method of imparting purine analogue resistance and methionine sulfoxide resistance (Japanese Patent Laid-open (Kokai) No. 61-202694), and the method of imparting α-ketomalonic acid resistance (Japanese Patent Laid-open (Kokai) No. 56-151495). Specific examples of coryneform bacteria having L-glutamine-producing ability can include, for example, the following strains:

*Corynebacterium glutamicum* (*Brevibacterium flavum*) AJ11573 (FERM P-5492, Japanese Patent Laid-open (Kokai) No. 56-151495)

*Corynebacterium glutamicum* (*Brevibacterium flavum*) AJ11576 (FERM BP-10381, Japanese Patent Laid-open (Kokai) No. 56-151495)

*Corynebacterium glutamicum* (*Brevibacterium flavum*) AJ12212 (FERM P-8123, Japanese Patent Laid-open (Kokai) No. 61-202694)

<L-Proline-Producing Bacteria>

Examples of methods for imparting or enhancing L-proline-producing ability can include, for example, a method of modifying a bacterium so that the bacterium has an increased activity or activities of one or more of the L-proline biosynthesis enzymes. Examples of such enzymes can include glutamate-5-kinase (proB), γ-glutamylphosphate reductase, and pyroline-5-carboxylate reductase (putA). For enhancing the activity of such an enzyme, for example, the proB gene encoding a glutamate-5-kinase desensitized to feedback inhibition by L-proline (German Patent No. 3127361) can be used.

Examples of methods for imparting or enhancing L-proline-producing ability also can include, for example, a method of modifying a bacterium so that the bacterium has a reduced activity of an enzyme involved in decomposition of L-proline. Examples of such an enzyme can include proline dehydrogenase and ornithine aminotransferase.

Specific examples of L-proline-producing bacteria and parental strains that can be used to derive such bacteria can include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 strain (VKPM B-8011), which is a 3,4-dehydroxyproline and azetidine-2-carboxylate resistant strain, and *E. coli* 702ilvA strain (VKPM B-8012), which is an ilvA gene-deficient strain of the 702 strain (EP1172433).

<L-Threonine-Producing Bacteria>

Examples of methods for imparting or enhancing L-threonine-producing ability can include, for example, a method of modifying a bacterium so that the bacterium has an increased activity or activities of one or more of the L-threonine biosynthesis enzymes. Examples of such enzymes can include, but are not particularly limited to, aspartokinase III (lysC), aspartate semialdehyde dehydrogenase (asci), aspartokinase I (thrA), homoserine kinase (thrB), threonine synthase (thrC), and aspartate aminotransferase (aspartate transaminase) (aspC). Among these enzymes, the activity or activities of one or more of aspartokinase III, aspartate semialdehyde dehydrogenase, aspartokinase I, homoserine kinase, aspartate aminotransferase, and threonine synthase can be enhanced. Any of the genes encoding the L-threonine biosynthesis enzymes can be introduced into a bacterium having a reduced ability to decompose threonine. Examples of such a strain in which threonine decomposition is suppressed can include, for example, the *E. coli* TDH6 strain, which is deficient in the threonine dehydrogenase activity (Japanese Patent Laid-open (Kokai) No. 2001-346578).

The activities of the L-threonine biosynthesis enzymes are inhibited by the endproduct, L-threonine. Therefore, for constructing L-threonine-producing strains, the genes of the L-threonine biosynthesis enzymes can be modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture broth and also suppressed by attenuation. Therefore, expression of the threonine operon can be enhanced by removing the leader sequence or the attenuator in the attenuation region (Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is present upstream of the threonine operon, and can be replaced with a non-native promoter (WO98/04715). Also, the threonine operon may be constructed so that the threonine biosynthesis genes are expressed under control of the repressor and promoter of λ-phage (EP0593792B). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

The expression amount of the threonine operon that is modified so as to be desensitized to feedback inhibition by L-threonine as described above can be increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also can include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance can include the rhtA gene (Res. Microbiol. 154:123-135 (2003)), rhtB gene (EP0994190A), rhtC gene (EP1013765A), yfiK gene, and yeaS gene (EP1016710A). Methods for imparting L-threonine resistance to a host are described in EP0994190A and WO90/04636.

Specific examples of L-threonine-producing bacteria and parental strains that can be used to derive such bacteria can include, for example, *E. coli* TDH-6/pVIC40 (VKPM B-3996, U.S. Pat. Nos. 5,175,107 and 5,705,371), *E. coli* 472T23/pYN7 (ATCC 98081, U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP1149911A), and *E. coli* VKPM B-5318 (EP0593792B).

VKPM B-3996 is a strain obtained by introducing the plasmid pVIC40 into the TDH-6 strain. The TDH-6 strain has sucrose-assimilating ability and is deficient in the thrC gene, and the ilvA gene thereof has a leaky mutation. The TDH-6 strain also has a mutation in the rhtA gene, which imparts resistance to high concentration of threonine or homoserine. The plasmid pVIC40 is a plasmid obtained by inserting the thrA*BC operon containing a mutant thrA gene encoding an aspartokinase-homoserine dehydrogenase I resistant to feedback inhibition by threonine and the wild-type thrBC genes into an RSF1010-derived vector (U.S. Pat. No. 5,705,371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 of which the regulatory region of the threonine operon is replaced with the temperature-sensitive λ-phage Cl repressor and PR promoter. The VKPM B-5318 strain was deposited at the Russian National Collection of Industrial Microorganisms (VKPM, FGUP GosNII Genetika, 1 Dorozhny proezd., 1 Moscow 117545, Russia) on May 3, 1990 under the accession number of VKPM B-5318.

The thrA gene that encodes aspartokinase-homoserine dehydrogenase I of *E. coli* has been elucidated (nucleotide numbers 337 to 2799, GenBank accession NC 000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC 000913.2, gi: 49175990). The thrB gene is located between the thrA and thrC genes on the chromosome of *E. coli* K-12. The thrC gene which encodes threonine synthase of *E. coli* has been elucidated (nucleotide numbers 3734 to 5020, GenBank accession NC 000913.2, gi: 49175990). The thrC gene is located between the thrB gene and the yaaX open reading frame on the chromosome of *E. coli* K-12. The thrA*BC operon containing a mutant thrA gene which encodes an aspartokinase-homoserine dehydrogenase I resistant to feedback inhibition by threonine and the wild-type thrBC genes can be obtained from the well-known plasmid pVIC40, which is present in the threonine-producing *E. coli* strain VKPM B-3996 (U.S. Pat. No. 5,705,371).

The rhtA gene of *E. coli* is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been revealed that the rhtA23 mutation that imparts resistance to high concentration of threonine or homoserine is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457; EP1013765A).

The asd gene of *E. coli* has already been elucidated (nucleotide numbers 3572511 to 3571408, GenBank accession NC 000913.1, gi:16131307), and can be obtained by PCR (White, T. J., et al., Trends Genet, 5:185, 1989) utilizing primers prepared on the basis of the nucleotide sequence of the gene. The asd genes of other microorganisms can also be obtained in a similar manner.

The aspC gene of *E. coli* has also already been elucidated (nucleotide numbers 983742 to 984932, GenBank accession NC 000913.1, gi:16128895), and can be obtained by PCR utilizing primers prepared on the basis of the nucleotide sequence of the gene. The aspC genes of other microorganisms can also be obtained in a similar manner.

Furthermore, examples of coryneform bacteria having L-threonine-producing ability can include, for example, *Corynebacterium acetoacidophilum* AJ12318 (FERM BP-1172, U.S. Pat. No. 5,188,949).

<L-Lysine-Producing Bacteria>

Examples of methods for imparting or enhancing L-lysine-producing ability can include, for example, a method of modifying a bacterium so that the bacterium has an increased activity or activities of one or more of the L-lysine biosynthesis enzymes. Examples of such enzymes can include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195A). The activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase can be enhanced. Furthermore, L-lysine-producing bacteria and parental strains that can be used to derive such bacteria can express an increased level of the gene involved in energy efficiency (cyo) (EP1170376A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Examples of the aspartokinase III desensitized to feedback inhibition by L-lysine can include aspartokinase III derived from *Escherichia coli* and having one or more mutations, such as a mutation for replacing the methionine residue at position 318 with an isoleucine residue; a mutation for replacing the glycine residue at position 323 with an aspartic acid residue; and a mutation for replacing the threonine residue at position 352 with an isoleucine residue (U.S. Pat. Nos. 5,661,012 and 6,040,160). Furthermore, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme. Examples of the dihydrodipicolinate synthase desensitized to feedback inhibition by L-lysine can include dihydrodipicolinate synthase native to or derived from *Escherichia coli* and having a mutation for replacing the histidine residue at position 118 with a tyrosine residue (U.S. Pat. No. 6,040,160).

Examples of methods for imparting or enhancing L-lysine-producing ability also can include, for example, a method of modifying a bacterium so that the bacterium has a reduced activity or activities of one or more kinds of the enzymes that catalyze a reaction branching away from the biosynthetic pathway of L-lysine to generate a compound other than L-lysine. Examples of such enzymes can include, but are not particularly limited to, homoserine dehydrogenase, lysine decarboxylase (U.S. Pat. No. 5,827,698), and malic enzyme (WO2005/010175).

Furthermore, examples of methods for imparting or enhancing L-lysine-producing ability to or in coryneform bacteria also can include a method of modifying the bacteria so that the activity of a lysine excretion system (lysE) is increased (WO97/23597). The lysE gene of *Corynebacterium glutamicum* ATCC 13032 corresponds to the sequence complementary to the sequence of the nucleotide numbers 1,329,712 to 1,330,413 in the genome sequence registered as Genbank Accession No. NC_006958 (VERSION NC_006958.1 GI:62388892) in the NCBI database. The LysE protein of *Corynebacterium glutamicum* ATCC 13032 is registered as GenBank accession No. YP_225551 (YP_225551.1 GI:62390149).

Examples of L-lysine-producing bacteria and parental strains that can be used to derive such bacteria also can include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues can include, but are not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of L-lysine-producing bacteria and parental strains that can be used to derive such bacteria can include *E. coli* AJ11442 (FERM BP-1543, NRRL B-12185, U.S. Pat. No. 4,346,170) and *E. coli* VL611. In these strains, aspartokinase is desensitized to feedback inhibition by L-lysine.

Specific examples of L-lysine-producing bacteria and parental strains that can be used to derive such bacteria also can include the *E. coli* WC196 strain. The WC196 strain was bred by imparting AEC resistance to the W3110 strain, which was derived from *E. coli* K-12 (U.S. Pat. No. 5,827, 698). The WC196 strain was designated *E. coli* AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Examples of L-lysine-producing bacteria can include *E. coli* WC196ΔcadAΔldc and *E. coli* WC196ΔcadAΔldc/ pCABD2 (WO2010/061890). *E. coli* WC196ΔcadAΔldc is a strain constructed from the WC196 strain by disrupting the cadA and ldcC genes encoding lysine decarboxylase. The WC196ΔcadAΔldc/pCABD2 strain was constructed by introducing the plasmid pCABD2 containing lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from *Escherichia coli* and encoding a dihydrodipicolinate synthase (DDPS) having a mutation for desensitization to feedback inhibition by L-lysine (H118Y), a mutant lysC gene derived from *Escherichia coli* and encoding aspartokinase III having a mutation for desensitization to feedback inhibition by L-lysine (T352I), the dapB gene derived from *Escherichia coli* and encoding dihydrodipicolinate reductase, and the ddh gene derived from *Brevibacterium lactofermentum* and encoding diaminopimelate dehydrogenase.

Examples of L-lysine-producing bacteria also can include *E. coli* AJIK01 (NITE BP-01520). The AJIK01 strain was designated *E. coli* AJ111046, and deposited at the independent administrative agency, National Institute of Technology and Evaluation, International Patent Organism Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

Examples of coryneform bacteria having L-lysine-producing ability can include, for example, the AEC-resistant mutant strains (*Corynebacterium glutamicum* (*Brevibacterium lactofermentum* AJ11082) (NRRL B-11470) strain etc., Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437, and 7-112438); mutant strains requiring an amino acid such as L-homoserine for their growth (Japanese Patent Publication Nos. 48-28078 and 56-6499); mutant strains showing resistance to AEC and further requiring an amino acid such as L-leucine, L-homoserine, L-proline, L-serine, L-arginine, L-alanine, and L-valine (U.S. Pat. Nos. 3,708, 395 and 3,825,472); mutant strains showing resistance to DL-α-amino-ε-caprolactam, α-amino-lauryllactam, aspartic acid analogue, sulfa drug, quinoid, and N-lauroylleucine; mutant strains showing resistance to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains showing resistance to ethylene glycol (U.S. Pat. No. 4,411,997).

<L-Arginine-Producing Bacteria>

Examples of methods for imparting or enhancing L-arginine-producing ability can include, for example, a method of modifying a bacterium so that the bacterium has an increased activity or activities of one or more of the L-arginine biosynthesis enzymes. Examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), argininosuccinate synthetase (argG), argininosuccinate lyase (argH), ornithine acetyl transferase (argJ), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (EP1170361A) can be used.

Specific examples of L-arginine-producing bacteria and parental strains that can be used to derive such bacteria can include, for example, the *E. coli* 237 strain (VKPM B-7925, US2002-058315A1), derivative strains thereof introduced with the argA gene encoding a mutant N-acetyl glutamate synthase (Russian Patent Application No. 2001112869, EP1170361A1), *E. coli* 382 strain derived from the 237 strain and having an improved acetic acid-assimilating ability (VKPM B-7926, EP1170358A1), and *E. coli* 382ilvA+ strain, which is a strain obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under accession number of VKPM B-7926.

Examples of L-arginine-producing bacteria and parental strains that can be used to derive such bacteria also can include strains having resistance to amino acid analogues, and so forth. Examples of such strains can include *E. coli* mutant strains having resistance to α-methylmethionine, p-fluorophenylalanine, D-arginine, arginine hydroxamate, S-(2-aminoethyl)-cysteine, α-methyl serine, β-2-thienylalanine, or sulfaguanidine (Japanese Patent Laid-open (Kokai) No. 56-106598).

Examples of L-arginine-producing bacteria and parent strains that can be used to derive such bacteria also can include such coryneform bacteria as a strain deficient in ArgR, which is an arginine repressor (US2002-0045223A), and a strain in which glutamine synthetase activity is increased (US2005-0014236A).

Examples of L-arginine-producing bacteria and parental strains that can be used to derive such bacteria also can include mutant strains of coryneform bacteria, the mutant strains having resistance to an amino acid analogue or the like. Examples of such strains can include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability can include the following strains:

*Corynebacterium glutamicum* (*Brevibacterium flavum*) AJ11169 (FERM BP-6892)

*Corynebacterium glutamicum* (*Brevibacterium lactofermentum*) AJ12092 (FERM BP-6906)

*Corynebacterium glutamicum* (*Brevibacterium flavum*) AJ11336 (FERM BP-6893)

*Corynebacterium glutamicum* (*Brevibacterium flavum*) AJ11345 (FERM BP-6894)

*Corynebacterium glutamicum* (*Brevibacterium lactofermentum*) AJ12430 (FERM BP-2228)

<L-Citrulline-Producing Bacteria and L-Ornithine-Producing Bacteria>

L-citrulline and L-ornithine are intermediates of the biosynthetic pathway of L-arginine. Hence, examples of methods for imparting or enhancing an ability to produce L-citrulline and/or L-ornithine can include, for example, a method of modifying a bacterium so that the bacterium has an increased activity or activities of one or more of the L-arginine biosynthesis enzymes. Examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), ornithine acetyl transferase (argJ), and carbamoyl phosphate synthetase (carAB), for L-citrulline. Furthermore, examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), and ornithine acetyl transferase (argJ), for L-ornithine.

An L-citrulline-producing bacterium can be easily obtained from, for example, an L-arginine bacterium such as the *E. coli* 382 strain (VKPM B-7926) by decreasing the activity of argininosuccinate synthetase encoded by argG gene. Also, an L-ornithine-producing bacterium can be easily obtained from, for example, an L-arginine bacterium such as the *E. coli* 382 strain (VKPM B-7926) by decreasing the activity of ornithine carbamoyl transferase encoded by argF and argI genes.

Specific examples of L-citrulline-producing bacteria and parental strains that can be used to derive such bacteria can include, for example, strains belonging to the genus *Escherichia*, such as the *E. coli* strains 237/pMADS11, 237/pMADS12, and 237/pMADS13, which have a mutant N-acetylglutamate synthase (Russian patent No. 2,215,783, U.S. Pat. No. 6,790,647, and EP1170361B1), *E. coli* strains 333 (VKPM B-8084) and 374 (VKPM B-8086), which have carbamoyl phosphate synthetase resistant to feedback inhibition (Russian patent No. 2,264,459), *E. coli* strains having an increased activity of α-ketoglutarate synthase and having a modified activity of ferredoxin NADP$^+$ reductase, pyruvate synthase, and/or α-ketoglutarate dehydrogenase (EP2133417A); and the *P. ananatis* NA1sucAsdhA strain, which has a reduced activity of succinate dehydrogenase and α-ketoglutarate dehydrogenase (US2009-286290A1).

<L-Histidine-Producing Bacteria>

Examples of methods for imparting or enhancing L-histidine-producing ability can include, for example, a method of modifying a bacterium so that the bacterium has an increased activity or activities of one or more of the L-histidine biosynthesis enzymes. Examples of such enzymes can include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2,003,677 and 2,119,536).

Specific examples of L-histidine-producing bacteria and parental strains that can be used to derive such bacteria can include, for example, strains belonging to the genus *Escherichia*, such as the *E. coli* 24 strain (VKPM B-5945, RU2003677), *E. coli* NRRL B-12116 to B-12121 (U.S. Pat. No. 4,388,405), *E. coli* H-9342 (FERM BP-6675) and H-9343 (FERM BP-6676, U.S. Pat. No. 6,344,347), *E. coli* H-9341 (FERM BP-6674, EP1085087), *E. coli* AI80/pFM201 (U.S. Pat. No. 6,258,554), *E. coli* FERM P-5038 and FERM P-5048, which have been introduced with a vector carrying a DNA encoding an L-histidine-biosynthesis enzyme (Japanese Patent Laid-open (Kokai) No. 56-005099), *E. coli* strains introduced with a gene for amino acid transport (EP1016710A), and *E. coli* 80 strain, which has been imparted with resistance to sulfaguanidine, DL-1, 2,4-triazole-3-alanine, and streptomycin (VKPM B-7270, Russian Patent No. 2119536).

<L-Cysteine-Producing Bacteria>

Examples of methods for imparting or enhancing L-cysteine-producing ability can include, for example, a method of modifying a bacterium so that the bacterium has an increased activity or activities of one or more of the L-cysteine biosynthesis enzymes. Examples of such enzymes can include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and US2005-0112731A. Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of methods for imparting or enhancing L-cysteine-producing ability also can include, for example, a method of modifying a bacterium so that the bacterium has a reduced activity or activities of one or more of the enzymes that catalyze a reaction branching away from the biosynthesis pathway of L-cysteine to generate a compound other than L-cysteine. Examples of such enzymes can include, for example, enzymes involved in decomposition of L-cysteine. Examples of the enzymes involved in decomposition of L-cysteine can include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), O-acetylserine sulfhydrylase B (cysM, Japanese Patent Laid-open (Kokai) No. 2005-245311), the malY gene product (Japanese Patent Laid-open (Kokai) No. 2005-245311), the d0191 gene product of *Pantoea ananatis* (Japanese Patent Laid-open (Kokai) No. 2009-232844), and cysteine desulfhydrase (aecD, Japanese Patent Laid-open (Kokai) No. 2002-233384).

Furthermore, examples of methods for imparting or enhancing L-cysteine-producing ability also can include, for example, a method of enhancing the L-cysteine excretory system, and a method of enhancing the sulfate/thiosulfate transport system. Examples of proteins of the L-cysteine excretory system can include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system can include the proteins encoded by the cysPTWAM gene cluster.

Specific examples of L-cysteine-producing bacteria and parental strains that can be used to derive such bacteria can include, for example, *E. coli* JM15 transformed with different cysE alleles encoding feedback-resistant serine acetyltransferases (U.S. Pat. No. 6,218,168, Russian patent application 2003121601), *E. coli* W3110 having an overexpressed gene encoding a protein suitable for secretion of a cytotoxic substance (U.S. Pat. No. 5,972,663), *E. coli* strains having a reduced cysteine desulfohydrase activity (Japanese Patent Laid-open (Kokai) No. 11-155571), and *E. coli* W3110 having an increased activity of a positive transcriptional regulator for cysteine regulon encoded by the cysB gene (WO01/27307A1).

Furthermore, examples of coryneform bacteria having L-cysteine-producing ability can include coryneform bacteria having serine acetyltransferase desensitized to feedback inhibition by L-cysteine thereby to show enhanced intracellular serine acetyltransferase activity (Japanese Patent Laid-open (Kokai) No. 2002-233384).

<L-Serine-Producing Bacteria>

Examples of methods for imparting or enhancing L-serine-producing ability can include, for example, a method of modifying a bacterium so that the bacterium has an increased activity or activities of one or more of the L-serine biosynthesis enzymes. Examples of such enzymes can include, but are not particularly limited to, 3-phosphoglycerate dehydrogenase (serA), phosphoserine transaminase (serf), and phosphoserine phosphatase (serB) (Japanese Patent Laid-open (Kokai) No. 11-253187). 3-phosphoglycerate dehydrogenase activity can be increased by, for example, introducing a mutant serA gene encoding a mutant 3-phosphoglycerate dehydrogenase resistant to feedback inhibition by L-serine into a bacterium. The mutant 3-phosphoglycerate dehydrogenase is disclosed in, for example, U.S. Pat. No. 6,180,373.

Examples of L-serine-producing bacteria and parental strains that can be used to derive such bacteria can include, for example, coryneform bacteria resistant to azaserine or β-(2-thienyl)-DL-alanine and deficient in L-serine decomposition ability (Japanese Patent Laid-open (Kokai) No. 10-248588). Specific examples of such coryneform bacteria can include, for example, *Corynebacterium glutamicum* (*Brevibacterium flavum*) AJ13324 (FERM P-16128), which is resistant to azaserine and deficient in L-serine decomposition ability, and *Corynebacterium glutamicum* (*Brevibacterium flavum*) AJ13325 (FERM P-16129), which is resistant to β-(2-thienyl)-DL-alanine and deficient in L-serine decomposition ability (Japanese Patent Laid-open (Kokai) No. 10-248588).

<L-Methionine-Producing Bacteria>

Examples of L-methionine-producing bacteria and parental strains that can be used to derive such bacteria can include L-threonine auxotrophic strains and mutant strains resistant to norleucine (Japanese Patent Laid-open (Kokai) No. 2000-139471). Examples of L-methionine-producing bacteria and parental strains that can be used to derive such bacteria also can include a strain containing a mutant homoserine transsuccinylase resistant to feedback inhibition by L-methionine (Japanese Patent Laid-open (Kokai) No. 2000-139471, US2009-0029424A). Since L-methionine is biosynthesized via L-cysteine as an intermediate, L-methionine-producing ability can also be improved by improving L-cysteine-producing ability (Japanese Patent Laid-open (Kokai) No. 2000-139471, US2008-0311632A).

Specific examples of L-methionine-producing bacteria and parental strains that can be used to derive such bacteria can include, for example, *E. coli* AJ11539 (NRRL B-12399), *E. coli* AJ11540 (NRRL B-12400), *E. coli* AJ11541 (NRRL B-12401), *E. coli* AJ11542 (NRRL B-12402, British Patent No. 2075055), the *E. coli* 218 strain (VKPM B-8125, Russian Patent No. 2209248) and the 73 strain (VKPM B-8126, Russian Patent No. 2215782), which are resistant to norleucine, which is an analogue of L-methionine, and *E. coli* AJ13425 (FERMP-16808, Japanese Patent Laid-open (Kokai) No. 2000-139471). The AJ13425 strain is an L-threonine auxotrophic strain derived from the *E. coli* W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting or enhancing L-leucine-producing ability can include, for example, a method of modifying a bacterium so that the bacterium has an increased activity or activities of one or more of the L-leucine biosynthesis enzymes. Examples of such enzymes can include, but are not particularly limited to, the enzymes encoded by the genes of the leuABCD operon. Furthermore, for enhancing the activity of such an enzyme, for example, the mutant leuA gene encoding an isopropyl maleate synthase desensitized to feedback inhibition by L-leucine (U.S. Pat. No. 6,403,342) can be used.

Specific examples of L-leucine-producing bacteria and parental strains that can be used to derive such bacteria can include, for example, strains belonging to the genus *Escherichia*, such as *E. coli* strains resistant to leucine (for example, the 57 strain (VKPM B-7386, U.S. Pat. No. 6,124,121)), *E. coli* strains resistant to a leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879), *E. coli* strains obtained by a gene engineering technique described in WO96/06926, and *E. coli* H-9068 (Japanese Patent Laid-open (Kokai) No. 8-70879).

Examples of coryneform bacteria having L-leucine-producing ability can include, for example, *Corynebacterium glutamicum* (*Brevibacterium lactofermentum*) AJ3718 (FERM P-2516), which is resistant to 2-thiazole alanine and β-hydroxyleucine and auxotrophic for isoleucine and methionine.

<L-Isoleucine-Producing Bacteria>

Examples of methods for imparting or enhancing L-isoleucine-producing ability can include, for example, a method of modifying a bacterium so that the bacterium has increased activity or activities of one or more of the L-isoleucine biosynthesis enzymes. Examples of such enzymes can include, but are not particularly limited to, threonine deaminase and acetohydroxy acid synthase (Japanese Patent Laid-open (Kokai) No. 2-458, EP0356739A, U.S. Pat. No. 5,998,178).

Specific examples of L-isoleucine-producing bacteria and parental strains that can be used to derive such bacteria can include, for example, *Escherichia* bacteria such as mutant strains having resistance to 6-dimethylaminopurine (Japanese Patent Laid-open (Kokai) No. 5-304969), mutant strains having resistance to an isoleucine analogue such as thiaisoleucine and isoleucine hydroxamate, and mutant strains having resistance to such an isoleucine analogue and further having resistance to DL-ethionine and/or arginine hydroxamate (Japanese Patent Laid-open (Kokai) No. 5-130882).

Examples of coryneform bacteria having L-isoleucine-producing ability can include, for example, the coryneform bacterium in which brnE gene encoding a branched chain amino acid excretion protein is amplified (Japanese Patent Laid-open (Kokai) No. 2001-169788), the coryneform bacterium to which L-isoleucine-producing ability is imparted by protoplast fusion with an L-lysine-producing bacterium (Japanese Patent Laid-open (Kokai) No. 62-74293), the coryneform bacterium in which homoserine dehydrogenase is enhanced (Japanese Patent Laid-open (Kokai) No. 62-91193), the threonine hydroxamate resistant strain (Japanese Patent Laid-open (Kokai) No 62-195293), the α-ketomalonic acid resistant strain (Japanese Patent Laid-open (Kokai) No. 61-15695), the methyllysine resistant strain (Japanese Patent Laid-open (Kokai) No. 61-15696), and *Corynebacterium glutamicum* (*Brevibacterium flavum*) AJ12149 (FERM BP-759, U.S. Pat. No. 4,656,135).

<L-Valine-Producing Bacteria>

Examples of methods for imparting or enhancing L-valine-producing ability can include, for example, a method of modifying a bacterium so that the bacterium has an increased activity or activities of one or more of the L-valine biosynthesis enzymes. Examples of such enzymes can include, but are not particularly limited to, the enzymes encoded by the genes of the ilvGMEDA operon and the enzymes encoded by the ilvBNC operon. The ilvBN gene encodes acetohydroxy acid synthase, and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, for enhancing the activity of such an enzyme, it is preferred that the suppression of expression by the produced L-valine is released by removing or modifying a region required for the attenuation. Furthermore, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, for L-valine production, the ilvA gene can be, for example, disrupted, and thereby the threonine deaminase activity is decreased.

Examples of methods for imparting or enhancing L-valine-producing ability also can include, for example, a method of modifying a bacterium so that the bacterium has a reduced activity or activities of one or more of the enzymes that catalyze a reaction branching away from the biosynthesis pathway of L-valine to generate a compound other than L-valine. Examples of such enzymes can include, but are not particularly limited to, threonine dehydratase involved in the L-leucine synthesis, and the enzymes involved in the D-pantothenic acid synthesis (WO00/50624).

Specific examples of L-valine-producing bacteria and parental strains that can be used to derive such bacteria can include, for example, *E. coli* strains modified so as to overexpress the ilvGMEDA operon (U.S. Pat. No. 5,998,178).

Examples of L-valine-producing bacteria and parental strains that can be used to derive such bacteria also can include mutant strains having a mutation in amino-acyl t-RNA synthetase (U.S. Pat. No. 5,658,766). Examples of such strains can include, for example, *E. coli* VL1970, which has a mutation in the ileS gene encoding isoleucine t-RNA synthetase. *E. coli* VL1970 was deposited at the Russian National Collection of Industrial Microorganisms (VKPM, FGUP GosNII Genetika, 1 Dorozhny Proezd, 1 Moscow 117545, Russia) on Jun. 24, 1988 under the accession number of VKPM B-4411. Examples of L-valine-producing bacteria and parental strains that can be used to derive such bacteria also can include mutant strains requiring lipoic acid for growth and/or lacking $H^+$-ATPase (WO96/06926).

Examples of L-valine-producing bacteria and parental strains that can be used to derive such bacteria also can include strains resistant to an amino acid analogue or the like. Examples of such strains can include, for example, the coryneform bacterium strains which are auxotrophic for L-isoleucine and L-methionine, and resistant to D-ribose, purine ribonucleoside, or pyrimidine ribonucleoside, and have an ability to produce L-valine (FERM P-1841, FERM P-29) (Japanese Patent Publication No. 53-025034), coryneform bacterium strains resistant to polyketides (FERM P-1763, FERM P-1764) (Japanese Patent Publication No. 06-065314), and coryneform bacterium strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007) (Japanese Patent No. 3006929).

<L-Alanine-Producing Bacteria>

Examples of L-alanine-producing bacteria and parental strains that can be used to derive such bacteria can include the coryneform bacteria deficient in the $H^+$-ATPase (Appl. Microbiol. Biotechnol., 2001 November, 57(4):534-40) and coryneform bacteria in which the aspartate β-decarboxylase activity is enhanced (Japanese Patent Laid-open (Kokai) No. 07-163383).

<L-Tryptophan-Producing Bacteria, L-Phenylalanine-Producing Bacteria, and L-Tyrosine-Producing Bacteria>

Examples of methods for imparting or enhancing L-tryptophan-producing ability, L-phenylalanine-producing ability, and/or L-tyrosine-producing ability can include, for example, a method of modifying a bacterium so that the bacterium has an increased activity or activities of one or more of the L-tryptophan, L-phenylalanine, and/or L-tyrosine biosynthesis enzymes.

Examples of enzymes common to the biosynthesis systems of these aromatic amino acids can include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP763127B). The expressions of the genes encoding these enzymes are controlled by the tyrosine repressor (tyrR), and the activities of these enzymes may be enhanced by deleting the tyrR gene (EP763127B).

Examples of the L-tryptophan biosynthesis enzymes can include, but are not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase is made up of α and β subunits encoded by the trpA and trpB genes, respectively. Since the anthranilate synthase is subject to feedback inhibition by L-tryptophan, a gene encoding this enzyme introduced with a mutation for desensitization to feedback inhibition may be used for enhancing the activity of that enzyme. Since the phosphoglycerate dehydrogenase is subject to feedback inhibition by L-serine, a gene encoding this enzyme introduced with a mutation for desensitization to feedback inhibition may be used for enhancing the activity of that enzyme. Furthermore, by increasing the expression of the operon (ace operon) consisting of the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthesis enzymes can include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, genes encoding these enzymes introduced with a mutation for desensitization to feedback inhibition may be used for enhancing the activities of these enzymes.

Examples of the L-tyrosine biosynthesis enzymes can include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, genes encoding these enzymes introduced with a mutation for desensitization to feedback inhibition may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Furthermore, the L-tryptophan, L-phenylalanine, and/or L-tyrosine-producing bacteria may be modified so that a by-product uptake system is enhanced. Examples of the by-product can include aromatic amino acids other than the objective aromatic amino acid. Examples of the gene encoding such a by-product uptake system can include, for example, tnaB and mtr, which are genes encoding the L-tryptophan uptake system, pheP, which is a gene encoding the L-phenylalanine uptake system, and tyrP, which is a gene encoding the L-tyrosine uptake system (EP1484410).

Specific examples of L-tryptophan-producing bacteria and parental strains that can be used to derive such bacteria can include, for example, E. coli JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), E. coli SV164, which has a trpE allele encoding an anthranilate synthase desensitized to feedback inhibition by tryptophan, E. coli SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), E. coli AGX17(pGX44) (NRRL B-12263) and AGX6(pGX50)aroP (NRRL B-12264), which are deficient in tryptophanase (U.S. Pat. No. 4,371,614), E. coli AGX17/pGX50, pACKG4-pps, which has an increased phosphoenolpyruvate-producing ability (WO97/08333, U.S. Pat. No. 6,319,696), and strains belonging to the genus Escherichia having an increased activity of the protein encoded by the yedA or yddG gene (US2003-0148473A1 and US2003-0157667A1).

Examples of coryneform bacteria having L-tryptophan-producing ability can include, for example, Corynebacterium glutamicum AJ12118 (FERM BP-478, Japanese Patent No. 1681002), which is resistant to sulfaguanidine, the strain introduced with the tryptophan operon (Japanese Patent Laid-open (Kokai) No. 63-240794), and the strain introduced with a gene encoding shikimate kinase derived from a coryneform bacterium (Japanese Patent No. 1994749).

Specific examples of L-phenylalanine-producing bacteria and parental strains that can be used to derive such bacteria can include, for example, E. coli AJ12739 (tyrA::Tn10, tyrR) (VKPM B-8197), which is deficient in the chorismate mutase-prephenate dehydrogenase and the tyrosine repressor (WO03/044191), E. coli HW1089 (ATCC 55371), which contains a mutant pheA34 gene encoding a chorismate mutase-prephenate dehydratase desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Specific examples of L-phenylalanine-producing bacteria and parental strains that can be used to derive such bacteria also can include, for example, E. coli K-12<W3110 (tyrA)/pPHAB> (FERM BP-3566), E. coli K-12 <W3110 (tyrA)/pPHAD> (FERM BP-12659), E. coli K-12<W3110 (tyrA)/pPHATerm> (FERM BP-12662), and E. coli K-12 AJ12604 <W3110(tyrA)/pBR-aroG4, pACMAB> (FERM BP-3579), which contains a gene encoding a chorismate mutase-prephenate dehydratase desensitized to feedback inhibition (EP488424B1). Specific examples of L-phenylalanine-producing bacteria and parental strains that can be used to derive such bacteria further can include, for example, strains belonging to the genus Escherichia having an increased activity of the protein encoded by the yedA gene or the yddG gene (US2003-0148473A, US2003-0157667A, WO03/044192).

Examples of coryneform bacteria having L-phenylalanine-producing ability can include, for example, the *Corynebacterium glutamicum* strains BPS-13 (FERM BP-1777), K77 (FERM BP-2062), and K78 (FERM BP-2063) (EP331145A, Japanese Patent Laid-open (Kokai) No. 02-303495), of which phosphoenolpyruvate carboxylase or pyruvate kinase activity is reduced, and the tyrosine-auxotrophic strain (Japanese Patent Laid-open (Kokai) No. 05-049489).

Examples of coryneform bacteria having L-tyrosine-producing ability can include, for example, *Corynebacterium glutamicum* AJ11655 (FERM P-5836, Japanese Patent Publication No. 2-6517), and *Corynebacterium glutamicum* (*Brevibacterium lactofermentum*) AJ12081 (FERM P-7249, Japanese Patent Laid-open (Kokai) No. 60-70093).

Furthermore, examples of methods for imparting or enhancing an L-amino acid-producing ability can include, for example, a method of modifying a bacterium so that the bacterium has an increased activity for secreting an L-amino acid from a bacterial cell. Such an activity for secreting an L-amino acid can be increased by, for example, increasing the expression of a gene encoding a protein responsible for secretion of the L-amino acid. Examples of genes encoding the proteins responsible for secretion of various amino acids can include, for example, b2682 gene (ygaZ), b2683 gene (ygaH), b1242 gene (ychE), and b3434 gene (yhgN) (Japanese Patent Laid-open (Kokai) No. 2002-300874).

Furthermore, examples of methods for imparting or enhancing an L-amino acid-producing ability also can include, for example, a method of modifying a bacterium so that the bacterium has an increased activity or activities of one or more proteins selected from proteins involved in the glycometabolism and proteins involved in the energy metabolism.

Examples of the proteins involved in the glycometabolism can include proteins involved in uptake of saccharides and the glycolysis system enzymes. Examples of genes encoding a protein involved in the glycometabolism can include glucose-6-phosphate isomerase gene (pgi, WO01/02542), pyruvate carboxylase gene (pyc, WO99/18228, EP1092776A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP1149911A), and sucrose assimilation gene (scrAB operon, U.S. Pat. No. 7,179,623).

Examples of genes encoding the proteins involved in the energy metabolism can include the transhydrogenase gene (pntAB, U.S. Pat. No. 5,830,716) and cytochrome bo-type oxidase gene (cyoB, EP1070376A).

Furthermore, examples of methods for imparting or enhancing an ability to produce useful substances such as L-amino acids can include, for example, a method of modifying a bacterium so that the activity of phosphoketolase is increased (WO2006/016705). Hence, the bacterium may have been modified so that the activity of phosphoketolase is increased. This method may be effective particularly for imparting or enhancing an ability to produce an L-amino acid of glutamate family such as L-glutamic acid. Examples of phosphoketolase can include D-xylulose-5-phosphate phosphoketolase and fructose-6-phosphate phosphoketolase. Either one of the D-xylulose-5-phosphate phosphoketolase activity and the fructose-6-phosphate phosphoketolase activity may be enhanced, or both may be enhanced.

The term "D-xylulose-5-phosphate phosphoketolase activity" can refer to an activity for converting xylulose-5-phosphate into glycelaldehyde-3-phosphate and acetyl phosphate with consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183:2929-2936, 2001). Examples of D-xylulose-5-phosphate phosphoketolase can include those of bacteria belonging to the genera *Acetobacter, Bifidobacterium, Lactobacillus, Thiobacillus, Streptococcus, Methylococcus, Butyrivibrio,* and *Fibrobacter,* and yeast belonging to the genera *Candida, Rhodotorula, Rhodosporidium, Pichia, Yarrowia, Hansenula, Kluyveromyces, Saccharomyces, Trichosporon,* and *Wingea*. Specific examples of D-xylulose-5-phosphate phosphoketolase and genes encoding them are disclosed in WO2006/016705.

The term "fructose-6-phosphate phosphoketolase activity" can refer to an activity for converting fructose-6-phosphate into erythrose-4-phosphate and acetyl phosphate with consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001). Examples of fructose-6-phosphate phosphoketolase can include those of bacteria belonging to the genera *Acetobacter, Bifidobacterium, Chlorobium, Brucella, Methylococcus,* and *Gardnerella,* and yeast belonging to the genera *Rhodotorula, Candida,* and *Saccharomyces*. Specific examples of fructose-6-phosphate phosphoketolase and genes encoding them are disclosed in WO2006/016705.

Both the D-xylulose-5-phosphate phosphoketolase activity and the fructose-6-phosphate phosphoketolase activity may also be retained by a single enzyme (i.e. D-xylulose-5-phosphate phosphoketolase/fructose-6-phosphate phosphoketolase).

The genes and proteins used for breeding L-amino acid-producing bacteria may have, for example, the nucleotide sequences and amino acid sequences of known genes and proteins, such as those exemplified above, respectively. Also, the genes and proteins used for breeding L-amino acid-producing bacteria may be conservative variants of known genes and proteins, such as those exemplified above, respectively. Specifically, for example, the genes used for breeding L-amino acid-producing bacteria may each be a gene encoding a protein having an amino acid sequence of a known protein, but including substitution, deletion, insertion, or addition of one or several amino acid residues at one or several positions, so long as the original function thereof is maintained. For the conservative variants of genes and proteins, the descriptions concerning conservative variants of the carotenoid biosynthesis enzyme gene and carotenoid biosynthesis enzyme mentioned later can be similarly applied.

Furthermore, the bacterium may have an ability to produce a carotenoid. The phrase "bacterium may have an ability to produce a carotenoid" or "carotenoid-producing ability" can refer to a bacterium having an ability to generate and accumulate an objective carotenoid in cells of the bacterium, when the bacterium is cultured in a medium. The bacterium having a carotenoid-producing ability may be a bacterium that is able to accumulate an objective carotenoid in cells of the bacterium in an amount larger than that obtainable with a non-modified strain. The term "non-modified strain" can refer to a control strain that has not been modified so that the activity of a carotenoid biosynthesis enzyme is increased. That is, examples of the non-modified strain can include a wild-type strain and parental strain. The bacterium having a carotenoid-producing ability may be a bacterium that is able to accumulate an objective carotenoid in cells of the bacterium in an amount of 10 µg/g-DCW or more, 50 µg/g-DCW or more, 100 µg/g-DCW or more, 200 µg/g-DCW or more, or 500 µg/g-DCW or more. The amount of an objective carotenoid accumulated in cells of the bacterium having a carotenoid-producing ability may also be, for example, 100 mg/g-DCW or less, 50 mg/g-DCW or less, 10 mg/g-DCW or less, 5 mg/g-DCW or less, or 1 mg/g-DCW or less. The amount of an objective carotenoid accumulated in cells of the bacterium having a carotenoid-producing ability may also be within a range defined by any combination of the ranges exemplified above. The term "DCW" refers to dry cell weight. Examples of the carotenoid can include carotenes and xanthophylls. Specific examples of the carotenoid can include, for example, phytoene, phytofluene, zeta-carotene, neurosporene, lycopene, beta-carotene, beta-cryptoxanthin, echinenone, 3-hydroxyechinenone, 3'-hydroxyechinenone, zeaxanthin, canthaxanthin, adonixanthin, adonirubin, and astaxanthine. Particular examples of the carotenoid can include beta-carotene, zeaxanthin, canthaxanthin, and astaxanthine. More particular examples of the carotenoid can include astaxanthine. The bacterium may have an ability to produce a single kind of carotenoid, or two or more kinds of carotenoids. The accumulation amount of carotenoid exemplified above may represent, for example, the amount of all the carotenoids, or the amount of one or more selected carotenoids. The bacterium may inherently be able to produce a carotenoid, or may be modified so that it is able to produce a carotenoid. The bacterium having a carotenoid-producing ability can be obtained by imparting a carotenoid-producing ability to such a bacterium as mentioned above, or by enhancing a carotenoid-producing ability of such a bacterium as mentioned above. A carotenoid-producing ability can be imparted or enhanced by, for example, modifying a bacterium so that the bacterium has an increased activity of a carotenoid biosynthesis enzyme.

<1-2> Enhancement of Carotenoid Biosynthesis Enzyme Activity

The bacterium as described herein has been modified so that the activity of a carotenoid biosynthesis enzyme is increased. Specifically, the bacterium has been modified so that the activity of a carotenoid biosynthesis enzyme is increased as compared with a non-modified strain. The bacterium can be obtained by modifying a bacterium having an L-amino acid-producing ability so that the activity of a carotenoid biosynthesis enzyme is increased. The bacterium can also be obtained by modifying a bacterium so that the activity of a carotenoid biosynthesis enzyme is increased, and then imparting or enhancing an L-amino acid-producing ability. The bacterium may also be a bacterium that has acquired an L-amino acid-producing ability by being modified so that the activity of a carotenoid biosynthesis enzyme is increased. The bacterium may have, as required, such a property possessed by an L-amino acid-producing bacterium as mentioned above. The modifications for constructing the bacterium can be performed in an arbitrary order.

By modifying a bacterium so that the activity of a carotenoid biosynthesis enzyme is increased, an L-amino acid-producing ability of the bacterium can be improved, and that is, production of an L-amino acid by using the bacterium can be increased.

Hereinafter, carotenoid biosynthesis enzymes and genes encoding them will be explained.

The term "carotenoid biosynthesis enzyme" can refer to a protein involved in the biosynthesis of a carotenoid. A gene encoding a carotenoid biosynthesis enzyme can also be referred to as "carotenoid biosynthesis enzyme gene".

Carotenoids are biosynthesized via farnesyl pyrophosphate as an intermediate. Hence, examples of the carotenoid biosynthesis enzyme can include enzymes catalyzing the conversion from farnesyl pyrophosphate into carotenoids such as astaxanthine.

Astaxanthine can be biosynthesized via, for example, the following reactions. That is, farnesyl pyrophosphate can be converted into geranylgeranyl pyrophosphate by the action of geranylgeranyl pyrophosphate synthase. Geranylgeranyl pyrophosphate can be converted into phytoene by the action of phytoene synthase. Phytoene can be converted into lycopene via 4 steps of desaturation by the action of phytoene desaturase. Lycopene can be converted into beta-carotene by the action of lycopene beta-cyclase. Beta-carotene can be converted into astaxanthine via 2 steps of ketolation and 2 steps of hydroxylation by the action of carotene ketolase and carotene hydroxylase. Hence, specific examples of the carotenoid biosynthesis enzyme can include geranylgeranyl pyrophosphate synthase, phytoene synthase, phytoene desaturase, lycopene beta-cyclase, carotene ketolase, and carotene hydroxylase.

The term "geranylgeranyl pyrophosphate synthase" can refer to a protein that has the activity of catalyzing the reaction of converting farnesyl pyrophosphate and isopentenyl pyrophosphate into geranylgeranyl pyrophosphate and pyrophosphate (EC 2.5.1.29). This activity can also be referred to as "geranylgeranyl pyrophosphate synthase activity". Examples of geranylgeranyl pyrophosphate synthase can include the CrtE protein, which is encoded by the crtE gene.

The term "phytoene synthase" can refer to a protein that has the activity of catalyzing the reaction of converting two molecules of geranylgeranyl pyrophosphate into one molecule of phytoene and two molecules of pyrophosphate (EC 2.5.1.32 or EC 2.5.1.99). This activity can also be referred to as "phytoene synthase activity". Examples of phytoene synthase can include CrtB protein, which is encoded by crtB gene.

The term "phytoene desaturase" can refer to a protein that has the activity of catalyzing the reaction of desaturating a linear carotene such as phytoene, phytofluene, zeta-carotene, or neurosporene. This activity can also be referred to as "phytoene desaturase activity". Phytoene can be converted into lycopene via 4 steps of desaturation. Specifically, phytoene can be successively desaturated into phytofluene, zeta-carotene, neurosporene, and lycopene. Specific examples of phytoene desaturase can include phytoene desaturase (lycopene-forming), which catalyzes 4 steps of desaturation from phytoene into lycopene (EC 1.3.99.31 etc.); phytoene desaturase (zeta-carotene-forming), which catalyzes 2 steps of desaturation from phytoene into zeta-carotene (EC 1.3.5.6, EC 1.3.99.29, etc.); and zeta-carotene desaturase, which catalyzes 2 steps of desaturation from zeta-carotene into lycopene (EC 1.3.5.6, EC 1.3.99.26, etc.). Examples of phytoene desaturase (lycopene-forming) can include the CrtI protein, which is encoded by the crtI gene. Examples of phytoene desaturase (zeta-carotene-forming) can include the CrtP protein (synonym: Pds protein), which is encoded by the crtP gene (synonym: pds gene). Examples of zeta-carotene desaturase can include the CrtQ protein, which is encoded by the crtQ gene. As phytoene desaturase, for example, phytoene desaturase (lycopene-forming) may be used, or a combination of phytoene desaturase (zeta-carotene-forming) and zeta-carotene desaturase may be used.

The term "lycopene beta-cyclase" can refer to a protein that has the activity of catalyzing the reaction of cyclizing lycopene to generate beta-carotene (EC 5.5.1.19). This activity can also be referred to as "lycopene beta-cyclase activity". Examples of lycopene beta-cyclase can include CrtY and CrtL proteins, which are encoded by crtY and crtL genes, respectively.

The term "carotene ketolase" can refer to a protein that has the activity of catalyzing the reaction of introducing a keto group into the ionone ring of a cyclic carotene (EC 1.3.5.B4, EC 1.14.11.B16, EC 1.17.5.B2, etc.). This activity can also be referred to as "carotene ketolase activity". Examples of carotene ketolase can include CrtW and CrtO proteins, which are encoded by the crtW and crtO genes, respectively.

The term "carotene hydroxylase" can refer to a protein that has the activity of catalyzing the reaction of introducing a hydroxyl group into the ionone ring of a cyclic carotene (EC 1.14.13.129). This activity can also be referred to as "carotene hydroxylase activity". Examples of carotene hydroxylase can include the CrtZ and CrtR proteins, which are encoded by the crtZ and crtR genes, respectively.

The activity of one kind of carotenoid biosynthesis enzyme may be increased, or the activities of two or more kinds of carotenoid biosynthesis enzymes may be increased. The number and kind(s) of carotenoid biosynthesis enzyme(s) of which the activity or activities is/are increased are not particularly limited. The carotenoid biosynthesis enzyme(s) of which the activity or activities is/are increased may be selected so that, for example, a carotenoid-producing ability is imparted or enhanced. For example, at least the activity or activities of one or more of geranylgeranyl pyrophosphate synthase, phytoene synthase, phytoene desaturase, and lycopene beta-cyclase may be increased. Also, for example, at least the activities of geranylgeranyl pyrophosphate synthase, phytoene synthase, phytoene desaturase, and lycopene beta-cyclase may be increased. Also, for example, in addition to the activity or activities of this/these enzyme(s), the activity or activities of carotene ketolase and/or carotene hydroxylase may further be increased.

Examples of the carotenoid biosynthesis enzyme gene can include genes of, or native to, various organisms such as plants, algae, and bacteria. Examples of bacteria having the carotenoid biosynthesis enzyme gene can include, for example, bacteria belonging to the family Enterobacteriaceae, such as *Pantoea* bacteria; bacteria belonging to the family Caulobacteraceae, such as *Brevundimonas* bacteria; bacteria belonging to the family Rhodobacteraceae, such as *Paracoccus* bacteria; bacteria belonging to the family Alcaligenaceae, such as *Alcaligenes* bacteria; coryneform bacteria such as *Corynebacterium* bacteria; cyanobacteria such as *Nostoc* bacteria and *Synechococcus* bacteria. The nucleotide sequences of the carotenoid biosynthesis enzyme genes derived from these various organisms and the amino acid sequences of the carotenoid biosynthesis enzymes encoded by these genes can be obtained from, for example, public databases such as NCBI. Specific examples of the crtE, crtB, crtI, crtY, and crtZ genes can include, for example, the crtE, crtB, crtI, crtY, and crtZ genes of *Pantoea* bacteria such as *Pantoea ananatis* and *Pantoea agglomerans*. The nucleotide sequences of the crtE, crtB, crtI, crtY, and crtZ genes of *Pantoea ananatis* AJ13355 are shown in SEQ ID NOS: 11, 13, 15, 17, and 21, respectively. The amino acid sequences of the CrtE, CrtB, CrtI, CrtY, and CrtZ proteins encoded by these genes are shown in SEQ ID NOS: 12, 14, 16, 18, and 22, respectively. Furthermore, specific examples of the crtE, crtB, and crtI genes can include, for example, the crtE, crtB, and crtI genes of *Corynebacterium* bacteria such as *Corynebacterium glutamicum*. The nucleotide sequences of the crtE (cg0723), crtB (cg0721), and crtI (cg0720) genes of *Corynebacterium glutamicum* ATCC 13032 are shown in SEQ ID NOS: 23, 25, and 27, respectively. The amino acid sequences of the CrtE, CrtB, and CrtI proteins encoded by these genes are shown in SEQ ID NOS: 24, 26, and 28, respectively.

Furthermore, specific examples of crtW gene can include, for example, the crtW genes of *Nostoc* bacteria such as *Nostoc* sp. and *Nostoc punctiforme* and *Brevundimonas* bacteria such as *Brevundimonas aurantiaca*. The nucleotide sequence of the crtW gene of *Nostoc* sp. PCC 7120 and the amino acid sequence of the protein encoded by the gene are shown in SEQ ID NOS: 19 and 20, respectively. The nucleotide sequence of the crtW gene of *Nostoc punctiforme* (codon-optimized for expression in *E. coli*) and the amino acid sequence of the protein encoded by the gene are shown in SEQ ID NOS: 50 and 61, respectively. The nucleotide sequence of the crtW gene of *Brevundimonas aurantiaca* and the amino acid sequence of the protein encoded by the gene are shown in SEQ ID NOS: 29 and 30, respectively. Furthermore, specific examples of the crtZ gene can include, for example, the crtZ genes of *Brevundimonas* bacteria such as *Brevundimonas* sp., *Paracoccus* bacteria such as *Paracoccus* sp., and *Alcaligenes* bacteria such as *Alcaligenes* sp. The nucleotide sequence of the crtZ gene of *Brevundimonas* sp. SD-212 and the amino acid sequence of the protein encoded by the gene are shown in SEQ ID NOS: 37 and 58, respectively. The nucleotide sequence of the crtZ gene of *Paracoccus* sp. N81106 and the amino acid sequence of the protein encoded by the gene are shown in SEQ ID NOS: 42 and 59, respectively. The nucleotide sequence of the crtZ gene of *Alcaligenes* sp. and the amino acid sequence of the protein encoded by the gene are shown in SEQ ID NOS: 46 and 60, respectively. Furthermore, specific examples of the crtP, crtQ, crtO, and crtR genes can include, for example, the crtP (pds), crtQ, crtO, and crtR genes of cyanobacteria such as *Synechococcus* bacteria. That is, the carotenoid biosynthesis enzyme gene may be, for example, a gene having the nucleotide sequence of any of the carotenoid biosynthesis enzyme genes exemplified above, such as the nucleotide sequence shown as SEQ ID NO: 11, 13, 15, 17, 19, 21, 23, 25, 27, 29, 37, 42, 46, or 50. Also, the carotenoid biosynthesis enzyme may be, for example, a protein having the amino acid sequence of any of the carotenoid biosynthesis enzymes exemplified above, such as the amino acid sequence shown as SEQ ID NO: 12, 14, 16, 18, 20, 22, 24, 26, 28, 30, 58, 59, 60, or 61. The expression "a gene or protein has a nucleotide or amino acid sequence" can mean that a gene or protein includes the nucleotide or amino acid sequence unless otherwise stated, and also includes when a gene or protein includes only the nucleotide or amino acid sequence.

The carotenoid biosynthesis enzyme gene may be a variant of any of the carotenoid biosynthesis enzyme genes exemplified above (e.g. a gene having the nucleotide sequence shown as SEQ ID NO: 11, 13, 15, 17, 19, 21, 23, 25, 27, 29, 37, 42, 46, or 50), so long as the original function thereof is maintained. Similarly, the carotenoid biosynthesis enzyme may be a variant of any of the carotenoid biosynthesis enzymes exemplified above (e.g. a protein having the amino acid sequence shown as SEQ ID NO: 12, 14, 16, 18, 20, 22, 24, 26, 28, 30, 58, 59, 60, or 61), so long as the original function thereof is maintained. Such a variant that maintains the original function thereof can also be referred to as "conservative variant". A gene defined with the above-mentioned gene name and a protein defined with the above-mentioned protein name can include not only the genes and proteins exemplified above, respectively, but also can include conservative variants thereof. Namely, for example, the term the "crtE gene" includes not only the crtE genes exemplified above, but also can include conservative variants thereof. Similarly, the term "CrtE protein" includes not only the CrtE proteins exemplified above, but also can include conservative variants thereof. Examples of the conservative variants can include, for example, homologues and artificially modified versions of the carotenoid biosynthesis enzyme genes and carotenoid biosynthesis enzymes exemplified above.

The expression "the original function is maintained" can mean that a variant of gene or protein has a function (such as activity or property) corresponding to the function (such as activity or property) of the original gene or protein. The expression "the original function is maintained" used for a gene means that a variant of the gene encodes a protein that maintains the original function. That is, the expression "the original function is maintained" used for the carotenoid biosynthesis enzyme gene means that a variant of the gene encodes a protein having the corresponding carotenoid biosynthesis enzyme activity, e.g. geranylgeranyl pyrophosphate synthase activity for a geranylgeranyl pyrophosphate synthase gene. Furthermore, the expression "the original function is maintained" used for the carotenoid biosynthesis enzyme means that a variant of the protein has the corresponding carotenoid biosynthesis enzyme activity, e.g. geranylgeranyl pyrophosphate synthase activity for geranylgeranyl pyrophosphate synthase.

Each carotenoid biosynthesis enzyme activity can be measured by, for example, incubating the enzyme with a substrate corresponding to the activity to be measured, and measuring the enzyme- and substrate-dependent generation of a product corresponding to the activity to be measured. For example, geranylgeranyl pyrophosphate synthase activity can be measured by incubating the enzyme with a substrate (i.e. farnesyl pyrophosphate and isopentenyl pyrophosphate), and measuring the enzyme- and substrate-dependent generation of a product (i.e. geranylgeranyl pyrophosphate).

Hereinafter, examples of the conservative variants will be explained.

Homologues of the carotenoid biosynthesis enzyme genes or homologues of the carotenoid biosynthesis enzymes can be easily obtained from public databases by, for example, BLAST search or FASTA search using any of the nucleotide sequences of the carotenoid biosynthesis enzyme genes exemplified above or any of the amino acid sequences of the carotenoid biosynthesis enzymes exemplified above as a query sequence. Furthermore, homologues of the carotenoid biosynthesis enzyme genes can be obtained by, for example, PCR using a chromosome of various organisms as the template, and oligonucleotides prepared on the basis of any of the nucleotide sequences of these known carotenoid biosynthesis enzyme genes as primers.

The carotenoid biosynthesis enzyme gene may be a gene encoding a protein having any of the aforementioned amino acid sequences (e.g. the amino acid sequence shown as SEQ ID NO: 12, 14, 16, 18, 20, 22, 24, 26, 28, 30, 58, 59, 60, or 61), but which includes substitution, deletion, insertion, and/or addition of one or several amino acid residues at one or several positions, so long as the original function is maintained. For example, the N-terminus and/or the C-terminus of the encoded protein may be elongated or shortened. Although the number meant by the term "one or several" mentioned above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues are/is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion, or the like of amino acid residues as mentioned above includes a naturally occurring mutation due to an individual difference, or a difference of species of the organism from which the gene is derived (mutant or variant).

The carotenoid biosynthesis enzyme gene may be a gene encoding a protein having an amino acid sequence showing a homology of, for example, 50% or more, 65% or more, 80% or more, 90% or more, 95% or more, 97% or more, or 99% or more, to the total amino acid sequence of any of the aforementioned above amino acid sequences, so long as the original function is maintained. In this description, "homology" can mean "identity".

The carotenoid biosynthesis enzyme gene may also be a DNA that is able to hybridize under stringent conditions with a probe that can be prepared from any of the aforementioned nucleotide sequences (e.g. the nucleotide sequence shown as SEQ ID NO: 11, 13, 15, 17, 19, 21, 23, 25, 27, 29, 37, 42, 46, or 50), such as a sequence complementary to a partial or entire sequence of any of the aforementioned nucleotide sequences, so long as the original function is maintained. The term "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90%, 95%, 97%, or 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, arbitrary codons in the carotenoid biosynthesis enzyme gene may be replaced with respective equivalent codons. That is, the carotenoid biosynthesis enzyme gene may be a variant of any of the carotenoid biosynthesis enzyme genes exemplified above due to the degeneracy of the genetic code. For example, the carotenoid biosynthesis enzyme gene may be a gene modified so that it has optimal codons according to codon frequencies in a host to be used.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The aforementioned descriptions concerning conservative variants of the genes and proteins can be similarly applied to variants of arbitrary proteins such as L-amino acid biosynthesis system enzymes and genes encoding them.

<1-3> Methods for Increasing Activity of Protein

Hereinafter, methods for increasing the activity of a protein such as the carotenoid biosynthesis enzyme will be explained.

The expression "the activity of a protein is increased" can mean that the activity of the protein is increased as compared with a non-modified strain. Specifically, the expression "the activity of a protein is increased" may mean that the activity of the protein per cell is increased as compared with that of a non-modified strain. The term "non-modified strain" can refer to a control strain that has not been modified so that the activity of an objective protein is increased. Examples of the non-modified strain can include a wild-type strain and parent strain. Specific examples of the non-modified strain can include the respective type strains of the species of microorganisms. Specific examples of the non-modified strain also can include strains exemplified above in relation to the description of microorganisms. That is, in an embodiment, the activity of a protein may be increased as compared with, for example, the same type of strain of the species to which the microorganism as described herein belongs. In another embodiment, the activity of a protein may also be increased as compared with the *E. coli* MG1655 strain. In another embodiment, the activity of a protein may also be increased as compared with the *P. ananatis* AJ13355 strain. In another embodiment, the activity of a protein may also be increased as compared with the *C. glutamicum* ATCC 13869 strain. The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the gene (i.e. the amount of the protein). Furthermore, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" means that the expression of the gene is increased as compared with a non-modified strain such as a wild-type strain and parent strain. Specifically, the expression "the expression of a gene is increased" may mean that the expression amount of the gene per cell is increased as compared with that of a non-modified strain such as a wild-type strain and parent strain. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased to, for example, 1.5 times or more, 2 times or more, or 3 times or more of that of a non-modified strain. Furthermore, the state that "the expression of a gene is increased" can include not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP805867B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); pVK9 (US2006-0141588); pVC7 (Japanese Patent Laid-open (Kokai) No. 9-070291); pVS7 (WO2013/069634).

When a gene is introduced, it is sufficient that the gene is expressibly harbored by a host. Specifically, it is sufficient that the gene is harbored by a host so that it is expressed under control by a promoter sequence that functions in the host. The promoter is not particularly limited so long as it functions in the host. The term "promoter that functions in a host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in the host. The terminator may be a terminator derived from the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by the host. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced. The case of "introducing two or more genes" can include, for example, cases of introducing respective genes encoding two or more kinds of proteins (such as enzymes), introducing respective genes encoding two or more subunits constituting a single protein complex (such as enzyme complex), and a combination of the foregoing cases.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein can include substitution, deletion, insertion, and/or addition of amino acid residues. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

Incidentally, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that encode the subunits may be enhanced. It is usually preferable to enhance the expression of all of the plurality of genes encoding the subunits. Furthermore, the subunits constituting the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can refer to a promoter providing an improved transcription of a gene compared with an inherently existing wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Examples of stronger promoters usable in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12): 8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" can mean a SD sequence that provides an improved translation of mRNA compared with the inherent wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a more frequently used synonymous codon. That is, the gene to be introduced may be modified, for example, so as to contain optimal codons according to the frequencies of codons observed in a host to be used. Codons can be replaced by, for example, the site-specific mutation method. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the protein. Enhancement of the specific activity also includes desensitization to feedback inhibition. That is, when a protein is subject to feedback inhibition by a metabolite, the activity of the protein can be increased by making the bacterium harbor a gene encoding a mutant protein that has been desensitized to the feedback inhibition. The term "desensitization to feedback inhibition" can include complete elimination of the feedback inhibition, and attenuation of the feedback inhibition, unless otherwise stated. Also, a state of "being desensitized to feedback inhibition", i.e. a state that feedback inhibition is eliminated or attenuated, may also be referred to as "tolerant to feedback inhibition". A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1997, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may be increased to, for example, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may be increased to, for example, 1.5 times or more, 2 times or more, or 3 times or more of that of a non-modified strain.

The aforementioned methods for increasing the activity of a protein can be used for enhancement of the activities of arbitrary proteins such as L-amino acid biosynthesis enzymes, and enhancement of the expression of arbitrary genes such as genes encoding those arbitrary proteins, besides enhancement of carotenoid biosynthesis enzyme activity.

<1-4> Method for Reducing Activity of Protein

Hereinafter, the methods for reducing the activity of a protein will be explained.

The expression "the activity of a protein is reduced" can mean that the activity of the protein is reduced as compared with a non-modified strain. Specifically, the expression "the activity of a protein is reduced" may mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parent strain. Specific examples of the non-modified strain can include the respective type strains of the species of microorganisms. Specific examples of the non-modified strain also can include strains exemplified above in relation to the description of microorganisms. That is, in an embodiment, the activity of a protein may be reduced as compared with a type strain, i.e. the type strain of the species to which the microorganism as described herein belongs. In another embodiment, the activity of a protein may also be reduced as compared with the *E. coli* MG1655 strain. In another embodiment, the activity of a protein may also be reduced as compared with the *P. ananatis* AJ13355 strain. In another embodiment, the activity of a protein may also be reduced as compared with the *C. glutamicum* ATCC 13869 strain. The state that "the activity of a protein is reduced" also can include a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression of the gene is reduced as compared with a non-modified strain such as a wild-type strain and parent strain. Specifically, the expression "the expression of a gene is reduced" may mean that the expression of the gene per cell is reduced as compared with that of a non-modified strain such as a wild-type strain and parent strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also can include a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence are modified. The transcription efficiency of a gene can be reduced by, for example, replacing the promoter of the gene on a chromosome with a weaker promoter. The term "weaker promoter" can mean a promoter providing an attenuated transcription of a gene compared with an inherent wild-type promoter of the gene. Examples of weaker promoters can include, for example, inducible promoters. That is, an inducible promoter may function as a weaker promoter under a non-induced condition, such as in the absence of the corresponding inducer. Furthermore, a part or the whole of an expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The state that "a protein that normally functions is not produced" can include a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" can refer to deletion of a partial or the entire region of the coding region of the gene. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, the reading frames of the sequences upstream and downstream from the region to be deleted do not have to be the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. The reading frames of the sequences upstream and downstream from the insertion site do not have to be the same. The other sequence is not particularly limited so long as a sequence that reduces or eliminates the activity of the encoded protein is chosen, and examples thereof can include, for example, a marker gene such as antibiotic resistance genes, and a gene useful for production of an objective substance.

Such modification of a gene on a chromosome as described above can be attained by, for example, preparing a deficient type gene modified so that it is unable to produce a protein that normally functions, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easier. Examples of the deficient-type gene can include a gene including deletion of all or a part of the gene, gene including a missense mutation, gene including a nonsense mutation, gene including a frame shift mutation, and gene including insertion of a transposon or marker gene. The protein encoded by the deficient-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex that is made up of a plurality of subunits, some or all of the subunits may be modified, so long as the activity of the protein is eventually reduced. That is, for example, some or all of the genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein as mentioned above can be applied to reduction in the activities of arbitrary proteins such as an enzyme that catalyzes a reaction branching away from the biosynthesis pathway of an objective L-amino acid to generate a compound other than the objective L-amino acid, and reduction in the expression of arbitrary genes such as genes encoding those arbitrary proteins.

<2> Method

<2-1> Method for Producing L-Amino Acid

An embodiment of the method as described herein (also referred to as "first embodiment of the method") is a method for producing an L-amino acid including the steps of culturing the bacterium as described herein in a medium (a culture medium) to accumulate an L-amino acid in the medium, and collecting the L-amino acid from the medium. In the first embodiment of the method, one kind of L-amino acid may be produced, or two or more kinds of L-amino acids may be produced.

The medium is not particularly limited, so long as the bacterium as described herein can proliferate in it, and an objective L-amino acid can be produced. As the medium, for example, a usual medium used for culture of bacteria such as coryneform bacteria and Enterobacteriaceae bacteria can be used. As the medium, for example, a medium containing carbon source, nitrogen source, phosphorus source, and sulfur source, as well as components selected from other various organic components and inorganic components as required can be used. Types and concentrations of the medium components can be appropriately determined according to various conditions such as the type of chosen bacterium.

Specific examples of the carbon source can include, for example, saccharides such as glucose, fructose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, and aliphatic acids. As the carbon source, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the bacterium as described herein. As the carbon source, a single kind of carbon source may be used, or two or more kinds of carbon sources may be used in combination.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source can include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Furthermore, when an auxotrophic mutant that requires an amino acid or the like for growth thereof is used, the required nutrient can be added to the medium. For example, in many of L-lysine-producing bacteria, the L-lysine biosynthetic pathway is enhanced and the L-lysine decomposition ability is attenuated. When such an L-lysine-producing bacterium is cultured, for example, L-threonine, L-homoserine, L-isoleucine, and/or L-methionine can be added to the medium.

Furthermore, the amount of biotin can be restricted in the medium, or a surfactant or penicillin can be added to the medium.

The culture conditions are not particularly limited so long as the bacterium as described herein can proliferate, and an objective L-amino acid can be produced. The culture can be performed, for example, under usual conditions used for culturing bacteria such as coryneform bacteria and Enterobacteriaceae bacteria. The culture conditions can be appropriately set according to various conditions such as the type of bacterium that is chosen.

The culture can be performed by using a liquid medium. At the time of the culture, the bacterium cultured on a solid medium such as agar medium may be directly inoculated into a liquid medium, or the bacterium cultured in a liquid medium as seed culture may be inoculated into a liquid medium for main culture. That is, the culture may be performed separately as seed culture and main culture. In such a case, the culture conditions of the seed culture and the main culture may be or may not be the same. Amount of the bacterium contained in the medium at the time of the start of the culture is not particularly limited. The main culture may be performed by, for example, inoculating a seed culture broth to a medium for main culture at an amount of 1 to 50% (v/v).

The culture can be performed as batch culture, fed-batch culture, continuous culture, or a combination of these. The medium used at the time of the start of the culture can also be referred to as "starting medium". The medium supplied to a culture system (fermentation tank) in fed-batch culture or continuous culture can also be referred to as "feed medium". Furthermore, to supply a feed medium to a culture system in fed-batch culture or continuous culture can also be referred to as to "feed". Furthermore, when the culture is performed separately as seed culture and main culture, for example, both the seed culture and the main culture may be performed as batch culture. Alternatively, for example, the seed culture may be performed as batch culture, and the main culture may be performed as fed-batch culture or continuous culture.

The medium components may be present in the starting medium, feed medium, or both. The components present in the starting medium may be or may not be the same as the components present in the feed medium. The concentration of each component present in the starting medium may be or may not be the same as the concentration of the component present in the feed medium. Furthermore, two or more kinds of feed media containing different types and/or different concentrations of components may be used. For example, when medium is intermittently fed a plurality of times, the types and/or concentrations of components contained in the feed media may be or may not be the same for each feeding.

The concentration of the carbon source in the medium is not particularly limited, so long as the bacterium can proliferate and produce an L-amino acid. The concentration of the carbon source in the medium may be as high as possible within such a range that production of the L-amino acid is not inhibited. The concentration of the carbon source in the medium may be, as the initial concentration (the concentration in the starting medium), for example, 1 to 30% (w/v), or 3 to 10% (w/v). Furthermore, the carbon source may be additionally supplied to the medium as required. For example, the carbon source may be additionally supplied to the medium in proportion to consumption of the carbon source accompanying progress of the fermentation.

The culture can be performed, for example, under an aerobic condition. The term "aerobic condition" can refer to when the dissolved oxygen concentration in the liquid medium is not lower than 0.33 ppm, which is the detection limit for the detection with an oxygen membrane electrode, or may be when the dissolved oxygen concentration in the liquid medium is not lower than 1.5 ppm. The oxygen concentration can be controlled to, for example, 5 to 50%, or about 10%, of the saturated oxygen concentration. Specifically, the culture under an aerobic condition can be performed by aeration culture, shaking culture, stirring culture, or a combination thereof. The pH of the medium may be, for example, 3 to 10, or 4.0 to 9.5. During the culture, the pH of the medium can be adjusted as required. The pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 40° C., or 25 to 37° C. The culture period may be, for example, 10 to 120 hours. The culture may be continued, for example, until the carbon source contained in the medium is consumed, or until the bacterium loses the activity. By culturing the bacterium as described herein under such conditions as described above, an L-amino acid is accumulated in the medium.

For producing a basic amino acid such as L-lysine, the culture step, also called the fermentation step, may be carried out so that bicarbonate ions and/or carbonate ions serve as counter ions for the basic amino acid. Such a fermentation mode can also be referred to as "carbonate fermentation". By the carbonate fermentation, a basic amino acid can be produced by fermentation while reducing the amounts of sulfate ions and/or chloride ions to be used, which have been conventionally used as counter ions for a basic amino acid.

The carbonate fermentation can be carried out, for example, as described in US2002-0025564A, EP1813677A, and Japanese Patent Laid-open (Kokai) No. 2002-65287.

Specifically, the carbonate fermentation can be carried out so that, for example, there is a culture period where 20 mM or more, 30 mM or more, or 40 mM or more, of bicarbonate ions and/or carbonate ions are present in the medium. The above-exemplified concentrations each are interpreted as the total concentration of bicarbonate ions and carbonate ions. The phrase "there is a culture period where bicarbonate ions and/or carbonate ions are present in a medium at a certain concentration" can mean that bicarbonate ions and/or carbonate ions are present in the medium at the certain concentration during at least a partial period of culture. That is, bicarbonate ions and/or carbonate ions may be present in the medium at the above-exemplified concentration over the whole period of culture or during a partial period of culture. The "partial period" is not particularly limited so long as a desired productivity of the basic amino acid is attained. The "partial period" may be, for example, a period of 10% or more, 20% or more, 30% or more, 50% or more, 70% or more, or 90% or more of that of the whole period of culture. When the culture is performed separately as seed culture and main culture, the term "whole period of culture" can refer to the whole period of the main culture. Bicarbonate ions and/or carbonate ions can be present in the medium at the above-exemplified concentration while the basic amino acid is produced. That is, for example, when the culture step includes a stage of proliferating the basic amino acid-producing bacterium (growth period) and a stage of producing the basic amino acid (production period), the bicarbonate ions and/or carbonate ions can be present in the medium at the above-exemplified concentration at least during the production period. The term "growth period" can refer to a period where the carbon source is utilized mainly for cell growth, and may specifically refer to a period until the time point of 3 hr, 6 hr, or 10 hr after the start of culture. The term "production period" can refer to a period where the carbon source is utilized mainly for production of a substance, and may specifically refer to a period from the time point of 3 hr, 6 hr, or 10 hr after the start of culture.

Bicarbonate ions and/or carbonate ions can be maintained in the medium by controlling the internal pressure of the fermentation tank to be positive, supplying carbon dioxide gas into the medium, or a combination thereof. The internal pressure of the fermentation tank during fermentation can be controlled to be positive by, for example, making the gas supply pressure higher than the exhaust pressure. If the internal pressure of the fermentation tank is controlled to be positive, the carbon dioxide gas generated by fermentation dissolves in the medium to generate bicarbonate ions and/or carbonate ions, and these can serve as counter ions for the basic amino acid. The internal pressure of the fermentation tank may specifically be, for example, 0.03 to 0.2 MPa, 0.05 to 0.15 MPa, or 0.1 to 0.3 MPa, in terms of the gage pressure (pressure difference with respect to the atmospheric pressure). Carbon dioxide gas can be supplied to the medium by, for example, bubbling pure carbon dioxide gas or a mixed gas containing carbon dioxide gas into the medium. Examples of the mixed gas containing carbon dioxide gas can include a mixed gas containing 5 volume % or more of carbon dioxide gas. The internal pressure in the fermentation tank, supply volume of carbon dioxide gas, and limited aeration volume can be appropriately set according to various conditions such as pH of the medium, bicarbonate and/or carbonate ion concentration in the medium, and ammonia concentration in the medium.

In conventional methods for producing a basic amino acid, a sufficient amount of ammonium sulfate and/or ammonium chloride is usually added to the medium as a source of counter ions for the basic amino acid, or sulfuric acid decomposition products and/or hydrochloric acid decomposition products of proteins etc. as nutrient components are added to the medium. Therefore, large amounts of sulfate ions and/or chloride ions are present in the medium, and the concentration of the weakly acidic carbonate ions is extremely low, i.e., it is at a ppm order.

On the other hand, the carbonate fermentation is characterized in that the amounts of sulfate ions and/or chloride ions to be used are reduced so that carbon dioxide gas released by a bacterium during fermentation and/or carbon dioxide gas externally supplied is dissolved in the medium, and used as counter ions for the basic amino acid. That is, in the carbonate fermentation, one of the objects is to reduce the amounts of sulfate ions and/or chloride ions to be used, and therefore, it is not necessary to add sulfate ions or chloride ions to the medium in an amount larger than that required for growth of the basic amino acid-producing bacterium. The ammonium sulfate or the like can be fed to the medium at an early stage of the culture at an amount required for growth, and the feeding is terminated in the middle of the culture. Alternatively, ammonium sulfate or the like may be fed to the medium while maintaining the balance with respect to the amounts of carbonate ions and/or bicarbonate ions dissolved in the medium. By reducing the amounts of sulfate ions and/or chloride ions, the concentrations of sulfate ions and/or chloride ions in the medium can be lowered. By lowering the concentrations of sulfate ions and/or chloride ions, the presence of bicarbonate ions and/or carbonate ions can induced more easily in the medium. That is, in the carbonate fermentation, the pH of the medium for inducing the presence of bicarbonate ions and/or carbonate ions in the medium in an amount required to act as the counter ions for the basic amino acid can be suppressed to be lower compared with the conventional methods. The total molar concentration of sulfate ions and chloride ions contained in the medium may specifically be, for example, 900 mM or lower, 700 mM or lower, 500 mM or lower, 300 mM or lower, 200 mM or lower, or 100 mM or lower.

In the carbonate fermentation, the pH of the medium is not particularly limited so long as bicarbonate ions and/or carbonate ions are present in the medium at a desired concentration, and a desired productivity of the basic amino acid is attained. The pH of the medium can be appropriately set according to various conditions such as the type of bacterium to be used, bicarbonate and/or carbonate ion concentration in the medium, and ammonia concentration in the medium. The pH of the medium may be controlled to, for example, 6.5 to 9.0, or 7.2 to 9.0, during the culture. The pH of the medium may be controlled to the above-exemplified value during at least a partial period of culture. That is, the pH of the medium may be controlled to the above-exemplified value over the whole period of culture or during a partial period of culture. The descriptions concerning the culture period where bicarbonate ions and/or carbonate ions are present in a medium can be similarly applied to the "partial period" during which the pH of the medium is controlled. That is, for example, the pH of the medium may be controlled to the above-exemplified value during a period where the basic amino acid is produced. Furthermore, the pH of the medium may be, for example, 7.2 or higher, or 7.2 to 9.0, at the completion of culture. That is, the pH of the medium may be controlled so as to attain the above-exemplified value of pH at the completion of culture. The pH of the medium may be controlled, for example, directly by using the pH value per se as an indicator, or indirectly by controlling the total ammonia concentration (WO2006/038695).

Furthermore, the medium may contain anions other than bicarbonate ions and/or carbonate ions (also referred to as other anions). The concentrations of the other anions in the medium can be low so long as they are present in amounts required for growth of the basic amino acid-producing bacterium. Examples of the other anions can include chloride ions, sulfate ions, phosphate ions, organic acid ions, and hydroxide ions. The total molar concentration of these other anions may specifically be, for example, 900 mM or lower, 700 mM or lower, 500 mM or lower, 300 mM or lower, 200 mM or lower, 100 mM or lower, 50 mM or lower, or 20 mM or lower.

Furthermore, the medium may contain cations other than the basic amino acid (also referred to as other cations). Examples of the other cations can include K ions, Na ions, Mg ions, and Ca ions originating in medium components. The total molar concentration of the other cations may specifically be, for example, 50% or lower, 10% or lower, 5% or lower, or 2% or lower, of the molar concentration of the total cations.

In the carbonate fermentation, the total ammonia concentration in the medium can be controlled to be a concentration at which production of the basic amino acid is not inhibited (WO2006/038695, WO2015/050234). The term "total ammonia concentration" can refer to the total concentration of non-dissociated ammonia ($NH_3$) and ammonium ions ($NH_4^+$). Examples of the total ammonia concentration at which "production of the basic amino acid is not inhibited" can include, for example, a total ammonia concentration providing yield and/or productivity corresponding to 50% or more, 70% or more, or 90% or more, of the yield and/or productivity obtainable in the production of the basic amino acid under optimal conditions. The total ammonia concentration in the medium may specifically be, for example, 300 mM or lower, 250 mM or lower, 200 mM or lower, 100 mM or lower, or 50 mM or lower. The dissociation degree of ammonia decreases as the pH becomes higher. Non-dissociated ammonia is more toxic to bacteria compared with ammonium ions. Therefore, the upper limit of the total ammonia concentration also depends on the pH of the medium. That is, as the pH of the medium increases, the acceptable total ammonia concentration decreases. Therefore, the total ammonia concentration at which "production of the basic amino acid is not inhibited" can be determined for each specific pH value. However, the total ammonia concentration range that is acceptable at the highest pH level during the culture can be used as the total ammonia concentration range over the whole period of culture. The total ammonia concentration in the medium may be controlled to the above-exemplified concentration during at least a partial period of culture. That is, the total ammonia concentration in the medium may be controlled to the above-exemplified concentration over the whole period of culture or during a partial period of culture. The descriptions concerning the culture period where bicarbonate ions and/or carbonate ions are present in a medium can be similarly applied to the "partial period" during which the total ammonia concentration in the medium is controlled. That is, for example, the total ammonia concentration in the medium may be controlled to the above-exemplified concentration during a period where the basic amino acid is produced. Furthermore, specific examples of the "partial period" during which the total ammonia concentration in the medium can include a period during which the pH of the medium increases (e.g. the pH of the medium increases to 7.2 or higher) due to the shortage of counter ions such as sulfate ions and chloride ions with respect to accumulation of the basic amino acid.

The total concentration of ammonia as a source of nitrogen required for growth of the basic amino acid-producing bacterium and production of the basic amino acid is not particularly limited, and can be appropriately set, so long as depletion of ammonia does not continue during the culture, and decrease in the productivity of the basic amino acid due to the shortage of the nitrogen source does not occur. For example, the ammonia concentration can be measured over time during the culture, and if ammonia in the medium is depleted, a small amount of ammonia can be added to the medium. The ammonia concentration after the addition of ammonia may specifically be, for example, 1 mM or higher, 10 mM or higher, or 20 mM or higher, as the total ammonia concentration.

The total ammonia concentration in the medium can be controlled by, for example, using an apparatus for controlling ammonia and a method for controlling ammonia described in WO2015/050234.

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated can include, for example, pH 5.0 to 4.0, pH 4.5 to 4.0, pH 4.3 to 4.0, or around pH 4.0 (EP1078989A).

Production of an L-amino acid can be confirmed by known methods used for detection or identification of compounds. Examples of such methods can include, for example, HPLC, LC/MS, GC/MS, and NMR. These methods can be independently used, or can be used in an appropriate combination.

The produced L-amino acid can be collected (harvested) from the fermentation broth by known methods used for separation and purification of compounds. Examples of such methods can include, for example, ion-exchange resin method (Nagai, H. et al., Separation Science and Technology, 39(16), 3691-3710), precipitation, membrane separation (Japanese Patent Laid-open (Kokai) No. 9-164323 and Japanese Patent Laid-open (Kokai) No. 9-173792), and crystallization (WO2008/078448 and WO2008/078646). These methods can be independently used, or can be used in an appropriate combination. The L-amino acid to be collected may be a free compound, a salt thereof, or a mixture thereof. Examples of the salt can include, for example, sulfate, hydrochloride, carbonate, ammonium salt, sodium salt, and potassium salt. When L-lysine is produced, L-lysine to be collected may specifically be, for example, free L-lysine, L-lysine sulfate, L-lysine hydrochloride, L-lysine carbonate, or a mixture of these. When L-glutamic acid is produced, L-glutamic acid to be collected may specifically be, for example, free L-glutamic acid, sodium L-glutamate (monosodium L-glutamate, MSG), ammonium L-glutamate (monoammonium L-glutamate), or a mixture of these. For example, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5). The monosodium L-glutamate crystal can be used as, for example, an umami seasoning. The monosodium L-glutamate crystal may also be used as a seasoning in combination with a nucleic acid such as sodium guanylate and sodium inosinate, which also have umami taste.

When the L-amino acid is precipitated in the medium, it can be collected by centrifugation, filtration, or the like. The L-amino acid precipitated in the medium may also be isolated together with the L-amino acid dissolving in the medium, after the L-amino acid dissolving in the medium is crystallized.

The collected L-amino acid may contain such components as bacterial cells, medium components, moisture, and by-product metabolites of the bacterium in addition to the L-amino acid. The collected L-amino acid may also be purified to a desired extent. Purity of the collected L-amino acid may be, for example, 50% (w/w) or higher, 85% (w/w) or higher, or 95% (w/w) or higher (JP1214636B, U.S. Pat. Nos. 5,431,933, 4,956,471, 4,777,051, 4,946,654, 5,840,358, 6,238,714, and US2005/0025878). The L-amino acid may also be provided as a dried granulated product containing the L-amino acid. For example, examples of methods for producing a dried granulated product containing L-lysine can include a method described in U.S. Pat. No. 7,416,740.

In addition, by culturing the bacterium under such conditions as described above, a carotenoid can be accumulated in cells of the bacterium. Specifically, when the bacterium has a carotenoid-producing ability, a carotenoid can be accumulated in cells of the bacterium by culturing the bacterium. One kind of carotenoid may be accumulated in cells of the bacterium, or two or more kinds of carotenoids may be accumulated in cells of the bacterium.

When a carotenoid is accumulated in cells of the bacterium, the cells (i.e. bacterial cells containing a carotenoid) can be collected. That is, the first embodiment of the method as described herein may further include collecting the cells (i.e. bacterial cells containing a carotenoid). That is, the first embodiment of the method as described herein can include a method for producing bacterial cells containing a carotenoid. Methods for collecting the cells from the fermentation broth are not particularly limited. The cells can be collected from the fermentation broth by known methods. Examples of methods for collecting the cells from the fermentation broth can include, for example, spontaneous precipitation, centrifugation, and filtration. These methods can be independently used, or can be used in an appropriate combination.

<2-2> Method for Producing Bacterial Cells Containing Carotenoid

As described above, when a carotenoid is accumulated in cells of the bacterium, bacterial cells containing the carotenoid can be obtained. That is, another embodiment of the method as described herein (also referred to as "second embodiment of the method") is a method for producing bacterial cells containing a carotenoid including the steps of culturing the bacterium as described herein having a carotenoid-producing ability in a medium to accumulate a carotenoid in cells of the bacterium, and collecting the cells of the bacterium. One kind of carotenoid may be accumulated in the cells, or two or more kinds of carotenoids may be accumulated in the cells.

Furthermore, the bacterium can have the ability to produce L-amino acids. Hence, in the second embodiment of the method as described herein, by culturing the bacterium as described herein, an L-amino acid can be accumulated in a medium. When an L-amino acid is accumulated in the medium, the L-amino acid can be collected (harvested). That is, the second embodiment of the method as described herein may further include a step of collecting the L-amino acid from the medium. That is, the second embodiment of the method as described herein can include a method for producing an L-amino acid. In the second embodiment as described herein, one kind of L-amino acid may be produced, or two or more kinds of L-amino acids may be produced.

Conditions for carrying out the second embodiment of the method as described herein, such as medium composition, culture conditions, and methods for collecting the cells, are not particularly limited so long as bacterial cells containing a carotenoid are obtained. The descriptions concerning the conditions for carrying out the first embodiment of the method as described herein can be similarly applied to the conditions for carrying out the second embodiment of the method as described herein.

In an embodiment, the first embodiment of the method as described herein and the second embodiment of the method as described herein may be identical to each other. Specifically, when both an L-amino acid and bacterial cells containing a carotenoid are produced in the first and second embodiments of the method as described herein, both the embodiments may be identical to each other.

<3> Bacterial Cells and Use of the Same

The bacterial cells as described herein can contain a carotenoid. The bacterial cells may be cells of the bacterium containing a carotenoid. Specifically, when the bacterium has a carotenoid-producing ability, cells of the bacterium can contain a carotenoid. That is, more specifically, the bacterial cells may be cells of a bacterium, wherein the cells contain a carotenoid, the bacterium has an L-amino acid-producing ability and a carotenoid-producing ability, and the bacterium has been modified so that the activity of a carotenoid biosynthesis enzyme is increased. The bacterial cells may contain one kind of carotenoid, or two or more kinds of carotenoids. The bacterial cells can be produced by, for example, culturing the bacterium and collecting (harvesting) the cells of the bacterium. That is, the bacterial cells can be produced by, for example, the method as described herein. The amount of the carotenoid in the cells can be measured according to the usual manner. The amount of the carotenoid present in the cells can be measured by, for example, the method described in the Examples section. The bacterial cells can be used in any form such as wet cells or dry cells.

The purpose of the bacterial cells is not particularly limited. The bacterial cells can be used for, for example, in the culturing (breeding) of organisms such as aquatic organisms. Examples of aquatic organisms can include, for example, fishes and crustaceans. Specific examples of aquatic organisms can include, for example, salmon, shrimp (prawn), and seabream. The term "salmon" collectively can refer to fishes belonging to the family Salmonidae. Specific examples of salmon can include, for example, chum salmon (*Oncorhynchus keta*), sockeye salmon (*Oncorhynchus nerka*), coho salmon (*Oncorhynchus kisutsh*), Atlantic salmon (*Salmo salar*), king salmon (*Oncorhynchus tshawytscha*), and rainbow trout (*Oncorhynchus mykiss*).

That is, the present invention provides a feed, such as a feed for an aquatic organism, containing the bacterial cells as described herein. This feed is also referred to as "feed as described herein".

The composition of the feed as described herein is not particularly limited, except that it contains the bacterial cells. The types and amounts of ingredients contained in the feed as described herein can be appropriately chosen according to various conditions such as the type and growth stage of the objective organism, and the usage scheme of the feed as described herein.

The feed as described herein may contain, for example, ingredient(s) similar to those contained in feeds such as usual feeds for aquatic organisms, in addition to the bacterial cells. Examples of such ingredient(s) can include animal feed ingredients, vegetable feed ingredients, and other various feed ingredients. Specific examples of the animal feed ingredients can include, for example, fish meal, fish soluble, powdered bone, and chicken meal. Specific examples of the vegetable feed ingredients can include, for example, cereal powder (wheat flour etc.), vegetable protein (wheat gluten, corn gluten, etc.), starch (cornstarch etc.), and vegetable oil meal (soybean meal etc.). Specific examples of the other ingredients can include, for example, amino acid fermentation meal (lysine fermentation meal, etc.), thickening agent (carboxymethylcellulose, alginic acid, etc.), yeast, eicosapentaenoic acid, and docosahexaenoic acid. Specific examples of the other ingredients also can include, for example, additives for fishery such as drugs for fishery, vitamins, and amino acids.

The amount of the bacterial cells present in the feed as described herein, for example, may be 1% (w/w) or more, 2% (w/w) or more, 3% (w/w) or more, 4% (w/w) or more, 5% (w/w) or more, 7% (w/w) or more, or 10% (w/w) or more, may be 50% (w/w) or less, 30% (w/w) or less, 20% (w/w) or less, 15% (w/w) or less, 10% (w/w) or less, 7% (w/w) or less, or 5% (w/w) or less, or may be within a range defined as a non-contradictory combination thereof, in terms of dry cell weight. Specifically, the amount of the bacterial cells present in the feed as described herein may be, for example, 1% (w/w) to 10% (w/w).

The amount of the bacterial cells present in the feed as described herein may also be, for example, such an amount that the amount of total carotenoids present in the feed as described herein comes to be within a predetermined range. The amount of total carotenoids present in the feed as described herein, for example, may be 2 mg/100 g or more, 3 mg/100 g or more, 4 mg/100 g or more, 5 mg/100 g or more, or 10 mg/100 g or more, may be 30 mg/100 g or less, 20 mg/100 g or less, 15 mg/100 g or less, 10 mg/100 g or less, or 5 mg/100 g or less, or may be within a range defined as a non-contradictory combination thereof. Specifically, the amount of total carotenoids present in the feed as described herein may be, for example, 2 mg/100 g to 10 mg/100 g.

The amount of the bacterial cells present in the feed as described herein may also be, for example, such an amount that the amount of astaxanthine present in the feed as described herein comes to be within a predetermined range. The amount of astaxanthine present in the feed as described herein, for example, may be 0.3 mg/100 g or more, 0.5 mg/100 g or more, 1 mg/100 g or more, 1.5 mg/100 g or more, 2 mg/100 g or more, or 3 mg/100 g or more, may be 20 mg/100 g or less, 15 mg/100 g or less, 10 mg/100 g or less, 5 mg/100 g or less, or 2 mg/100 g or less, or may be within a range defined as a non-contradictory combination thereof. Specifically, the amount of astaxanthine present in the feed as described herein may be, for example, 0.3 mg/100 g to 5 mg/100 g.

The feed as described herein can be produced by combining the bacterial cells and the other ingredient(s) so that the bacterial cells are present at a desired concentration in the feed. Methods for producing the feed as described herein are not particularly limited. For example, the feed as described herein can be produced by the same method as that for usual feeds for organisms using the same raw materials as those for usual feeds for organisms except that the bacterial cells are added (blended).

The form of the feed as described herein is not particularly limited, so long as it can be ingested by an objective organism. That is, the feed as described herein may be in any form such as powder, granule, crumble, pellet, cube, paste, and liquid. The feed as described herein may be produced in the form of, for example, a pellet such as dry pellet and moist pellet. The form of the feed as described herein can be appropriately chosen depending on various conditions such as the type and growth stage of the objective organism. For example, for fry, the feed in the form of powder or crumble can usually be used. For adult fish, dry pellets can usually be used.

The present invention also provides a composition for culturing (breeding) of an organism such as an aquatic organism, containing the bacterial cells as described herein. This composition is also referred to as "composition as described herein".

The composition as described herein is not particularly limited, except that it includes the bacterial cells as described herein. The types and amounts of ingredients contained in the composition as described herein can be appropriately chosen according to various conditions such as the type and growth stage of the objective organism, and the usage scheme of the composition as described herein.

The composition as described herein may include only the bacterial cells as described herein, or may contain one or more other ingredients. Examples of the other ingredients can include, for example, ingredients usually used for use in foods, feeds, drugs, and so forth. Specific examples of such ingredients can include, for example, additives such as excipients, binders, disintegrants, lubricants, stabilizers, flavoring agent, odor improving agents, perfumes, diluents, and surfactants. Specific examples of the other ingredients also can include, for example, such ingredients in the feed as described herein as described above other than the bacterial cells as described herein. That is, the composition as described herein may be constituted as a feed for an aquatic organism. That is, an embodiment of the composition as described herein may be such a composition as described herein as described above. The composition as described herein may be in any form such as powder, granule, crumble, pellet, cube, paste, and liquid.

The amount of the bacterial cells present in the composition as described herein, for example, may be 1% (w/w) or more, 2% (w/w) or more, 3% (w/w) or more, 4% (w/w) or more, 5% (w/w) or more, 7% (w/w) or more, or 10% (w/w) or more, may be 100% (w/w) or less, 99.9% (w/w) or less, 70% (w/w) or less, 50% (w/w) or less, 30% (w/w) or less, 20% (w/w) or less, 15% (w/w) or less, 10% (w/w) or less, 7% (w/w) or less, or 5% (w/w) or less, or may be within a range defined as a non-contradictory combination thereof, in terms of dry cell weight.

The composition as described herein may be used, for example, in combination with a feed such as a feed for an aquatic organism. The composition as described herein may be used in combination with a feed so that, for example, the amount of the bacterial cells, total carotenoids, or astaxanthine is such an amount of the bacterial cells, total carotenoids, or astaxanthine as described above in the feed as described herein. To such a feed, the descriptions concerning the feed as described herein mentioned above can be similarly applied. When the composition as described herein is constituted as a feed, the composition as described herein itself may be used as the feed as described herein.

A method for culturing an organism such as an aquatic organism is also described, including the step of feeding the bacterial cells as described herein to the organism. By culturing an organism, the organism can be produced. That is, the term "method for culturing an organism" may be synonymous to "method for producing an organism". By culturing an organism with feeding of the bacterial cells as described herein, the color tone of the organism can be improved. By culturing an organism with feeding of the bacterial cells as described herein, particularly, the reddish color of the organism can be enhanced. That is, the organism to be produced may be an organism having an improved color tone, or may particularly be an organism having an enhanced reddish color. The color tone and reddish color may be, for example, color tone and reddish color inside of the organism, such as those of fresh, or color tone and reddish color outside of the organism, such as those of scale or exoskeleton. Specifically, the color tone and reddish color may be improved or enhanced as compared with cases of feeding of a usual feed (i.e. a feed not added with the bacterial cells as described herein or a carotenoid).

The bacterial cells as described herein can be fed to an organism by, for example, utilizing the feed as described herein (namely, by feeding the feed as described herein). The expression "to feed the feed as described herein" can include not only to feed the feed as described herein prepared beforehand, but also to feed the bacterial cells as described herein and other ingredient(s) in combination so that they satisfy the requirement(s) of the feed as described herein described above. For example, the bacterial cells for addition and a feed before addition of the bacterial cells as described herein may be separately provided, and fed as a mixture prepared before or at the time of feeding, or fed separately. The feeding amount of the bacterial cells can be chosen so that, for example, the amount of the bacterial cells, total carotenoids, or astaxanthine is such an amount of the bacterial cells, total carotenoids, or astaxanthine as described above in the feed as described herein.

The amount of feed that is fed can be appropriately chosen according to various conditions such as the type of the objective organism. The amount of feed may be, for example, the satiation amount. The feed may be fed once a day, or two or more times a day as divided portions. The feed may also be fed once over several days. The amount of the feed fed at the time of each feeding may or may not be constant in terms of the amount of the bacterial cells, total carotenoids, or astaxanthine. The amount of the bacterial cells, total carotenoids, or astaxanthine in the feed as described herein at the time of each feeding may or may not be constant.

The feeding period can be appropriately chosen according to various conditions such as the type of the objective organism. The feed may be continuously fed over the entire period of culturing (breeding), or may be fed only in a partial period of culturing (breeding). The term "partial period" may refer to, for example, a period consisting of 10% or more, 20% or more, 30% or more, 50% or more, 70% or more, or 90% or more of the entire period of culturing (breeding). The period of feeding of the feed as described herein, for example, may be 3 days or longer, one week or longer, 2 weeks or longer, 3 weeks or longer, 4 weeks or longer, 2 months or longer, or 3 months or longer, may be one year or shorter, 6 months or shorter, 4 months or shorter, 3 months or shorter, 2 months or shorter, 4 weeks or shorter, or 3 weeks or shorter, or may be within a range defined by any uncontradictory combination of these ranges. Specifically, the period of feeding of the feed may be, for example, 2 weeks to 6 months. Feeding of the feed may be repeatedly continued and interrupted for arbitrary periods and with arbitrary intervals.

Cultivation (breeding) of an organism can be performed by the same method as usual methods for culturing (breeding) organisms except that the feed is fed. The culturing (breeding) of aquatic organisms can be performed in, for example, a fish pen in the sea or fish tank on land. The term "culturing" can include propagation culturing in which only production of seed organism (fry production etc.) is performed, and culturing for production of adult organism (parent fish etc.).

Similarly, the bacterial cells can be fed to an organism by, for example, using the composition as described herein (namely, by feeding the composition as described herein). The composition can be fed to an organism, for example, independently or together with a feed. The descriptions concerning the feeding scheme of the feed described above can be similarly applied to feeding scheme of the composition. That is, the composition as described herein can be fed, for example, together with a feed so that the amount of the bacterial cells, total carotenoids, or astaxanthine is such that a amount of the bacterial cells, total carotenoids, or astaxanthine as described above is present in the feed.

Such descriptions concerning the feeding scheme described above may be similarly applied to any other case of feeding the bacterial cells as described herein.

EXAMPLES

Hereinafter, the present invention will be more specifically explained with reference to the following non-limiting examples.

Example 1: L-Lysine Production and Carotenoid Accumulation Using E. coli Strain Having Enhanced Expression of Carotenoid Biosynthesis Enzyme Genes (1)

In this Example, L-lysine was produced by using an L-lysine-producing strain of E. coli into which carotenoid biosynthesis enzyme genes (crtEYIB) had been introduced, and the effect of an enhanced expression of carotenoid biosynthesis enzyme genes on L-lysine production and carotenoid accumulation was evaluated.

(1) Materials
Materials used in this Example are as follows.

TABLE 1

<Strains used>

| Strain | Description |
|---|---|
| *Escherichia coli* | |
| MG1655 | ATCC 47076, a wild-type strain |
| WC196LC | FERM BP-11027, also referred to as WC196ΔcadAΔldc, a model strain for L-lysine production |
| WC196LC_crtEYIB | WC196LCΔargT::$P_{tac}$_crtEYIB_Km$^r$ (present application) |
| *Pantoea ananatis* | |
| SC17(0) | VKPM B-9246 |
| SC17(0)::Ptac-kdp | A strain corresponding to *P. ananatis* SC17(0) except that λattL_Km$^r$_λattR_$P_{tac}$ sequence has been inserted into an upstream portion of kdp operon (WO2008/090770) |
| SC17(0)ΔcrtEX::$P_{tac}$_crtE_Km$^r$ | A strain corresponding to *P. ananatis* SC17(0) except that crtX gene has been deleted and the promoter of crtE gene has been replaced with tac promoter (present application) |

TABLE 2

<Primers used>

| Primer | SEQ ID NO | Nucleotide Sequence (5'→3') |
|---|---|---|
| crtE-attL-F | 1 | ccgcatctttcgcgttgccgtaaatgtatccgtttataag gacagcccgatgaagcctgcttttttatactaagttggca |
| crtE-Ptac407X-R | 2 | gtgttttttgcgcagaccgtcatggcagtctccttgtgt gaaattgttatccg |
| Ptac407X-crtE-F | 3 | cggataacaatttcacacaaggagacttgccatgacggtc tgcgcaaaaaaacac |
| crtY-SD-crtE-R | 4 | cgcgagtccagcccccacgagaatcagatcataatgcggt tgcatagccgtctcctgtcgattaactgacggcagcgagt |
| argT_attL_fw | 5 | cacaacacaatacacaacataaaaaagccattttcacttg agggttatgttgaagcctgcttttttatactaagttggca |
| argT_crtB_rv | 6 | ggcgtgcaccatgatgatcattccatcaggtacagcttcc cagcgacgtactagagcgggcgctgccagagatgcgcagg |

<Medium Composition>

LB medium: 10 g/L Bacto tryptone, 5 g/L yeast extract, 5 g/L NaCl, pH 7.0 (adjusted with NaOH). Agar (15 g/L) was further present in the case of an agar medium.

LBGM9 medium: the composition of LB medium was added with a minimal medium components (5 g/L glucose, 2 mM magnesium sulfate, 3 g/L potassium dihydrogen phosphate, 0.5 g/L sodium chloride, 1 g/L ammonium chloride, 6 g/L disodium hydrogen phosphate), pH 7.0 (adjusted with KOH). Agar (15 g/L) was further present in the case of an agar medium.

MS medium: 40 g/L glucose, 1 g/L MgSO$_4$.7H$_2$O, 24 g/L (NH$_4$)$_2$SO$_4$, 1 g/L KH$_2$PO$_4$, 2 g/L yeast extract, 10 mg/L FeSO$_4$.7H$_2$O, 8 mg/L MnSO$_4$.5H$_2$O, pH 7.0 (adjusted with KOH).

(2) Construction of Strains (2-1) Construction of *P. ananatis* SC17(0)ΔcrtEX::$P_{tac}$_crtE_Km$^r$ PCR was performed using the chromosomal DNA of the *P. ananatis* SC17(0)::Ptac-kdp strain (WO2008/090770) as the template, and primers crtE-attL-F and crtE-Ptac407X-R, to amplify a DNA fragment λattL_Km$^r$_λattR_$P_{tac}$ (WO2008/090770), which contains a kanamycin resistance gene added with λattL and λattR sequences at the respective ends and the tac promoter sequence. Separately, PCR was performed using the chromosomal DNA of the *P. ananatis* SC17(0) strain (VKPM B-9246) as the template, and primers Ptac407X-crtE-F and crtY-SD-crtE-R, to amplify a DNA fragment containing a crtE gene. The SC17(0) strain was deposited in Russian National Collection of Industrial Microorganisms (VKPM, FGUP GosNII Genetika, Russian Federation, 117545 Moscow, Pt Dorozhny proezd, 1) on Sep. 21, 2005 under the accession number VKPM B-9246. The PCRs were performed by using PrimeSTAR GXL polymerase (Takara Bio) according to the protocol attached to the enzyme. Cross-over PCR was performed using both the obtained DNA fragments as the template, and primers crtE-attL-F and crtY-SD-crtE-R, to obtain a DNA fragment λattL_Km$^r$_λattR_$P_{tac}$_crtE, which contains a nucleotide sequence consisting of the crtE gene sequence and the λattL_Km$^r$_λattR_$P_{tac}$ sequence ligated to the 5' end side of the crtE gene.

According to a previous report (WO2010/027022A1), the *P. ananatis* SC17(0) strain was transformed with λattL_Km$^r$_λattR_P$_{tac}$_crtE by the λ-red method (US2006-0160191A; Datsenko, K. A, and Wanner, B. L. Proc. Natl. Acad. Sci. USA. 97:6640-6645 (2000)), and transformants were selected on LBGM9 agar medium containing 40 µg/mL kanamycin. Among the obtained transformants, a strain in which the crtX gene on the crtEXYIB operon has been deleted and the promoter of crtE gene has been replaced with the tac promoter was designated as *P. ananatis* SC17(0)ΔcrtEX::P$_{tac}$_crtE_Km$^r$ strain.

(2-2) Construction of *E. coli* WC196LC_crtEYIB

PCR was performed using the DNA extracted from the *P. ananatis* SC17(0)ΔcrtEX::P$_{tac}$_crtE_Km$^r$ strain as the template, and primers argT_attL_fw and argT_crtB_rv, to amplify a DNA fragment λattL_Km$^r$_λattR_P$_{tac}$_crtEYIB, which contains a nucleotide sequence consisting of the λattL_Km$^r$_λattR_P$_{tac}$ sequence and the crtEYIB genes ligated to the downstream of the λattL_Km$^r$_λattR_P$_{tac}$ sequence.

According to a previous report, the *E. coli* MG1655 strain was transformed with λattL_Km$^r$_λattR_P$_{tac}$ crtEYIB by the λ-red method (US2006-0160191A; Datsenko, K. A, and Wanner, B. L. Proc. Natl. Acad. Sci. USA. 97:6640-6645 (2000)), and transformants were selected on LB agar medium containing 50 µg/mL kanamycin. Among the obtained transformants, a strain in which insertion of λattL_Km$^r$_λattR_P$_{tac}$ crtEYIB in the argT gene on the chromosome was confirmed was designated as *E. coli* MG1655ΔargT::P$_{tac}$_crtEYIB_Km$^r$ strain.

P1 transduction was performed using the *E. coli* MG1655ΔargT::P$_{tac}$_crtEYIB_Km$^r$ strain as the donor and an *E. coli* L-lysine-producing strain WC196LC (FERM BP-11027) as the recipient according to the usual manner, to obtain the *E. coli* WC196LCΔargT::P$_{tac}$_crtEYIB_Km$^r$ strain (hereinafter, referred to as WC196LC_crtEYIB strain), which has been introduced with carotenoid biosynthesis enzyme genes (crtEYIB).

(3) Extraction and Quantification of Carotenoids

The strains WC196LC and WC196LC_crtEYIB each were cultured on LB agar medium for 48 hr at 37° C. Cells were scraped off in an amount corresponding to about 8-cm diameter of the cultured plate, and suspended in 1 mL of sterilized water. A part of the obtained cell suspension was separated, and used for measuring dry cell weight. The remaining part of the cell suspension was centrifuged, and the obtained cells were re-suspended in an equal volume of ethanol. The cell suspension in ethanol was added with an equal volume of φ0.5 mm glass beads (YGBLA05, YASUI KIKAI), and then cells were disrupted by repeating a step consisting of treating for 30 sec at 2,700 rpm and thereafter leaving at rest for 30 sec by using Multi Beads Shocker® (YASUI KIKAI) for 20 cycles. The cell disruption product was centrifuged for 2 min at 20,000×g, to obtain a supernatant. The obtained supernatant was diluted twice with ethanol, and A450 was measured. The amount of carotenoids was calculated from the measured value of A450 according to the following formula (I) (Britton G., Geteral carotenoid methods., Methods. Enzymol., 111: 113-149 (1985)).

Amount of total carotenoids (µg/L)=$A$450×2/(2620×100)×1000×1000000     (I)

Results are shown in Table 3. While accumulation of carotenoids was not observed for the strain WC196LC, accumulation of carotenoids was observed for the strain WC1196LC_crtEYIB.

TABLE 3

Accumulated amount of carotenoids in *E. coli* L-lysine-producing bacterium

| Strain | Carotenoids (µg/g-DCW) |
|---|---|
| WC196LC | N.D. |
| WC196LC_crtEYIB | 21.6 ± 0.8 (n = 3) |

(4) L-Lysine Production Culture

The strains WC196LC and WC196LC_crtEYIB each were uniformly applied to LB agar medium, and cultured for 24 hr at 37° C. Cells were scraped off in an amount corresponding to about 1-cm square of the cultured plate, and suspended in 0.5 mL of physiological saline. The turbidity at a wavelength of 620 nm (OD620) was measured for the obtained cell suspension by using a spectrophotometer U-2800 (Hitachi High-Technologies). The cell suspension was inoculated into 20 mL of MS medium contained in a 500-mL-volume Sakaguchi flask so as to obtain a final OD620 of 0.15, and 0.6 g of Japanese Pharmacopeia CaCO$_3$ preliminarily sterilized by dry heating was added thereto. Culture was performed for about 48 hr at 37° C. with stirring at 120 rpm by using a reciprocal shaking culture apparatus. After completion of the culture, the amount of L-lysine accumulated in the medium and the amount of residual glucose in the medium were quantified by using a Biotech-analyzer AS-210 (SAKURA SI).

Figure 1:
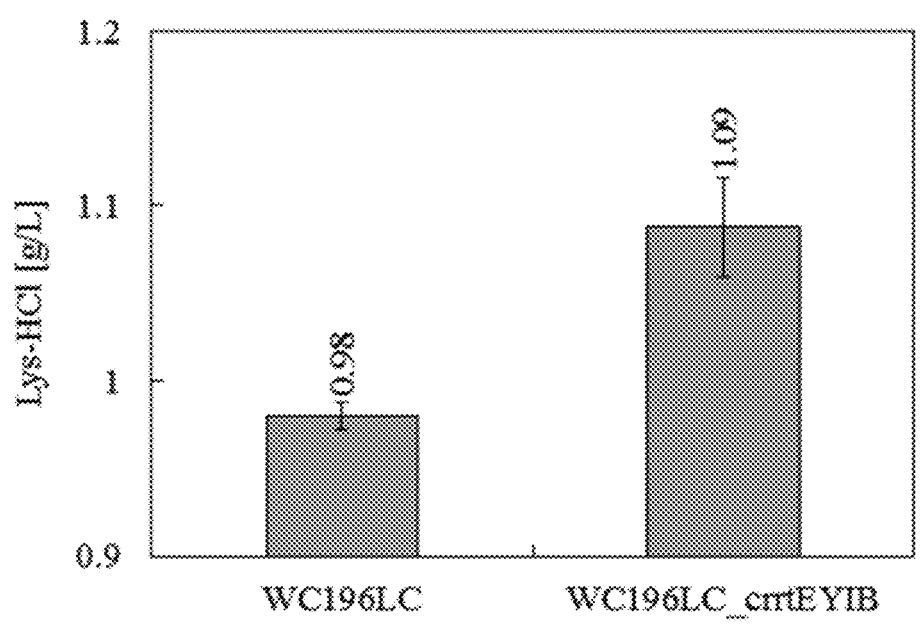
FIG. 1 shows a graph of the results of L-lysine production culture using an *E. coli* strain having an enhanced expression of carotenoid biosynthesis enzyme genes (crtEYIB) (n=6).

Results are shown in FIG. 1. The strain WC196LC_crtEYIB showed an improved L-lysine production as compared to the strain WC196LC.

Example 2: L-Lysine Production and Carotenoid Accumulation Using *E. coli* Strain Having Enhanced Expression of Carotenoid Biosynthesis Enzyme Genes (2)

In this Example, L-lysine production was performed by using an L-lysine-producing strain of *E. coli* introduced with carotenoid biosynthesis enzyme genes (crtZ and/or crtW as well as crtEYIB), and the effect of an enhanced expression of carotenoid biosynthesis enzyme genes on L-lysine production and carotenoid accumulation was evaluated.

(1) Construction of Strains (1-1) Introduction of crtZ Gene into *E. coli*

The crtZ genes derived from the *P. ananatis* SC17 strain, *Brevundimonas* sp. SD-212 strain, *Paracoccus* sp. N81106 strain, and *Alcaligenes* sp. were each introduced into the chromosome of the *E. coli* MG1655 strain as described below.

(1-1-1) Introduction of crtZ Gene of *P. ananatis* SC17 Strain

PCR was performed using the chromosomal DNA of the *P. ananatis* SC17 strain (FERM BP-11091) as the template, and primers CrtZ-FwP-tac40 and CrtZ-RvP (SEQ ID NOS: 31 and 32), to amplify a DNA fragment containing the crtZ gene (SEQ ID NO: 21). The SC17 strain was deposited at the independent administrative agency, National Institute of Advanced Industrial Science and Technology, International Patent Organism Depositary (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. Then, PCR was performed using the chromosomal DNA of the *P. ananatis* SC17(0)::Ptac-kdp strain as the template, and primers yhfK-crtZ-Fw1 and 71_Pa_rv (SEQ ID NOS: 34 and 35), to amplify a DNA fragment containing λattL_Km$^r$_λattR_P$_{tac}$ sequence. These two kinds of PCR products obtained above were purified, and then, PCR was performed using a mixture thereof as the template, and primers yhfK-crtZ-Fw1 and Pa_crtZ_yhfK_rv (SEQ ID NOS: 34 and 36), to obtain a fragment λattL_Km$^r$_λattR_P$_{4071}$_crtZ(Pa). The E. coli MG1655 strain was transformed with the obtained DNA fragment by the λ-red method, to obtain a strain MG1655ΔyhfK::P4071_crtZ(Pa), in which the crtZ gene derived from the P. ananatis SC17 strain was inserted into a yhfK gene region on the chromosome.

(1-1-2) Introduction of crtZ Gene of Brevundimonas sp. SD-212 Strain

The crtZ gene derived from the Brevundimonas sp. SD-212 strain (SEQ ID NO: 37) was totally-synthesized (Eurofins Genomics). PCR was performed using the obtained DNA fragment as the template, and primers 71_Bre212_crtZ_fw and Bre212_crtZ_yhfK_rv (SEQ ID NOS: 38 and 39), to amplify a DNA fragment containing the crtZ gene. Then, PCR was performed using the chromosomal DNA of the P. ananatis SC17(0)::Ptac-kdp strain as the template, and primers yhfK_P4071_fw and 71 Bre212_rv (SEQ ID NOS: 40 and 41), to amplify a DNA fragment containing λattL_Km$^r$_λattR_P$_{tac}$ sequence. These two kinds of PCR products obtained above were purified, and then, PCR was performed using a mixture thereof as the template, and primers yhfK_P4071_fw and Bre212_crtZ_yhfK_rv (SEQ ID NOS: 40 and 39), to obtain a fragment λattL_Km$^r$_λattR_P$_{4071}$_crtZ(Br). The E. coli MG1655 strain was transformed with the obtained DNA fragment by the λ-red method, to obtain a strain MG1655ΔyhfK::P4071_crtZ(Br), in which the crtZ gene derived from the Brevundimonas sp. SD-212 strain was inserted into a yhfK gene region on the chromosome.

(1-1-3) Introduction of crtZ Gene of Paracoccus sp. N81106 Strain

The crtZ gene derived from the Paracoccus sp. N81106 strain (SEQ ID NO: 42) was totally-synthesized (Eurofins Genomics). PCR was performed using the obtained DNA fragment as the template, and primers 71_Pc_crtZ_fw and Pc_crtZ_yhfK_rv (SEQ ID NOS: 43 and 44), to amplify a DNA fragment containing the crtZ gene. Then, PCR was performed using the chromosomal DNA of the P. ananatis SC17(0)::Ptac-kdp strain as the template, and primers yhfK_P4071_fw and 71 Pc_rv (SEQ ID NOS: 40 and 45), to amplify a DNA fragment containing λattL_Km$^r$_λattR_P$_{tac}$ sequence. These two kinds of PCR products obtained above were purified, and then, PCR was performed using a mixture thereof as the template, and primers yhfK_P4071_fw and Pc_crtZ_yhfK_rv (SEQ ID NOS: 40 and 44), to obtain a fragment λattL_Km$^r$_λattR_P$_{4071}$_crtZ(Pc). The E. coli MG1655 strain was transformed with the obtained DNA fragment by the λ-red method, to obtain a strain MG1655ΔyhfK::P4071_crtZ(Pc), in which the crtZ gene derived from the Paracoccus sp. N81106 strain was inserted into a yhfK gene region on the chromosome.

(1-1-4) Introduction of crtZ Gene of Alcaligenes sp.

The crtZ gene derived from the Alcaligenes sp. (SEQ ID NO: 46) was totally-synthesized (Eurofins Genomics). PCR was performed using the obtained DNA fragment as the template, and primers 71_Al_crtZ_fw and Al_crtZ_yhfK_rv (SEQ ID NOS: 47 and 48), to amplify a DNA fragment containing the crtZ gene. Then, PCR was performed using the chromosomal DNA of the P. ananatis SC17(0)::Ptac-kdp strain as the template, and primers yhfK_P4071_fw and 71_Al_rv (SEQ ID NOS: 40 and 49), to amplify a DNA fragment containing λattL_Km$^r$_λattR_P$_{tac}$ sequence. These two kinds of PCR products obtained above were purified, and then, PCR was performed using a mixture thereof as the template, and primers yhfK_P4071_fw and Al_crtZ_yhfK_rv (SEQ ID NOS: 40 and 48), to obtain a fragment λattL_Km$^r$_λattR_P$_{4071}$_crtZ(Al). The E. coli MG1655 strain was transformed with the obtained DNA fragment by the λ-red method, to obtain a strain MG1655ΔyhfK::P4071_crtZ(Al), in which the crtZ gene derived from the Alcaligenes sp. was inserted into a yhfK gene region on the chromosome.

(1-2) Construction of Plasmid pMIV-Pnlp8-crtW

The crtW gene derived from Nostoc punctiforme (codon-optimized for expression in E. coli; SEQ ID NO: 50) was totally-synthesized (Takara BIO). PCR was performed using the obtained DNA fragment as the template, and primers nlp-crtW-fw and nlp-crtW-Rv (SEQ ID NO: 51 and 52), to amplify a DNA fragment containing the crtW gene. Separately, PCR was performed using pMIV-Pnlp8 (Japanese Patent Laid-open (Kokai) No. 2010-187552) as the template, and primers pMIV-Pnlp8-Fw and pMIV-Rv (SEQ ID NO: 53 and 54), to amplify a vector fragment. These two kinds of obtained DNA fragments were mutually ligated by using In-Fusion® HD Cloning Kit (Takara BIO), to obtain pMIV-Pnlp8-crtW, an expression plasmid for the crtW gene derived from Nostoc punctiforme.

(1-3) Construction of Plasmid pMW_Ptac_crtW

A DNA (SEQ ID NO: 56) consisting of tac promoter sequence, the crtW gene derived from Brevundimonas aurantiaca, and rrnB terminator sequence ligated in this order was totally-synthesized (Eurofins Genomics). The obtained DNA was cloned between BamHI (5'-terminal side) and XbaI (3'-terminal side) of pMW219, to obtain pMW_Ptac_crtW, an expression plasmid for the crtW gene derived from B. aurantiaca.

(1-4) Introduction of crtZ Gene and crtW Gene into E. coli L-Lysine-Producing Bacterium Having Beta-Carotene-Producing Ability In order to remove the kanamycin resistance marker gene from the E. coli WC196LC_crtEYIB strain, which is an L-lysine-producing bacterium having beta-carotene-producing ability, the WC196LC_crtEYIB strain was transformed with pMW-int-xis (WO2007/037460 and Japanese Patent Laid-open (Kokai) No. 2005-058827) by the electroporation method. Transformants were selected by culturing on LB agar medium containing 50 mg/L ampicillin for 24 hr at 30° C. Obtained colonies of the transformants were subcultured on LB agar medium and cultured for 24 hr at 42° C. A strain sensitive to kanamycin and resistant to ampicillin was selected from obtained colonies, and designated as strain WC196LC_crtEYIB(ML).

Then, a P1 lysate was obtained from each of the strains MG1655ΔyhfK::P4071_crtZ(Pa), MG1655ΔyhfK::P4071_crtZ(Br), MG1655ΔyhfK::P4071_crtZ(Pc), and MG1655ΔyhfK::P4071_crtZ(Al), and P1 transduction was performed using the WC196LC_crtEYIB(ML) strain as the host. Transformants were selected by culturing on LB agar medium containing 40 mg/L kanamycin for 24 hr at 37° C. From the obtained transformants, there were obtained strains WC196LC_crtEYIB(ML)_ΔyhfK::P4071_crtZ(Pa), WC196LC_crtEYIB(ML)_ΔyhfK::P4071_crtZ(Br), WC196LC_crtEYIB(ML)_ΔyhfK::P4071_crtZ(Pc), and WC196LC_crtEYIB(ML)_ΔyhfK::P4071_crtZ(Al), in which the crtZ genes derived from the P. ananatis SC17 strain, Brevundimonas sp. SD-212 strain, Paracoccus sp.

N81106 strain, and *Alcaligenes* sp., respectively, were inserted into the chromosome.

Then, the WC196LC_crtEYIB(ML)_ΔyhfK::P4071_crtZ (Pa) strain was transformed with pMIV-Pnlp8-crtW and pMW_Ptac_crtW by the electroporation method, to obtain strains WC196LC_crtEYIB(ML)_ΔyhfK::P4071_crtZ(Pa)/pMIV-Pnlp8-crtW and WC196LC_crtEYIB(ML)_ΔyhfK::P4071_crtZ(Pa)/pMW_Ptac_crtW, respectively, into which the crtZ genes were introduced.

Similarly, the WC196LC strain was transformed with pMIV5JS (Japanese Patent Laid-open (Kokai) No. 2008-99668) and pMW219 by the electroporation method, to obtain vector control strains WC196LC/pMIV5JS and WC196LC/pMW219, respectively.

Hereinafter, unless otherwise stated, strains having plasmids were cultured using a medium added with the following antibiotic: 25 mg/L chloramphenicol for strains having pMIV5JS and pMIV-Pnlp8-crtW, and 50 mg/L kanamycin for strains having pMW219 and pMW_Ptac_crtW.

(2) Extraction and Quantification of Carotenoids

Carotenoids were extracted from bacterial cells with ethanol, and quantified by using HPLC. The procedure is described below.

Each strain was cultured on LB agar medium for 48 hr at 37° C. Cells were scraped off in an amount corresponding to about 8-cm diameter of the cultured plate, and suspended in 1 mL of sterilized water. A part of the obtained cell suspension was separated, and used for measuring dry cell weight. The remaining part of the cell suspension was also centrifuged, and the obtained cells were re-suspended in an equal volume of ethanol. The cell suspension in ethanol was added with an equal volume of φ0.5 mm glass beads (YGBLA05, YASUI KIKAI), and then cells were disrupted by repeating a step consisting of treating for 30 sec at 2,700 rpm and thereafter leaving at rest for 30 sec by using Multi Beads Shocker® (YASUI KIKAI) for 20 cycles. The cell disruption product was centrifuged for 2 min at 20,000×g, to obtain a supernatant. The obtained supernatant was subjected to HPLC, to quantify the amount of carotenoids. The conditions of HPLC were as follows:

UHPLC system: solvent delivery unit LC-30AD, autosampler SIL-30AC, degasser DGU-20A5R, column oven CTO-20AC, and detector SPD-20A UV-VIS (Shimadzu Corporation);

Column: phenomenex kinetex 2.6 µm C18 100A 75×4.6 mm (Shimadzu Corporation);

Analysis conditions:

Mobile phase, (A) Acetonitrile/$H_2O$/Formate (43/5/2), (B) Ethyl acetate/Formate (24/1);

Gradient, 0.0 min, 0% B, 0.0-6.0 min, to 100% B, 6.0 min-7.4 min, 100% B, 7.4-9.2 min, to 0% B, 9.2-10 min, 0% B;

Flow rate, 2.0 mL/min;

Column temperature, 30° C.

(3) L-Lysine Production Culture

Each strain was uniformly applied to LB agar medium, and cultured for 24 hr at 37° C. Cells were scraped off in an amount corresponding to about 1-cm square of the cultured plate, and suspended in 1 mL of physiological saline. The turbidity at a wavelength of 620 nm (OD620) was measured for the obtained cell suspension by using a spectrophotometer U-2800 (Hitachi High-Technologies). The cell suspension was inoculated into 20 mL of MS medium contained in a 500-mL-volume Sakaguchi flask so as to obtain a final OD620 of 0.126, and 0.6 g of Japanese Pharmacopeia $CaCO_3$ preliminarily sterilized by dry heating was added thereto. Culture was performed for about 48 hr at 37° C. with stirring at 120 rpm by using a reciprocal shaking culture apparatus. After completion of the culture, the amount of L-lysine accumulated in the medium and the amount of residual glucose in the medium were quantified by using a Biotech-analyzer AS-210 (SAKURA SI).

(4) Results (4-1) Effect of Introduction of crtZ Gene

Figure 2A:
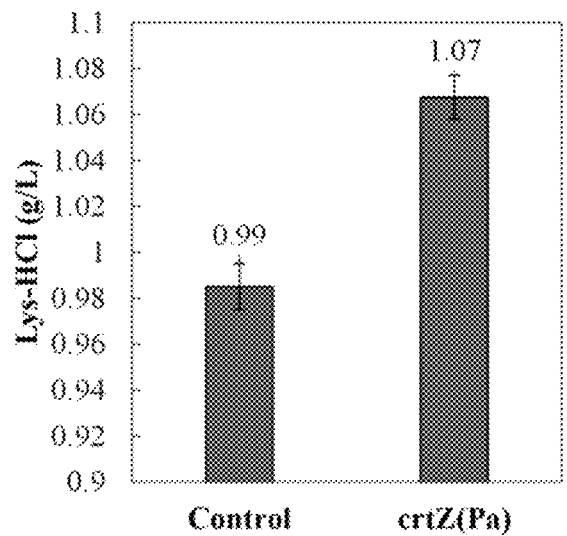
FIGS. 2A and 2B shows graphs of the results of L-lysine production culture using *E. coli* strains having an enhanced expression of carotenoid biosynthesis enzyme genes (crtEYIB and crtZ) (n=3)
Figure 2B:
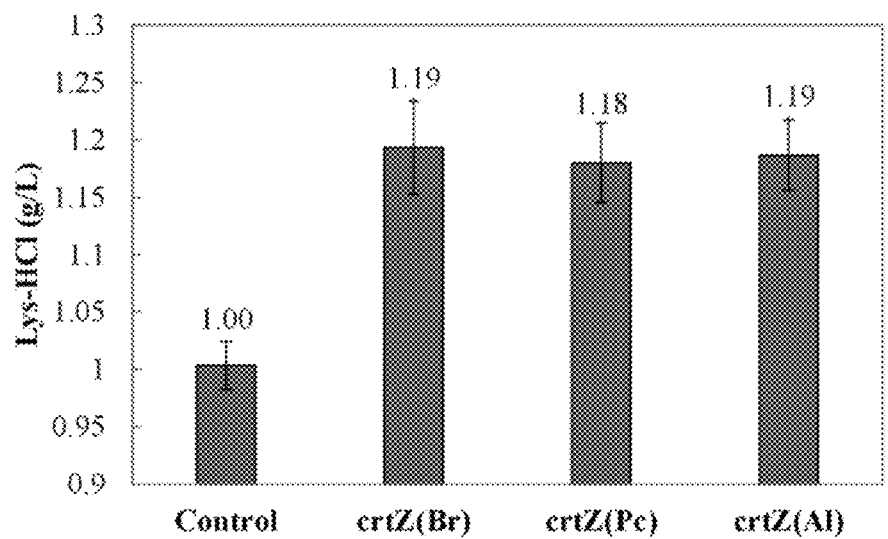

As a result of extraction and quantification of carotenoids, accumulation of zeaxanthin was confirmed in the strains introduced with crtEYIB genes and crtZ gene (Table 4). In addition, as a result of L-lysine production culture, the strains introduced with crtEYIB genes and crtZ gene each showed an improved L-lysine accumulation as compared to the control strain WC196LC (FIG. 2).

TABLE 4

Accumulated amount of carotenoids in *E. coli* L-lysine-producing bacterium

| Strain | Zeaxanthin (µg/g-DCW) | Astaxanthin (µg/g-DCW) |
| --- | --- | --- |
| WC196LC | N.D. | N.D. |
| WC196LC_crtEYIB(ML)_ΔyhfK::P4071_crtZ(Pa) | 34.3 ± 4.7 | N.D. |
| WC196LC_crtEYIB(ML)_ΔyhfK::P4071_crtZ(Br) | 16.2 ± 0.6 | N.D. |
| WC196LC_crtEYIB(ML)_ΔyhfK::P4071_crtZ(Pc) | 17.1 ± 1.6 | N.D. |
| WC196LC_crtEYIB(ML)_ΔyhfK::P4071_crtZ(Al) | 20.9 ± 1.4 | N.D. |

N.D., Not Detected.

(4-2) Effect of Introduction of crtW Gene

As a result of extraction and quantification of carotenoids, accumulation of astaxanthin was confirmed in the strains introduced with crtW gene as well as crtEYIB genes and crtZ gene (Table 5). In addition, as a result of L-lysine production culture, the strains introduced with crtW gene as well as crtEYIB genes and crtZ gene each showed an improved L-lysine accumulation as compared to the corresponding vector control strain (FIG. 3).

TABLE 5

Accumulated amount of carotenoids in *E. coli* L-lysine-producing bacterium (n = 3)

| Strain | Zeaxanthin (μg/g-DCW) | Astaxanthin (μg/g-DCW) |
|---|---|---|
| WC196LC/pMIV5JS | N.D. | N.D. |
| WC196LC_crtEYIB(ML)_ΔyhfK::P4071_crtZ(Pa)/pMIV-Pnlp8-crtW | 13.2 ± 1.1 | 25.4 ± 4.9 |
| WC196LC/pMW219 | N.D. | N.D. |
| WC196LC_crtEYIB(ML)_ΔyhfK::P4071_crtZ(Pa)/pMW_Ptac_crtW | N.D. | 28.6 ± 3.0 |

N.D., Not Detected.

Example 3: L-Threonine Production and Carotenoid Accumulation Using *E. coli* Strain Having Enhanced Expression of Carotenoid Biosynthesis Enzyme Genes In this Example, L-threonine production was performed by using an L-threonine-producing strain of *E. coli* introduced with carotenoid biosynthesis enzyme genes (crtEYIB), and the effect of an enhanced expression of carotenoid biosynthesis enzyme genes on L-threonine production and carotenoid accumulation was evaluated.

(1) Construction of Strains (1-1) Construction of pMW119-crtEYIB

PCR was performed using the chromosomal DNA of the WC196LC_crtEYIB(ML) strain as the template, and primers infu-1F and infu-2R (SEQ ID NOS: 56 and 57), to amplify a DNA fragment Ptac-crtEYIB, which contains a nucleotide sequence consisting of Ptac promoter sequence and the crtEYIB genes ligated to the downstream of the Ptac promoter sequence. PCR was performed by using PrimeSTAR® MAX DNA polymerase (Takara BIO) according to the protocol attached to the enzyme. Separately, pMW119 was treated with XbaI and KpnI, and then mixed with Ptac-crtEYIB. The mixture was subjected to a reaction using In-Fusion® HD Cloning Kit, to obtain pMW119-crtEYIB, an expression plasmid for the crtEYIB genes in which Ptac-crtEYIB was inserted into the pMW119 vector.

(1-2) Introduction of Carotenoid Biosynthesis Genes into *E. coli* L-Threonine-Producing Bacterium The *E. coli* VKPM B-3996 strain (U.S. Pat. No. 5,175, 107) was transformed with pMW119-crtEYIB by the electroporation method, to obtain a strain VKPM B-3996/pMW119-crtEYIB, which is an L-threonine-producing bacterium introduced with carotenoid biosynthesis genes.

Similarly, the VKPM B-3996 strain was transformed with pMW119, to obtain a vector control strain VKPM B-3996/pMW119.

Hereinafter, unless otherwise stated, these transformants were cultured using a medium added with 50 mg/L ampicillin.

(2) Extraction and Quantification of Carotenoids

Carotenoids were extracted from bacterial cells with ethanol, and quantified by using HPLC. The procedure was the same as that described in Examples 2(2).

(3) L-Threonine Production Culture

Each strain was uniformly applied to LB agar medium, and cultured for 24 hr at 37° C. Cells were scraped off in an amount corresponding to about 1-cm square of the cultured plate, and suspended in 1 mL of physiological saline. The turbidity at a wavelength of 620 nm (OD620) was measured for the obtained cell suspension by using a spectrophotometer U-2800 (Hitachi High-Technologies). The cell suspension was inoculated into 20 mL of MS medium contained in a 500-mL-volume Sakaguchi flask so as to obtain a final OD620 of 0.126, and 0.6 g of Japanese Pharmacopeia $CaCO_3$ preliminarily sterilized by dry heating was added thereto. Culture was performed for about 48 hr at 37° C. with stirring at 120 rpm by using a reciprocal shaking culture apparatus. After completion of the culture, the amount of L-threonine accumulated in the medium was quantified by using a biosensor BF-7 (Oji Scientific Instruments).

(4) Results

As a result of extraction and quantification of carotenoids, accumulation of beta-carotene was confirmed in the strain introduced with pMW119-crtEYIB (Table 6). In addition, as a result of L-threonine production culture, the strain introduced with pMW119-crtEYIB showed an improved L-threonine accumulation as compared to the vector control strain (FIG. 4).

TABLE 6

Accumulated amount of carotenoids in *E. coli* L-threonine-producing bacterium

| Strain | beta-carotene (μg/g-DCW) |
|---|---|
| VKPM B-3996/pMW119 | N.D. |
| VKPM B-3996/pMW119-crtEYIB | 37.5 ± 1.6 |

N.D., Not Detected.

Example 4: L-Lysine Production and Carotenoid Accumulation Using *C. glutamicum* Strain Having Enhanced Expression of Carotenoid Biosynthesis Enzyme Genes In this Example, L-lysine production was performed by using an L-lysine-producing strain of *C. glutamicum* introduced with carotenoid biosynthesis enzyme genes (crtYZ), and the effect of an enhanced expression of carotenoid biosynthesis enzyme genes on L-lysine production and carotenoid accumulation was evaluated.

(1) Media Used

CM-Dex medium: 10 g/L polypeptone, 10 g/L yeast extract, 5 g/L glucose, 1 g/L $KH_2PO_4$, 3 g/L urea, 0.4 g/L $MgSO_4.7H_2O$, 0.01 g/L $FeSO_4.7H_2O$, 0.01 g/L $MnSO_4.5H_2O$, 1.2 g/L(T-N) filtrated soybean hydrolysate, pH 7.5 (adjusted with KOH). Agar (15 g/L) was further contained in the case of an agar medium.

Coryne.-Lys production medium: 100 g/L glucose, 55 g/L $(NH_4)_2SO_4$, 1.05 g/L(T-N) filtrated soybean hydrolysate, 1 g/L $KH_2PO_4$, 1 g/L $MgSO_4.7H_2O$, 0.01 g/L $FeSO_4.7H_2O$, 0.01 g/L $MnSO_4.5H_2O$, 2 mg/L vitamin B1-HCl, 0.5 mg/L biotin, 5 mg/L nicotinamide, pH 7.0 (adjusted with KOH).

(2) Construction of Strains (2-1) Construction of pVS7_PmsrA_crtYZ

A DNA (PmsrA_crtYZ; SEQ ID NO: 33) that includes an operon structure consisting of a promoter sequence of msrA gene (PmsrA) and crtY and crtZ genes derived from *P. ananatis* ligated to the downstream of PmsrA was totally-synthesized (Eurofins Genomics). PmsrA_crtYZ was inserted into pVS7 (WO2013/069634), to construct pVS7 PmsrA_crtYZ, an expression plasmid for the crtY and crtZ genes derived from *P. ananatis*. Upon insertion into pVS7, the 5'-terminal and 3'-terminal sides of PmsrA_crtYZ were ligated to PstI and BamHI sites of pVS7, respectively.

(2-2) Introduction of pVS7 PmsrA_crtYZ into *C. glutamicum*

The *C. glutamicum* AJ3990 strain (ATCC 31269) was transformed with pVS7_PmsrA_crtYZ by the electroporation method, and cultured on CM-Dex agar medium containing 25 mg/L spectinomycin at 31.5° C., to obtain a strain AJ3990/pVS7_PmsrA_crtYZ, which is a transformant introduced with crtY and crtZ genes derived from *P. ananatis*.

Similarly, the AJ3990 strain was transformed with pVS7, to obtain a vector control strain AJ3990/pVS7.

(3) Extraction and Quantification of Carotenoids

Carotenoids were extracted from bacterial cells with an ethanol/acetone mixture (ethanol:acetone=7:3), and quantified by using HPLC. The procedure is described below.

Each strain was cultured on CM-Dex agar medium for 48 hr at 31.5° C. The subsequent procedure was the same as that described in Examples 2(2), except that the ethanol/acetone mixture was used instead of ethanol.

(4) L-Lysine Production Culture

Each strain was uniformly applied to CM-Dex agar medium containing 25 mg/L spectinomycin, and cultured for 24 hr at 31.5° C. Cells were scraped off in an amount corresponding to about 1-cm square of the cultured plate, and suspended in 1 mL of physiological saline. The turbidity at a wavelength of 620 nm (OD620) was measured for the obtained cell suspension by using a spectrophotometer U-2800 (Hitachi High-Technologies). The cell suspension was inoculated into 20 mL of Coryne.-Lys production medium contained in a 500-mL-volume Sakaguchi flask so as to obtain a final OD620 of 0.126, and 1.0 g of Japanese Pharmacopeia $CaCO_3$ preliminarily sterilized by dry heating was added thereto. Culture was performed for about 48 hr at 37° C. with stirring at 120 rpm by using a reciprocal shaking culture apparatus. After completion of the culture, the amount of L-lysine accumulated in the medium was quantified by using a Biotech-analyzer AS-210 (SAKURA SI).

(5) Results

As a result of extraction and quantification of carotenoids, accumulation of beta-carotene was confirmed in the strain introduced with pVS7 PmsrA_crtYZ, and this strain also showed an increased amount of total carotenoids as compared to the vector control strain (FIG. 5). In addition, as a result of L-lysine production culture, the strain introduced with pVS7_PmsrA_crtYZ showed an improved L-lysine accumulation as compared to the vector control strain (FIG. 6).

Example 5: L-Glutamic Acid Production and Carotenoid Accumulation Using *P. Ananatis* Strain Having Enhanced Expression of Carotenoid Biosynthesis Enzyme Gene(s)

In this Example, L-glutamic acid production was performed by using an L-glutamic acid-producing strain of *P. ananatis* having an enhanced expression of carotenoid biosynthesis enzyme gene(s) (crtE and/or crtW), and the effect of an enhanced expression of carotenoid biosynthesis enzyme gene(s) on L-glutamic acid production and carotenoid accumulation was evaluated.

(1) Medium Used

MSII medium: 40 g/L glucose, 0.5 g/L $MgSO_4.7H_2O$, 20 g/L $(NH_4)_2SO_4$, 2 g/L $KH_2PO_4$, 0.5 g/L NaCl, 2 g/L yeast extract, 0.25 g/L $CaCl_2.7H_2O$, 20 mg/L $FeSO_4.7H_2O$, 20 mg/L $MnSO_4.nH_2O$, 4 mL/L Trace element (0.66 g/L $CaCl_2.2H_2O$, 0.18 g/L $ZnSO_4.7H_2O$, 0.16 g/L $CuSO_4.5H_2O$, 0.15 g/L $MnSO_4.4H_2O$, 0.18 g/L $CoCl_2.6H_2O$, 0.10 g/L $H_3BO_3$, 0.30 g/L $Na_2MoO_4$), 200 mg/L L-Lys, 200 mg/L DL-Met, 200 mg/L DAP, pH 7.0 (adjusted with KOH). Japanese Pharmacopeia $CaCO_3$ preliminarily sterilized by dry heating was added at a concentration of 50 g/L immediately before culture.

(2) Construction of Strains (2-1) Enhanced Expression of crtE Gene

The chromosomal DNA of the *P. ananatis* SC17(0) ΔcrtEX::$P_{tac}$_crtE_$Km^r$ strain was extracted, and the *P. ananatis* NA1ΔsdhA strain (Japanese Patent Laid-open (Kokai) No. 2010-041920) was transformed with this chromosomal DNA by the electroporation method. The NA1ΔsdhA strain is an L-glutamic acid-producing strain derived from the *P. ananatis* AJ13601 strain (FERM BP-7207). Transformants were selected by culturing on LBGM9 agar medium containing 40 mg/L kanamycin for 24 hr at 34° C. Among the obtained strains, a strain in which insertion of the λattL_$Km^r$_λattR_$P_{tac}$ crtE sequence was confirmed was designated as NA1ΔsdhAΔcrtEX::$P_{tac}$_crtE_$Km^r$ strain.

(2-2) Introduction of crtW Gene

The NA1ΔsdhAΔcrtEX::$P_{tac}$_crtE_$Km^r$ strain was transformed with pMIV_Pnlp8_crtW by the electroporation method. Transformants were selected by culturing on LBGM9 agar medium containing 25 mg/L chloramphenicol for 24 hr at 34° C., and one of them was designated as NA1ΔsdhAΔcrtEX::$P_{tac}$_crtE_$Km^r$/pMIV_Pnlp8_crtW strain. Similarly, the NA1ΔsdhA strain was transformed with pMIV5JS, to obtain a vector control strain NA1ΔsdhA/pMIV5JS.

Hereinafter, unless otherwise stated, these transformants were cultured using a medium added with 25 mg/L chloramphenicol.

(3) Extraction and Quantification of Carotenoids

Carotenoids were extracted from bacterial cells with ethanol, and quantified by using HPLC. The procedure is described below.

Each strain was cultured on LBGM9 agar medium for 48 hr at 34° C. The subsequent procedure was the same as that described in Examples 2(2).

(4) L-Glutamic Acid Production Culture

Each strain was uniformly applied to LBGM9 agar medium, and cultured for 24 hr at 34° C. Cells were scraped off in an amount corresponding to about 1-cm square of the cultured plate, inoculated into 5 mL of MSII medium contained in a large test tube, and cultured for 24 hr at 34° C. at 120 rpm. After completion of the culture, the amount of L-glutamic acid accumulated in the medium was quantified by using a Biotech-analyzer AS-210 (SAKURA SI).

(5) Results (5-1) Effect of Enhanced Expression of crtE Gene

As a result of extraction and quantification of carotenoids, accumulation of zeaxanthin was confirmed in the strain having an enhanced expression of crtE gene (NA1ΔsdhAΔcrtEX::$P_{tac}$_crtE_$Km^r$ strain), and this strain also showed an increased amount of total carotenoids as compared to the control strain NA1ΔsdhA (FIG. 7). No accumulation of canthaxanthin or astaxanthin was confirmed for any strain. In addition, as a result of L-glutamic acid production culture, the strain having an enhanced expression of crtE gene (NA1ΔsdhAΔcrtEX::P$_{tac}$_crtE_Km$^r$ strain) showed an improved L-glutamic acid accumulation as compared to the control strain NA1ΔsdhA (FIG. 8).

(5-2) Effect of Introduction of crtW Gene

As a result of extraction and quantification of carotenoids, accumulation of canthaxanthin and astaxanthin was confirmed in the strain introduced with the crtW gene derived from *N. punctiforme* (NA1ΔsdhAΔcrtEX::P$_{tac}$_crtE_Km$^r$/pMIV_Pnlp8_crtW strain), and this strain also showed an increased amount of total carotenoids as compared to the vector control strain NA1ΔsdhA/pMIV5JS (FIG. 9). No accumulation of zeaxanthin was confirmed for any strain. In addition, as a result of L-glutamic acid production culture, the strain introduced with the crtW gene (NA1ΔsdhAΔcrtEX::P$_{tac}$_crtE_Km$^r$/pMIV_Pnlp8_crtW strain) showed an improved L-glutamic acid accumulation as compared to the vector control strain NA1ΔsdhA/pMIV5JS (FIG. 10).

Example 6: Culturing of Rainbow Trout Using Astaxanthin-Containing Bacterial Cells (1)

In this Example, astaxanthin was quantified by using a high performance chromatography (HPLC, LC-20AT, Shimadzu Corporation). The column used was Luna 3μ Silica Φ4.6 mm×150 mm. A mixture of hexane and acetone (82:18) as the mobile phase was passed through at a flow rate of 1.2 ml/min at a constant temperature, and detection was carried out at a wavelength of 470 nm. The amount of total carotenoids was quantified by extraction of the carotenoids with acetone and detection at wavelength of 478 nm using a spectrophotometer.

For test groups, a common feed for trout mainly containing fishmeal was ground, and then amino acid cells (dry cells of an L-lysine-producing strain of *E. coli* having an enhanced expression of astaxanthin-biosynthesis enzyme genes) in an amount of 3.3% or 5.5% were added to the feed. They were mixed, and the mixture was re-pelletized, to obtain feeds for rainbow trout of test groups (amino acid cell groups). As a positive control, the same common feed for trout after grinding was added and mixed with commercially-available synthesized astaxanthin (CAROPHYLL Pink; DSM) in such an amount that the addition amount of astaxanthin to the feed should be equal to that of the group added with 5.5% amino acid cells. The mixture was re-pelletized, to obtain a feed for rainbow trout of control group (synthesized product group). As a negative control, a feed not added with astaxanthin (control group) was prepared. This feed for control group was prepared by re-pelletizing without addition of any additive after grinding.

Results of analysis of the amounts of total carotenoids and astaxanthin in the feeds used in the experiment are shown in Table 7. The synthesized product group and the 5.5% and 3.3% amino acid cell groups showed higher amounts of total carotenoids and astaxanthin than the control group. Meanwhile, the 5.5% amino acid cell group contained almost the same amount of astaxanthin with that in the synthesized product group, and showed a higher amount of total carotenoids than the synthesized product group.

TABLE 7

Contained amounts of carotenoids in feeds used in the experiment

| | Control group | Synthesized product group | 5.5% amino acid cell group | 3.3% amino acid cell group |
|---|---|---|---|---|
| Total carotenoids (mg/100 g) | 1.49 | 2.91 | 4.93 | 3.8 |
| Astaxanthin (mg/100 g) | 0.26 | 1.84 | 1.79 | 1.39 |

Two hundred and fifty (250) rainbow trout having a body weight of about 100 g were introduced into 10 water tanks (200 L) of closed recirculating system so that each tank contained 25 rainbow trout, and cultured for 3 months. Due to the limited number of the tanks, 2 tanks were used for the control group, 2 tanks were used for the synthesized product group, 3 tanks were used for the 3.3% amino acid cell group, and 3 tanks were used for the 5.5% amino acid cell group. As an evaluation item, the body weight of all individuals was measured after 1 month, 2 months, and 3 months. The mean body weight of each group during the experimental period is shown in Table 8. Four (4) individuals per tank having a body weight close to the mean value were sampled, and the color tone of fillet was measured at 2 positions, i.e. at a head-side position and a tail-side position, by using a spectrophotometer (CM-700d, Konica Minolta). The mean values thereof are shown in Table 9. The spectrophotometer enables measurement of L, brightness; a, redness; and b, yellowness, and a higher value of "a" indicates a higher degree of coloring of an object toward reddish color. In addition, the amounts of carotenoids and astaxanthin in fillet of the same individuals were analyzed. The mean values thereof are shown in Table 10.

No difference in the mean body weight during the experimental period was observed among the test groups (Table 8).

The "a" value of fillet of individuals of the 5.5% amino acid cell group was higher than that of the synthesized product group containing an equal amount of astaxanthin.

The amount of astaxanthin present in fillet of individuals of the 5.5% amino acid cell group was equal to that of the synthesized product group containing an equal amount of astaxanthin, and the amounts of total carotenoids in fillet of individuals of the 5.5% amino acid cell group was higher than that of the synthesized product group.

TABLE 8

Mean body weight (g) during experimental period

| | At start | After 1 month | After 2 months | After 3 months |
|---|---|---|---|---|
| Control group | 106.4 | 142.6 | 182.8 | 241.7 |
| Synthesized product group | 106.6 | 146.8 | 184.7 | 233.9 |
| 5.5% amino acid cell group | 105.9 | 143.0 | 195.7 | 254.1 |
| 3.3% amino acid cell group | 105.5 | 147.5 | 202.5 | 257.3 |

TABLE 9

Color tone of fillet

| | | Control group | Synthesized product group | 5.5% amino acid cell group | 3.3% amino acid cell group |
|---|---|---|---|---|---|
| After 1 month | | | | | |
| Head side | L | 51.2 | 48.2 | 47.1 | 49.2 |
| | a | −0.6 | 2.3 | 3.8 | 1.9 |
| | b | 4.8 | 8.5 | 7.8 | 6.4 |

TABLE 9-continued

Color tone of fillet

|  |  | Control group | Synthesized product group | 5.5% amino acid cell group | 3.3% amino acid cell group |
|---|---|---|---|---|---|
| Tail side | L | 51.3 | 48.8 | 45.5 | 49.0 |
|  | a | 1.0 | 4.7 | 7.0 | 4.7 |
|  | b | 6.5 | 9.4 | 10.5 | 8.8 |
| After 2 months |  |  |  |  |  |
| Head side | L | 48.8 | 47.6 | 47.9 | 47.7 |
|  | a | 0.1 | 3.5 | 4.1 | 3.1 |
|  | b | 6.3 | 6.9 | 7.3 | 7.1 |
| Tail side | L | 48.0 | 46.0 | 46.3 | 46.4 |
|  | a | 1.6 | 6.8 | 7.1 | 5.9 |
|  | b | 7.0 | 9.0 | 9.7 | 8.5 |
| After 3 months |  |  |  |  |  |
| Head side | L | 51.1 | 47.6 | 43.6 | 44.4 |
|  | a | 0.4 | 4.0 | 5.5 | 4.6 |
|  | b | 6.7 | 7.7 | 7.4 | 7.3 |
| Tail side | L | 48.4 | 44.9 | 42.8 | 54.4 |
|  | a | 2.2 | 7.5 | 8.4 | 7.7 |
|  | b | 8.0 | 10.8 | 10.3 | 10.1 |

TABLE 10

Amount of carotenoids in fillet

|  | Control group | Synthesized product group | 5.5% amino acid cell group | 3.3% amino acid cell group |
|---|---|---|---|---|
| After 1 month |  |  |  |  |
| Astaxanthin mg/100 g | 0.04 | 0.16 | 0.13 | 0.11 |
| Total carotenoids mg/100 g | 0.07 | 0.17 | 0.22 | 0.17 |
| After 2 months |  |  |  |  |
| Astaxanthin mg/100 g | 0.06 | 0.31 | 0.20 | 0.16 |
| Total carotenoids mg/100 g | 0.07 | 0.30 | 0.30 | 0.24 |
| After 3 months |  |  |  |  |
| Astaxanthin mg/100 g | 0.08 | 0.33 | 0.31 | 0.27 |
| Total carotenoids mg/100 g | 0.10 | 0.34 | 0.46 | 0.40 |

Example 7: Culturing of Rainbow Trout Using Astaxanthin-Containing Bacterial Cells (2)

For tests, a common feed for trout mainly containing fishmeal is ground, and then amino acid cells (dry cells of an L-lysine-producing strain of *E. coli* having an enhanced expression of astaxanthin-biosynthesis enzyme genes) are added to the feed. They are mixed, and the mixture is re-pelletized, to obtain a feed for rainbow trout of test group (amino acid cell group). A feed blended with astaxanthin derived from *Phaffia* yeast (*Phaffia* yeast group), a feed blended with astaxanthin derived from *Paracoccus* (*Paracoccus* group), and a feed blended with astaxanthin derived from *Haematococcus* (*Haematococcus* group) are prepared by a similar manner so that the amount of astaxanthin is equal to that in the feed of the amino acid cell group, to obtain test feeds. A feed for control group is prepared by re-pelletizing without addition of any additive after grinding. 5 test groups are used: control group, amino acid cell group, *Phaffia* yeast group, *Paracoccus* group, and *Haematococcus* (*Haematococcus* group).

Two hundred and fifty (250) rainbow trout having a body weight of about 100 g are introduced into 10 water tanks (200 L) of closed recirculating system so that each tank contained 25 rainbow trout, and cultured for 3 months. 2 tanks are used for each group. As an evaluation item, the body weight of each individual trout is measured after 1 month, 2 months, and 3 months, and the mean body weights during the experimental period are compared among the groups. Four (4) individual trout per tank having a body weight close to the mean value are sampled, the color tone of each fillet is measured at 2 positions, i.e. at a head-side position and a tail-side position, by using a spectrophotometer (CM-700d, Konica Minolta), and the mean values thereof are compared.

Example 8: Culturing of Atlantic Salmon Using Astaxanthin-Containing Bacterial Cells (1)

Feed is prepared for 5 test groups: a feed for salmon without astaxanthin (control group), a feed for salmon added with 50 ppm of synthesized astaxanthin (synthesized product group), feed for salmon added with amino acid cells (dry cells of an L-lysine-producing strain of *E. coli* having an enhanced expression of astaxanthin-biosynthesis enzyme genes) in terms of 25, 50, and 75 ppm of astaxanthin (amino acid cell groups; 25 ppm, 50 ppm, and 75 Ppm).

Atlantic salmon having a body weight of about 200 g at the start of the test are introduced into 10 water tanks containing 850 L of seawater so that each tank contained 30 Atlantic salmon, and are cultured for 84 days. 2 tanks are used for each group. As evaluation items, the body weight and the feeding amount of the feed are measured once every 4 weeks, and the feed efficiency is calculated. In addition, Atlantic salmon are sampled once every 4 weeks, the color tone of each fillet is measured and compared by using a spectrophotometer and SalmoFan™, and the amount of astaxanthin present in each fillet is measured and compared.

Example 9: Culturing of Atlantic Salmon Using Astaxanthin-Containing Bacterial Cells (2)

Feed is prepared for 6 test groups: a feed for salmon without astaxanthin (control group), a feed for salmon added with amino acid cells (dry cells of an L-lysine-producing strain of *E. coli* having an enhanced expression of astaxanthin-biosynthesis enzyme genes) in the optimal amount determined in Example 8 (amino acid cell group), a feed for salmon added with astaxanthin derived from *Phaffia* yeast (*Phaffia* yeast group), a feed for salmon added with astaxanthin derived from *Paracoccus* (*Paracoccus* group), and a feed for salmon added with astaxanthin derived from *Haematococcus* (*Haematococcus* group).

Atlantic salmon each having a body weight of about 200 g at the start of test are introduced into 12 water tanks containing 850 L of seawater so that each tank contained 30 Atlantic salmon, and are cultured for 84 days. 2 tanks are used for each group. As evaluation items, the body weight and the feeding amount of the feed are measured once every 4 weeks, and the feed efficiency is calculated. In addition, Atlantic salmon are sampled once every 4 weeks, the color tone of each fillet is measured and compared by using a spectrophotometer and SalmoFan™, and the contained amount of astaxanthin in each fillet is measured and compared.

INDUSTRIAL APPLICABILITY

According to the present invention, an L-amino acid-producing ability of a bacterium can be improved, and an L-amino acid can be efficiently produced. In addition, in an embodiment as described herein, by allowing an L-amino acid-producing bacterium to produce a carotenoid, bacterial cells containing the carotenoid can be obtained and used as a by-product of L-amino acid production.

EXPLANATION OF SEQUENCE LISTING

SEQ ID NOS:
1-6: Primers
7: Nucleotide sequence of yggB gene of *Corynebacterium glutamicum* 2256 (ATCC 13869)
8: Amino acid sequence of YggB protein of *Corynebacterium glutamicum* 2256 (ATCC 13869)
9: Nucleotide sequence of mutant yggB gene (V419::IS) of *Corynebacterium glutamicum* 2256 (ATCC 13869)
10: Amino acid sequence of protein encoded by mutant yggB gene (V419::IS) of *Corynebacterium glutamicum* 2256 (ATCC 13869)
11: Nucleotide sequence of crtE gene of *Pantoea ananatis* AJ13355
12: Amino acid sequence of CrtE protein of *Pantoea ananatis* AJ13355
13: Nucleotide sequence of crtB gene of *Pantoea ananatis* AJ13355
14: Amino acid sequence of CrtB protein of *Pantoea ananatis* AJ13355
15: Nucleotide sequence of crtI gene of *Pantoea ananatis* AJ13355
16: Amino acid sequence of CrtI protein of *Pantoea ananatis* AJ13355
17: Nucleotide sequence of crtY gene of *Pantoea ananatis* AJ13355
18: Amino acid sequence of CrtY protein of *Pantoea ananatis* AJ13355
19: Nucleotide sequence of crtW gene of *Nostoc* sp. PCC 7120
20: Amino acid sequence of CrtW protein of *Nostoc* sp. PCC 7120
21: Nucleotide sequence of crtZ gene of *Pantoea ananatis* AJ13355
22: Amino acid sequence of CrtZ protein of *Pantoea ananatis* AJ13355
23: Nucleotide sequence of crtE gene of *Corynebacterium glutamicum* ATCC 13032
24: Amino acid sequence of CrtE protein of *Corynebacterium glutamicum* ATCC 13032
25: Nucleotide sequence of crtB gene of *Corynebacterium glutamicum* ATCC 13032
26: Amino acid sequence of CrtB protein of *Corynebacterium glutamicum* ATCC 13032
27: Nucleotide sequence of crtI gene of *Corynebacterium glutamicum* ATCC 13032
28: Amino acid sequence of CrtI protein of *Corynebacterium glutamicum* ATCC 13032
29: Nucleotide sequence of crtW gene of *Brevundimonas aurantiaca*
30: Amino acid sequence of CrtW protein of *Brevundimonas aurantiaca*
31-32: Primers
33: Nucleotide sequence of PmsrA_crtYZ
34-36: Primers
37: Nucleotide sequence of crtZ gene of *Brevundimonas* sp. SD-212
38-41: Primers
42: Nucleotide sequence of crtZ gene of *Paracoccus* sp. N81106
43-45: Primers
46: Nucleotide sequence of crtZ gene of *Alcaligenes* sp.
47-49: Primers
50: Nucleotide sequence of crtW gene of *Nostoc punctiforme* (codon-optimized for expression in *E. coli*)
51-54: Primers
55: Nucleotide sequence of DNA containing crtW gene of *Brevundimonas aurantiaca*
56-57: Primers
58: Amino acid sequence of CrtZ protein of *Brevundimonas* sp. SD-212
59: Amino acid sequence of CrtZ protein of *Paracoccus* sp. N81106
60: Amino acid sequence of CrtZ protein of *Alcaligenes* sp.
61: Amino acid sequence of CrtW protein of *Nostoc punctiforme*

---

The invention claimed is:

1. A method for producing an L-amino acid, the method comprising:
   culturing cells of a bacterium belonging to the genus *Pantoea* and having an L-amino acid-producing ability in a medium to accumulate an L-amino acid in the medium; and
   collecting the L-amino acid from the medium,
   wherein the bacterium has been modified so that the activity of a carotenoid biosynthesis enzyme is increased as compared with a non-modified bacterium,
   wherein the activity of the carotenoid biosynthesis enzyme is increased by increasing the expression of a gene encoding the carotenoid biosynthesis enzyme;
   wherein the carotenoid biosynthesis enzyme is selected from the group consisting of geranylgeranyl pyrophosphate synthase, phytoene synthase, phytoene desaturase, lycopene beta-cyclase, carotene ketolase, carotene hydroxylase, and combinations thereof;
   wherein the geranylgeranyl pyrophosphate synthase is a protein selected from the group consisting of:
   (a) a protein comprising the amino acid sequence of SEQ ID NO: 12 or 24,
   (b) a protein comprising the amino acid sequence of SEQ ID NO: 12 or 24, wherein the protein comprises 1 to 10 amino acid residues substituted, deleted, inserted, and/or added, and having geranylgeranyl pyrophosphate synthase activity, and
   (c) a protein comprising an amino acid sequence having at least 90% sequence identity to the amino acid sequence of SEQ ID NO: 12 or 24, and having geranylgeranyl pyrophosphate synthase activity;
   wherein the phytoene synthase is a protein selected from the group consisting of:
   (a) a protein comprising the amino acid sequence of SEQ ID NO: 14 or 26,
   (b) a protein comprising the amino acid sequence of SEQ ID NO: 14 or 26, wherein the protein comprises 1 to 10 amino acid residues substituted, deleted, inserted, and/or added, and having phytoene synthase activity, and
   (c) a protein comprising an amino acid sequence having at least 90% sequence identity to the amino acid sequence of SEQ ID NO: 14 or 26, and having phytoene synthase activity;
   wherein the phytoene desaturase is a protein selected from the group consisting of:
   (a) a protein comprising the amino acid sequence of SEQ ID NO: 16 or 28,
   (b) a protein comprising the amino acid sequence of SEQ ID NO: 16 or 28,
   wherein the protein comprises 1 to 10 amino acid residues substituted, deleted, inserted, and/or added, and having phytoene desaturase activity, and
   (c) a protein comprising an amino acid sequence having at least 90% sequence identity to the amino acid sequence of SEQ ID NO: 16 or 28, and having phytoene desaturase activity;
   wherein the lycopene beta-cyclase is a protein selected from the group consisting of:
   (a) a protein comprising the amino acid sequence of SEQ ID NO: 18,
   (b) a protein comprising the amino acid sequence of SEQ ID NO: 18, wherein the protein comprises 1 to 10 amino acid residues substituted, deleted, inserted, and/or added, and having lycopene beta-cyclase activity, and
   (c) a protein comprising an amino acid sequence having at least 90% sequence identity to the amino acid sequence of SEQ ID NO: 18, and having lycopene beta-cyclase activity;
   wherein the carotene ketolase is a protein selected from the group consisting of:

(a) a protein comprising the amino acid sequence of SEQ ID NO: 20, 30, or 61,
(b) a protein comprising the amino acid sequence of SEQ ID NO: 20, 30, or 61, wherein the protein comprises 1 to 10 amino acid residues substituted, deleted, inserted, and/or added, and having carotene ketolase activity, and
(c) a protein comprising an amino acid sequence having at least 90% sequence identity to the amino acid sequence of SEQ ID NO: 20, 30, or 61, and having carotene ketolase activity; and
wherein the carotene hydroxylase is a protein selected from the group consisting of:
(a) a protein comprising the amino acid sequence of SEQ ID NO: 22, 58, 59, or 60,
(b) a protein comprising the amino acid sequence of SEQ ID NO: 22, 58, 59, or 60,
wherein the protein comprises 1 to 10 amino acid residues substituted, deleted, inserted, and/or added, and having carotene hydroxylase activity, and
(c) a protein comprising an amino acid sequence having at least 90% sequence identity to the amino acid sequence of SEQ ID NO: 22, 58, 59, or 60, and having carotene hydroxylase activity.

2. The method of claim 1, wherein at least the activities of geranylgeranyl pyrophosphate synthase, phytoene synthase, phytoene desaturase, and lycopene beta-cyclase are increased.

3. The method of claim 1, wherein the activity of carotene ketolase and/or carotene hydroxylase is/are increased.

4. The method of claim 1, wherein the expression of the gene is increased by increasing the copy number of the gene and/or modifying an expression control sequence of the gene.

5. The method of claim 1, wherein the bacterium is *Pantoea ananatis*.

6. The method of claim 1, wherein the L-amino acid is an L-amino acid of aspartate family and/or an L-amino acid of glutamate family.

7. The method of claim 1, wherein the L-amino acid is selected from the group consisting of L-lysine, L-threonine, L-glutamic acid, and combinations thereof.

8. The method of claim 1, wherein the bacterium produces a carotenoid, and said carotenoid accumulates in cells of the bacterium as a result of the culturing.

9. The method of claim 8, wherein the cells contain the carotenoid in an amount of at least 10 µg/g-DCW or more.

10. The method of claim 8, wherein the carotenoid is selected from the group consisting of beta-carotene, zeaxanthin, canthaxanthin, astaxanthine, and combinations thereof.

11. The method of claim 8, which further comprises collecting an additional product, wherein the additional product is the cells.

* * * * *

```
                        SEQUENCE LISTING

<160> NUMBER OF SEQ ID NOS: 61

<210> SEQ ID NO 1
<211> LENGTH: 80
<212> TYPE: DNA
<213> ORGANISM: Artificial Sequence
<220> FEATURE:
<223> OTHER INFORMATION: primer

<400> SEQUENCE: 1
ccgcatcttt cgcgttgccg taaatgtatc cgtttataag gacagcccga tgaagcctgc      60 tttttttatac taagttggca                                                 80

<210> SEQ ID NO 2
<211> LENGTH: 54
<212> TYPE: DNA
```

<210> SEQ ID NO 2
<211> LENGTH: 54
<212> TYPE: DNA
<213> ORGANISM: Artificial Sequence
<220> FEATURE:
<223> OTHER INFORMATION: primer

<400> SEQUENCE: 2
gtgttttttt gcgcagaccg tcatggcagt ctccttgtgt gaaattgtta tccg    54

<210> SEQ ID NO 3
<211> LENGTH: 55
<212> TYPE: DNA
<213> ORGANISM: Artificial Sequence
<220> FEATURE:
<223> OTHER INFORMATION: primer

<400> SEQUENCE: 3
cggataacaa tttcacacaa ggagacttgc catgacggtc tgcgcaaaaa aacac    55

<210> SEQ ID NO 4
<211> LENGTH: 80
<212> TYPE: DNA
<213> ORGANISM: Artificial Sequence
<220> FEATURE:
<223> OTHER INFORMATION: primer

<400> SEQUENCE: 4
cgcgagtcca gcccccacga gaatcagatc ataatgcggt tgcatagccg tctcctgtcg    60
attaactgac ggcagcgagt    80

<210> SEQ ID NO 5
<211> LENGTH: 80
<212> TYPE: DNA
<213> ORGANISM: Artificial Sequence
<220> FEATURE:
<223> OTHER INFORMATION: primer

<400> SEQUENCE: 5
cacaacacaa tacacaacat aaaaaagcca ttttcacttg agggttatgt tgaagcctgc    60 tttttttatac taagttggca    80

<210> SEQ ID NO 6
<211> LENGTH: 80
<212> TYPE: DNA
<213> ORGANISM: Artificial Sequence
<220> FEATURE:
<223> OTHER INFORMATION: primer

<400> SEQUENCE: 6
ggcgtgcacc atgatgatca ttccatcagg tacagcttcc cagcgacgta ctagagcggg    60
cgctgccaga gatgcgcagg    80

<210> SEQ ID NO 7
<211> LENGTH: 1602
<212> TYPE: DNA
<213> ORGANISM: Corynebacterium glutamicum

<400> SEQUENCE: 7
atgattttag gcgtacccat tcaatatttg ctctattcat tgtggaattg gattgtcgat    60
accggttttg atgtagcaat tatcctggtc ttggcgtttt tgattccacg tatcggccga    120
ctggccatgc gtattatcaa gcagcgagtg agtctgcag ccgatgcgga caccactaag    180
aaccagctcg cgttcgctgg cgttggcgtt tatatcgcgc aaattgtggc gttttttcatg    240 cttgccgtct ccgcgatgca ggcttttggt ttctctctcg cgggcgctgc gattccggca    300

```
accattgcgt cagctgccat tggtcttggt gcgcagtcga ttgttgcgga cttcttggcc    360
ggattttca tcctgacgga aaagcaattc ggcgtgggtg actgggtgcg ctttgagggc    420
aacggcatcg ttgttgaagg caccgtcatt gagatcacca tgcgcgcgac caaaattcgc    480
acgattgcac aagagaccgt gatcatcccg aactccacgg cgaaagtgtg catcaacaat    540
tctaataact ggtcgcgtgc ggttgtcgtt attccgatcc ccatgttggg ttctgaaaac    600
atcacagatg tcatcgcgcg ctctgaagct gcgactcgtc gcgcacttgg ccaggagaaa    660
atcgcaccgg aaatcctcgg tgaactcgat gtgcacccag ccacggaagt cacaccgcca    720
acggtggtcg gcatgccgtg gatggtcacc atgcgtttcc tcgtgcaagt caccgccggc    780
aatcaatggc tggtcgaacg cgccatccgc acagaaatca tcaacgaatt ctgggaagaa    840
tacggcagcg caaccactac atcgggaacc ctcattgatt ccttacacgt tgagcatgaa    900
gagccaaaga cctcgcttat cgacgcctcc ccccaggctc ttaaggaacc gaagccggag    960
gctgcgcgca cggttgcatc gctagctgca tcgtctaacg acgatgcaga caatgcagac   1020
gcctcggcga tcaatgcagg caatccagag aaggaacttg attccgatgt gctggaacaa   1080
gaactctcca gcgaagaacc ggaagaaaca gcaaaaccag atcactctct ccgaggcttc   1140
ttccgcactg attactaccc aaatcggtgg cagaagatcc tgtcgtttgg cggacgtgtc   1200
cgcatgagca cttccctgtt gttgggtgcg ctgctcttgc tgtcactatt taaggtcatg   1260
actgtggaac caagtgagaa ttggcaaaac tccagtggat ggctgtcacc aagcactgcc   1320
acctcaactg cggtgaccac ctccgaaact tccgcgccag caagcacgcc ttcgatgaca   1380
gtgcccacta cggtggagga cccccaacg atggaatcta gcgtcgaaac gcagcaggaa   1440
acctcaaccc ctgcaaccgc aacgccccag cgagccgaca ccatcgaacc gaccgaggaa   1500
gccacgtcgc aggaggaaac gactgcatcg cagacgcagt ctccagcagt ggaagcacca   1560
accgcggtcc aagaaacagt tgcgccgacg tccacccctt ag                      1602
```

<210> SEQ ID NO 8
<211> LENGTH: 533
<212> TYPE: PRT
<213> ORGANISM: Corynebacterium glutamicum

<400> SEQUENCE: 8

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140
```

```
Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
            165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
            210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Tyr Gly Ser Ala Thr Thr Thr Ser
            275                 280                 285

Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
            435                 440                 445

Glu Thr Ser Ala Pro Ala Ser Thr Pro Ser Met Thr Val Pro Thr Thr
            450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
            485                 490                 495

Pro Thr Glu Glu Ala Thr Ser Gln Glu Thr Thr Ala Ser Gln Thr
            500                 505                 510

Gln Ser Pro Ala Val Glu Ala Pro Thr Ala Val Gln Glu Thr Val Ala
            515                 520                 525

Pro Thr Ser Thr Pro
            530

<210> SEQ ID NO 9
<211> LENGTH: 3063
```

<212> TYPE: DNA
<213> ORGANISM: Corynebacterium glutamicum
<220> FEATURE:
<221> NAME/KEY: CDS
<222> LOCATION: (1)..(1269)

<400> SEQUENCE: 9

| | | | | | | | | | | | | | | | | |
|---|---|---|---|---|---|---|---|---|---|---|---|---|---|---|---|---|
| atg | att | tta | ggc | gta | ccc | att | caa | tat | ttg | ctc | tat | tca | ttg | tgg | aat | 48 |
| Met | Ile | Leu | Gly | Val | Pro | Ile | Gln | Tyr | Leu | Leu | Tyr | Ser | Leu | Trp | Asn | |
| 1 | | | | 5 | | | | | 10 | | | | | 15 | | |
| tgg | att | gtc | gat | acc | ggt | ttt | gat | gta | gca | att | atc | ctg | gtc | ttg | gcg | 96 |
| Trp | Ile | Val | Asp | Thr | Gly | Phe | Asp | Val | Ala | Ile | Ile | Leu | Val | Leu | Ala | |
| | | | 20 | | | | | 25 | | | | | 30 | | | |
| ttt | ttg | att | cca | cgt | atc | ggc | cga | ctg | gcc | atg | cgt | att | atc | aag | cag | 144 |
| Phe | Leu | Ile | Pro | Arg | Ile | Gly | Arg | Leu | Ala | Met | Arg | Ile | Ile | Lys | Gln | |
| | | 35 | | | | | 40 | | | | | 45 | | | | |
| cga | gtg | gag | tct | gca | gcc | gat | gcg | gac | acc | act | aag | aac | cag | ctc | gcg | 192 |
| Arg | Val | Glu | Ser | Ala | Ala | Asp | Ala | Asp | Thr | Thr | Lys | Asn | Gln | Leu | Ala | |
| | 50 | | | | | 55 | | | | | 60 | | | | | |
| ttc | gct | ggc | gtt | ggc | gtt | tat | atc | gcg | caa | att | gtg | gcg | ttt | ttc | atg | 240 |
| Phe | Ala | Gly | Val | Gly | Val | Tyr | Ile | Ala | Gln | Ile | Val | Ala | Phe | Phe | Met | |
| 65 | | | | | 70 | | | | | 75 | | | | | 80 | |
| ctt | gcc | gtc | tcc | gcg | atg | cag | gct | ttt | ggt | ttc | tct | ctc | gcg | ggc | gct | 288 |
| Leu | Ala | Val | Ser | Ala | Met | Gln | Ala | Phe | Gly | Phe | Ser | Leu | Ala | Gly | Ala | |
| | | | | 85 | | | | | 90 | | | | | 95 | | |
| gcg | att | ccg | gca | acc | att | gcg | tca | gct | gcc | att | ggt | ctt | ggt | gcg | cag | 336 |
| Ala | Ile | Pro | Ala | Thr | Ile | Ala | Ser | Ala | Ala | Ile | Gly | Leu | Gly | Ala | Gln | |
| | | | 100 | | | | | 105 | | | | | 110 | | | |
| tcg | att | gtt | gcg | gac | ttc | ttg | gcc | gga | ttt | ttc | atc | ctg | acg | gaa | aag | 384 |
| Ser | Ile | Val | Ala | Asp | Phe | Leu | Ala | Gly | Phe | Phe | Ile | Leu | Thr | Glu | Lys | |
| | | 115 | | | | | 120 | | | | | 125 | | | | |
| caa | ttc | ggc | gtg | ggt | gac | tgg | gtg | cgc | ttt | gag | ggc | aac | ggc | atc | gtt | 432 |
| Gln | Phe | Gly | Val | Gly | Asp | Trp | Val | Arg | Phe | Glu | Gly | Asn | Gly | Ile | Val | |
| | 130 | | | | | 135 | | | | | 140 | | | | | |
| gtt | gaa | ggc | acc | gtc | att | gag | atc | acc | atg | cgc | gcg | acc | aaa | att | cgc | 480 |
| Val | Glu | Gly | Thr | Val | Ile | Glu | Ile | Thr | Met | Arg | Ala | Thr | Lys | Ile | Arg | |
| 145 | | | | | 150 | | | | | 155 | | | | | 160 | |
| acg | att | gca | caa | gag | acc | gtg | atc | atc | ccg | aac | tcc | acg | gcg | aaa | gtg | 528 |
| Thr | Ile | Ala | Gln | Glu | Thr | Val | Ile | Ile | Pro | Asn | Ser | Thr | Ala | Lys | Val | |
| | | | | 165 | | | | | 170 | | | | | 175 | | |
| tgc | atc | aac | aat | tct | aat | aac | tgg | tcg | cgt | gcg | gtt | gtc | gtt | att | ccg | 576 |
| Cys | Ile | Asn | Asn | Ser | Asn | Asn | Trp | Ser | Arg | Ala | Val | Val | Val | Ile | Pro | |
| | | | 180 | | | | | 185 | | | | | 190 | | | |
| atc | ccc | atg | ttg | ggt | tct | gaa | aac | atc | aca | gat | gtc | atc | gcg | cgc | tct | 624 |
| Ile | Pro | Met | Leu | Gly | Ser | Glu | Asn | Ile | Thr | Asp | Val | Ile | Ala | Arg | Ser | |
| | | | 195 | | | | | 200 | | | | | 205 | | | |
| gaa | gct | gcg | act | cgt | cgc | gca | ctt | ggc | cag | gag | aaa | atc | gca | ccg | gaa | 672 |
| Glu | Ala | Ala | Thr | Arg | Arg | Ala | Leu | Gly | Gln | Glu | Lys | Ile | Ala | Pro | Glu | |
| | 210 | | | | | 215 | | | | | 220 | | | | | |
| atc | ctc | ggt | gaa | ctc | gat | gtg | cac | cca | gcc | acg | gaa | gtc | aca | ccg | cca | 720 |
| Ile | Leu | Gly | Glu | Leu | Asp | Val | His | Pro | Ala | Thr | Glu | Val | Thr | Pro | Pro | |
| 225 | | | | | 230 | | | | | 235 | | | | | 240 | |
| acg | gtg | gtc | ggc | atg | ccg | tgg | atg | gtc | acc | atg | cgt | ttc | ctc | gtg | caa | 768 |
| Thr | Val | Val | Gly | Met | Pro | Trp | Met | Val | Thr | Met | Arg | Phe | Leu | Val | Gln | |
| | | | | 245 | | | | | 250 | | | | | 255 | | |
| gtc | acc | gcc | ggc | aat | caa | tgg | ctg | gtc | gaa | cgc | gcc | atc | cgc | aca | gaa | 816 |
| Val | Thr | Ala | Gly | Asn | Gln | Trp | Leu | Val | Glu | Arg | Ala | Ile | Arg | Thr | Glu | |
| | | | 260 | | | | | 265 | | | | | 270 | | | |
| atc | atc | aac | gaa | ttc | tgg | gaa | gaa | tac | ggc | agc | gca | acc | act | aca | tcg | 864 |
| Ile | Ile | Asn | Glu | Phe | Trp | Glu | Glu | Tyr | Gly | Ser | Ala | Thr | Thr | Thr | Ser | |
| | | 275 | | | | | 280 | | | | | 285 | | | | |

| | | | | | | | | | | | | | | | | |
|---|---|---|---|---|---|---|---|---|---|---|---|---|---|---|---|---|
| gga | acc | ctc | att | gat | tcc | tta | cac | gtt | gag | cat | gaa | gag | cca | aag | acc | 912 |
| Gly | Thr | Leu | Ile | Asp | Ser | Leu | His | Val | Glu | His | Glu | Glu | Pro | Lys | Thr | |
| 290 | | | | | 295 | | | | | 300 | | | | | | |
| tcg | ctt | atc | gac | gcc | tcc | ccc | cag | gct | ctt | aag | gaa | ccg | aag | ccg | gag | 960 |
| Ser | Leu | Ile | Asp | Ala | Ser | Pro | Gln | Ala | Leu | Lys | Glu | Pro | Lys | Pro | Glu | |
| 305 | | | | 310 | | | | | 315 | | | | | 320 | | |
| gct | gcg | gcg | acg | gtt | gca | tcg | cta | gct | gca | tcg | tct | aac | gac | gat | gca | 1008 |
| Ala | Ala | Ala | Thr | Val | Ala | Ser | Leu | Ala | Ala | Ser | Ser | Asn | Asp | Asp | Ala | |
| | | | 325 | | | | | 330 | | | | | 335 | | | |
| gac | aat | gca | gac | gcc | tcg | gcg | atc | aat | gca | ggc | aat | cca | gag | aag | gaa | 1056 |
| Asp | Asn | Ala | Asp | Ala | Ser | Ala | Ile | Asn | Ala | Gly | Asn | Pro | Glu | Lys | Glu | |
| | | | 340 | | | | | 345 | | | | | 350 | | | |
| ctt | gat | tcc | gat | gtg | ctg | gaa | caa | gaa | ctc | tcc | agc | gaa | gaa | ccg | gaa | 1104 |
| Leu | Asp | Ser | Asp | Val | Leu | Glu | Gln | Glu | Leu | Ser | Ser | Glu | Glu | Pro | Glu | |
| | | | 355 | | | | | 360 | | | | | 365 | | | |
| gaa | aca | gca | aaa | cca | gat | cac | tct | ctc | cga | ggc | ttc | ttc | cgc | act | gat | 1152 |
| Glu | Thr | Ala | Lys | Pro | Asp | His | Ser | Leu | Arg | Gly | Phe | Phe | Arg | Thr | Asp | |
| | 370 | | | | | 375 | | | | | 380 | | | | | |
| tac | tac | cca | aat | cgg | tgg | cag | aag | atc | ctg | tcg | ttt | ggc | gga | cgt | gtc | 1200 |
| Tyr | Tyr | Pro | Asn | Arg | Trp | Gln | Lys | Ile | Leu | Ser | Phe | Gly | Gly | Arg | Val | |
| 385 | | | | | 390 | | | | | 395 | | | | | 400 | |
| cgc | atg | agc | act | tcc | ctg | ttg | ttg | ggt | gcg | ctg | ctc | ttg | ctg | tca | cta | 1248 |
| Arg | Met | Ser | Thr | Ser | Leu | Leu | Leu | Gly | Ala | Leu | Leu | Leu | Leu | Ser | Leu | |
| | | | 405 | | | | | 410 | | | | | 415 | | | |
| ttt | aag | ggg | ctc | ttc | ctg | ttt | tagagtgcat | | tgatcttatg | | gaccaactgc | | | | | 1299 |
| Phe | Lys | Gly | Leu | Phe | Leu | Phe | | | | | | | | | | |
| | | | 420 | | | | | | | | | | | | | |

| | | |
|---|---|---|
| cctgaatgga taaggcaccg cagaatgtag tggttcaaat tacggaaacc tagagcaatc | | 1359 |
| ccacgcaaat gctccaaccg tccgttgatc gcttcgaccg gaccgttgga gacaccaaca | | 1419 |
| tcgaaatacg ccaacacatc accaagtcgt ttaaacaaac tacgacccaa ctgcgcgagt | | 1479 |
| tccttattcg gccccttcaa cacccgaagc tgatcaataa tggtccgcat tttcttcttc | | 1539 |
| gcttcacgct tattacccat ctgataacaa tcaataatcg cctgatacgc aagccacgca | | 1599 |
| agctttaaca ccccgtagtc tttgtcatac gcccacaact gctccaagct tcttgctga | | 1659 |
| cgaggactca accacttgtg cgtggtcaac aaggtcttcc ggttttttata caacggatcc | | 1719 |
| tggcttaaac cacgacgctg gtatttctcc cgctggaggc gttgccggca ggcggtgagc | | 1779 |
| ttgtcaccag caagccgcac aacatggaat ggatccatca cgcgacgagc agaaggaatg | | 1839 |
| agttctttac ttgctgtggc gtagccttgg aacccatcca tggacacgat ccgtatctga | | 1899 |
| ttgcggaact gttcaccgcg ggaaccaagc caggaccgta aagcatcagc actacgacct | | 1959 |
| gggacgacat ctaataaccg ggcaggacac cgtgagtcat accgatgccc ggtcatatcg | | 2019 |
| acaatcacgg tgacaaaccc atcaccatgc ttagccctat tatgtgacca cttatgctca | | 2079 |
| tccacccaa tgacatacac tccatcaaga tggtgaggat cgttatagac cagctcacgg | | 2139 |
| cacatatcga gggctagttg gcaggttaaa tcccaccta gcccaagtgc tttcgcggtt | | 2199 |
| gcgtgaacac tcatccggtc aatagcaagg cgttgcaaaa tccagcgggt gacccggtgg | | 2259 |
| gtgaccttt taccgtggtc agcgcagctt agttctgctt ggaaatactt ttgcttacat | | 2319 |
| gtcgggttgg tgcagcggta gcgaggtaga cggataaaca gtttggtggg aaacccgacg | | 2379 |
| atgggtaaat caatgagcat ccggtgggtg tgatgacgaa acaccccagg ttgggagcat | | 2439 |
| tctgggcagg tggaggtata gtcgagtgcg ctgcttcga tcagggtgta atcacctgca | | 2499 |
| tcggaagcgc cggtgatggt gagtcctagt tccgcagtgc ggcagatggt gtcagcgatg | | 2559 |

```
atgttgccgg tagacttcat gggtagagcc ttttgttggt gtttggttag cttagatacc    2619
taaaccttaa ccctgacaaa aggctcgttt attttcgggt ctacaccgct agcccaggtt    2679
ctgtgatgta ccccaaaacc ggaagggcca tttaaggtca tgactgtgga accaagtgag    2739
aattggcaaa actccagtgg atggctgtca ccaagcactg ccacctcaac tgcggtgacc    2799
acctccgaaa cttccgcgcc agcaagcacg ccttcgatga cagtgcccac tacggtggag    2859
gagaccccaa cgatggaatc tagcgtcgaa acgcagcagg aaacctcaac ccctgcaacc    2919
gcaacgcccc agcgagccga caccatcgaa ccgaccgagg aagccacgtc gcaggaggaa    2979
acgactgcat cgcagacgca gtctccagca gtggaagcac caaccgcggt ccaagaaaca    3039
gttgcgccga cgtccacccc ttag                                           3063
```

<210> SEQ ID NO 10
<211> LENGTH: 423
<212> TYPE: PRT
<213> ORGANISM: Corynebacterium glutamicum

<400> SEQUENCE: 10

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285
```

```
Gly Thr Leu Ile Asp Ser Leu His Val Glu His Glu Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Gly Leu Phe Leu Phe
            420
```

```
<210> SEQ ID NO 11
<211> LENGTH: 909
<212> TYPE: DNA
<213> ORGANISM: Pantoea ananatis

<400> SEQUENCE: 11
atgacggtct gcgcaaaaaa acacgttcat ctcactcgcg atgctgcgga gcagttactg    60
gctgatattg atcgacgcct tgatcagtta ttgcccgtgg agggagaacg ggatgttgtg   120
ggtgccgcga tgcgtgaagg tgcgctggca ccgggaaaac gtattcgccc catgttgctg   180
ttgctgaccg cccgcgatct gggttgcgct gtcagccatg acggattact ggatttggcc   240
tgtgcggtgg aaatggtcca cgcggcttcg ctgatccttg acgatatgcc ctgcatggac   300
gatgcgaagc tgcggcgcgg acgccctacc attcattctc attacggaga gcatgtggca   360
atactggcgc ggttgccctt gctgagtaaa gcctttggcg taattgccga tgcagatggc   420
ctcacgccgc tggcaaaaaa tcgagcggtt tctgaactgt caaacgccat cggcatgcaa   480
ggattggttc agggtcagtt caaggacctg tctgaagggg ataagccgcg cagcgctgaa   540
gctattttga tgacgaatca ctttaaaacc agcacgctgt tttgtgcctc catgcagatg   600
gcctcgattg ttgcgaatgc ctccagcgaa gcgcgtgatt gcctgcatcg ttttcactt   660 gatcttggtc aggcatttca actgctggac gatttgaccg atggcatgac cgacaccggt   720
aaagatagca atcaggacgc cggtaaatcg acgctggtca atctgttagg cccgagggcg   780
gttgaagaac gtctgagaca acatcttcat cttgccagtg agcatctctc tgcggcctgc   840
caacacgggc acgccactca acattttatt caggcctggt ttgacaaaaa actcgctgcc   900
gtcagttaa                                                          909
```

```
<210> SEQ ID NO 12
<211> LENGTH: 302
<212> TYPE: PRT
<213> ORGANISM: Pantoea ananatis

<400> SEQUENCE: 12

Met Thr Val Cys Ala Lys Lys His Val His Leu Thr Arg Asp Ala Ala
1               5                   10                  15
```

-continued

```
Glu Gln Leu Leu Ala Asp Ile Asp Arg Arg Leu Asp Gln Leu Leu Pro
                20                  25                  30
Val Glu Gly Glu Arg Asp Val Val Gly Ala Ala Met Arg Glu Gly Ala
         35                  40                  45
Leu Ala Pro Gly Lys Arg Ile Arg Pro Met Leu Leu Leu Leu Thr Ala
 50                  55                  60
Arg Asp Leu Gly Cys Ala Val Ser His Asp Gly Leu Leu Asp Leu Ala
 65                  70                  75                  80
Cys Ala Val Glu Met Val His Ala Ala Ser Leu Ile Leu Asp Asp Met
                 85                  90                  95
Pro Cys Met Asp Asp Ala Lys Leu Arg Arg Gly Arg Pro Thr Ile His
                100                 105                 110
Ser His Tyr Gly Glu His Val Ala Ile Leu Ala Ala Val Ala Leu Leu
            115                 120                 125
Ser Lys Ala Phe Gly Val Ile Ala Asp Ala Asp Gly Leu Thr Pro Leu
        130                 135                 140
Ala Lys Asn Arg Ala Val Ser Glu Leu Ser Asn Ala Ile Gly Met Gln
145                 150                 155                 160
Gly Leu Val Gln Gly Gln Phe Lys Asp Leu Ser Glu Gly Asp Lys Pro
                165                 170                 175
Arg Ser Ala Glu Ala Ile Leu Met Thr Asn His Phe Lys Thr Ser Thr
            180                 185                 190
Leu Phe Cys Ala Ser Met Gln Met Ala Ser Ile Val Ala Asn Ala Ser
        195                 200                 205
Ser Glu Ala Arg Asp Cys Leu His Arg Phe Ser Leu Asp Leu Gly Gln
210                 215                 220
Ala Phe Gln Leu Leu Asp Asp Leu Thr Asp Gly Met Thr Asp Thr Gly
225                 230                 235                 240
Lys Asp Ser Asn Gln Asp Ala Gly Lys Ser Thr Leu Val Asn Leu Leu
                245                 250                 255
Gly Pro Arg Ala Val Glu Glu Arg Leu Arg Gln His Leu His Leu Ala
            260                 265                 270
Ser Glu His Leu Ser Ala Ala Cys Gln His Gly His Ala Thr Gln His
        275                 280                 285
Phe Ile Gln Ala Trp Phe Asp Lys Lys Leu Ala Ala Val Ser
290                 295                 300
```

<210> SEQ ID NO 13
<211> LENGTH: 891
<212> TYPE: DNA
<213> ORGANISM: Pantoea ananatis

<400> SEQUENCE: 13

```
atggcagttg gctcgaaaag ttttgcgaca gcctcaaagt tatttgatgc aaaaacccgg      60
cgcagcgtac tgatgctcta cgcctggtgc cgccattgtg acgatgttat tgacgaccag     120
acgctgggct tccaggcccg gcagcctgcc ttacaaacgc cgaacaacg tctgatgcaa      180
cttgagatga aaacgcgcca ggcctatgca ggatcgcaga tgcacgaacc ggcgtttgcg     240
gcttttcagg aagtggctat ggctcatgat atcgccccgg cttacgcgtt tgatcatctg     300
gaaggcttcg ccatggatgt acgcgaagcg caatacagcc aactggatga tacgctgcgc     360
tattgctatc acgttgcagg cgttgtcggc ttgatgatgg cgcaaatcat gggcgtacgg     420
gataaggcca cgctgaccg cgcctgtgac cttgggctgg catttcagtt gaccaatatt      480
gctcgcgata ttgtggacga tgcgcatgcg ggccgctgtt atctgccggc aagctggctg     540
```

```
gagcatgaag gtctgaacaa agagaattat gcggcacctg aaaaccgtca ggcgctgagc    600
cgtatcgccc gtcgtttggt gcaggaagca gaaccttact atttgtctgc cacagcgggc    660
ctggctaggt tgcccctgcg ttcggcctgg gcaatcgcta cggcgaagca ggtttaccgg    720
aaaataggtg taaagttga acaggccggt cagcaagcct gggatcagcg gcagtcaacg     780
accacgcccg aaaaattaac gctgctgctg ccgcctctg gtcaggccct tacttcccgg     840
atgcgggctc atcctccccg ccctgcgcat ctctggcagc gcccgctcta g             891
```

<210> SEQ ID NO 14
<211> LENGTH: 296
<212> TYPE: PRT
<213> ORGANISM: Pantoea ananatis

<400> SEQUENCE: 14

```
Met Ala Val Gly Ser Lys Ser Phe Ala Thr Ala Ser Lys Leu Phe Asp
  1               5                  10                  15

Ala Lys Thr Arg Arg Ser Val Leu Met Leu Tyr Ala Trp Cys Arg His
                 20                  25                  30

Cys Asp Asp Val Ile Asp Asp Gln Thr Leu Gly Phe Gln Ala Arg Gln
             35                  40                  45

Pro Ala Leu Gln Thr Pro Glu Gln Arg Leu Met Gln Leu Glu Met Lys
         50                  55                  60

Thr Arg Gln Ala Tyr Ala Gly Ser Gln Met His Glu Pro Ala Phe Ala
 65                  70                  75                  80

Ala Phe Gln Glu Val Ala Met Ala His Asp Ile Ala Pro Ala Tyr Ala
                 85                  90                  95

Phe Asp His Leu Glu Gly Phe Ala Met Asp Val Arg Glu Ala Gln Tyr
            100                 105                 110

Ser Gln Leu Asp Asp Thr Leu Arg Tyr Cys Tyr His Val Ala Gly Val
        115                 120                 125

Val Gly Leu Met Met Ala Gln Ile Met Gly Val Arg Asp Lys Ala Thr
    130                 135                 140

Leu Asp Arg Ala Cys Asp Leu Gly Leu Ala Phe Gln Leu Thr Asn Ile
145                 150                 155                 160

Ala Arg Asp Ile Val Asp Asp Ala His Ala Gly Arg Cys Tyr Leu Pro
                165                 170                 175

Ala Ser Trp Leu Glu His Glu Gly Leu Asn Lys Glu Asn Tyr Ala Ala
            180                 185                 190

Pro Glu Asn Arg Gln Ala Leu Ser Arg Ile Ala Arg Arg Leu Val Gln
        195                 200                 205

Glu Ala Glu Pro Tyr Tyr Leu Ser Ala Thr Ala Gly Leu Ala Arg Leu
    210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Gln Ala Trp Asp Gln
                245                 250                 255

Arg Gln Ser Thr Thr Thr Pro Glu Lys Leu Thr Leu Leu Ala Ala
            260                 265                 270

Ser Gly Gln Ala Leu Thr Ser Arg Met Arg Ala His Pro Pro Arg Pro
        275                 280                 285

Ala His Leu Trp Gln Arg Pro Leu
    290                 295
```

<210> SEQ ID NO 15
<211> LENGTH: 1479
<212> TYPE: DNA
<213> ORGANISM: Pantoea ananatis

<400> SEQUENCE: 15

```
atgaaaccaa ctacggtaat tggtgcaggc ttcggtggcc tggcactggc aattcgtcta      60
caggctgcgg ggatccccgt cttactgctt gaacaacgtg ataaacccgg cggtcgggct     120
tatgtctacg aggatcaggg gtttaccttt gatgcaggcc cgacggttat caccgatccc     180
agtgccattg aagaactgtt tgcactggca ggaaaacagt taaaagagta tgtcgaactg     240
ctgccggtta cgccgtttta ccgcctgtgt tgggagtcag ggaaggtctt taattacgat     300
aacgatcagg cccggctcga agcgcagatt cagcagttta tccccgcgga tgtcgaaggt     360
tatcgtcagt ttctggacta ttcacgcgcg gtgtttaaag aagggtatct gaagctcggt     420
actgtccctt ttttatcgtt cagagacatg cttcgcgccg cacctcaact ggcgaaactg     480
caggcatgga gaagcgttta cagtaaggtt gccagttaca tcgaagatga acatctgcgc     540
caggcgtttt cttttccactc gctgttggtg ggcggcaatc ccttcgccac ctcatccatt     600
tatacgttga tacacgcgct ggaacgtgag tggggcgtct ggtttccgcg tggcggcacc     660
ggcgcattag ttcaggggat gataaagctg tttcaggatc tgggtggcga agtcgtgtta     720
aacgccagag tcagccatat ggaaacgaca ggaaacaaga ttgaagccgt gcatttagag     780
gacggtcgca ggttcctgac gcaagccgtc gcgtcaaatg cagatgtggt tcataacctat     840 cgcgacctgt taagccagca ccctgccgcg gttaagcagt ccaacaaact gcagactaag     900
cgcatgagta actctctgtt tgtgctctat tttggtttga atcaccatca tgatcagctc     960
gcgcatcaca cggtttgttt cggcccgcgt taccgcgagc tgattgacga aattttttaat    1020 catgatggcc tcgcagaaga cttctcactt tatctgcacg cgccctgtgt cacggattcg    1080
tcactggcgc ctgaaggttg cggcagttac tatgtgttgg caccggtgcc gcatttaggc    1140
accgcgaacc tcgactggac ggttgagggg ccaaaactac gcgaccgtat ttttgagtac    1200
cttgagcagc attacatgcc tggcttacgg agtcagctgg tcacgcaccg gatgtttacg    1260
ccgtttgatt ttcgcgacca gcttaatgcc tatcagggct cagccttttc tgtggagccc    1320
gttcttaccc agagcgcctg gtttcggccg cataaccgcg ataaaaccat tactaatctc    1380
tacctggtcg gcgcaggcac gcatcccggc gcaggcattc ctggcgtcat cggctcggca    1440
aaagcgacag caggtttgat gctggaggat ctgatttga                           1479
```

<210> SEQ ID NO 16
<211> LENGTH: 492
<212> TYPE: PRT
<213> ORGANISM: Pantoea ananatis

<400> SEQUENCE: 16

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
                20                  25                  30

Arg Asp Lys Pro Gly Gly Arg Ala Tyr Val Tyr Glu Asp Gln Gly Phe
            35                  40                  45

Thr Phe Asp Ala Gly Pro Thr Val Ile Thr Asp Pro Ser Ala Ile Glu
        50                  55                  60

Glu Leu Phe Ala Leu Ala Gly Lys Gln Leu Lys Glu Tyr Val Glu Leu
65                  70                  75                  80
```

```
Leu Pro Val Thr Pro Phe Tyr Arg Leu Cys Trp Glu Ser Gly Lys Val
                 85                  90                  95

Phe Asn Tyr Asp Asn Asp Gln Ala Arg Leu Glu Ala Gln Ile Gln Gln
            100                 105                 110

Phe Asn Pro Arg Asp Val Glu Gly Tyr Arg Gln Phe Leu Asp Tyr Ser
            115                 120                 125

Arg Ala Val Phe Lys Glu Gly Tyr Leu Lys Leu Gly Thr Val Pro Phe
130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
            195                 200                 205

Arg Glu Trp Gly Val Trp Phe Pro Arg Gly Gly Thr Gly Ala Leu Val
            210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
            260                 265                 270

Asn Ala Asp Val Val His Thr Tyr Arg Asp Leu Leu Ser Gln His Pro
            275                 280                 285

Ala Ala Val Lys Gln Ser Asn Lys Leu Gln Thr Lys Arg Met Ser Asn
290                 295                 300

Ser Leu Phe Val Leu Tyr Phe Gly Leu Asn His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
            340                 345                 350

His Ala Pro Cys Val Thr Asp Ser Ser Leu Ala Pro Glu Gly Cys Gly
            355                 360                 365

Ser Tyr Tyr Val Leu Ala Pro Val Pro His Leu Gly Thr Ala Asn Leu
            370                 375                 380

Asp Trp Thr Val Glu Gly Pro Lys Leu Arg Asp Arg Ile Phe Glu Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr Gln
            420                 425                 430

Gly Ser Ala Phe Ser Val Glu Pro Val Leu Thr Gln Ser Ala Trp Phe
            435                 440                 445

Arg Pro His Asn Arg Asp Lys Thr Ile Thr Asn Leu Tyr Leu Val Gly
450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490
```

<210> SEQ ID NO 17
<211> LENGTH: 1149
<212> TYPE: DNA
<213> ORGANISM: Pantoea ananatis

<400> SEQUENCE: 17

```
atgcaaccgc attatgatct gattctcgtg ggggctggac tcgcgaatgg ccttatcgcc    60
ctgcgtcttc agcagcagca acctgatatg cgtattttgc ttatcgacgc cgcaccccag   120
gcgggcggaa atcatacgtg gtcatttcac cacgatgatt tgactgagag ccaacatcgt   180
tggatagcgc cgctggtggt tcatcactgg cccgactatc aggtgcgctt cccacacgc   240
cgtcgtaagc tgaacagcgg ctacttctgt attacttctc agcgtttcgc tgaggtttta   300
ctgcgacagt ttggcccgca cttgtggatg gataccgcgg tcgcagaggt taatgcggaa   360
tctgttcggt tgaaaaaggg tcaggttatc ggtgcccgcg cggtgattga cgggcgggt   420
tatgcggcaa actcagcact gagcgtgggc ttccaggcgt ttattggcca ggaatggcga   480
ttgagccgcc cgcatggttt atcgtctccc attatcatgg atgccacggt cgatcagcaa   540
aatggttatc gcttcgtgta cagcctgccg ctctcgccga ccagattgtt aattgaagac   600
acgcactata tcgataatgc gacattagat cctgaacgcg cgcggcaaaa tatttgcgac   660
tatgccgcgc aacagggttg gcagcttcag actctgctgc gtgaagaaca gggcgcctta   720
cccattaccc tgtcgggcaa tgccgacgca ttctggcagc agcgcccct ggcctgtagt   780
ggattacgtg ccggtctgtt ccatcctacc accggctatt cactgccgct ggcggttgcc   840
gtggccgacc gctgagcgc acttgatgtc tttacgtcgg cctcaattca tcaggccatt   900
acgcattttg cccgcgagcg ctggcagcag cagcgctttt tccgcatgct gaatcgcatg   960
ctgtttttag ccgggcccgc cgatttacgc tggcgggtta tgcagcgttt ttatggttta  1020
cctgaagatt taattgcccg tttttatgcg ggaaaactca cgctgaccga tcggctacgt  1080
attctgagcg gcaagccgcc tgttccggta ttagcagcat tgcaagccat tatgacgact  1140
catcgttaa                                                          1149
```

<210> SEQ ID NO 18
<211> LENGTH: 382
<212> TYPE: PRT
<213> ORGANISM: Pantoea ananatis

<400> SEQUENCE: 18

Met Gln Pro His Tyr Asp Leu Ile Leu Val Gly Ala Gly Leu Ala Asn
1               5                   10                  15

Gly Leu Ile Ala Leu Arg Leu Gln Gln Gln Gln Pro Asp Met Arg Ile
            20                  25                  30

Leu Leu Ile Asp Ala Ala Pro Gln Ala Gly Gly Asn His Thr Trp Ser
        35                  40                  45

Phe His His Asp Asp Leu Thr Glu Ser Gln His Arg Trp Ile Ala Pro
    50                  55                  60

Leu Val Val His His Trp Pro Asp Tyr Gln Val Arg Phe Pro Thr Arg
65                  70                  75                  80

Arg Arg Lys Leu Asn Ser Gly Tyr Phe Cys Ile Thr Ser Gln Arg Phe
                85                  90                  95

Ala Glu Val Leu Leu Arg Gln Phe Gly Pro His Leu Trp Met Asp Thr
            100                 105                 110

Ala Val Ala Glu Val Asn Ala Glu Ser Val Arg Leu Lys Lys Gly Gln
        115                 120                 125

```
Val Ile Gly Ala Arg Ala Val Ile Asp Gly Arg Gly Tyr Ala Ala Asn
    130                 135                 140

Ser Ala Leu Ser Val Gly Phe Gln Ala Phe Ile Gly Gln Glu Trp Arg
145                 150                 155                 160

Leu Ser Arg Pro His Gly Leu Ser Ser Pro Ile Ile Met Asp Ala Thr
            165                 170                 175

Val Asp Gln Gln Asn Gly Tyr Arg Phe Val Tyr Ser Leu Pro Leu Ser
        180                 185                 190

Pro Thr Arg Leu Leu Ile Glu Asp Thr His Tyr Ile Asp Asn Ala Thr
    195                 200                 205

Leu Asp Pro Glu Arg Ala Arg Gln Asn Ile Cys Asp Tyr Ala Ala Gln
210                 215                 220

Gln Gly Trp Gln Leu Gln Thr Leu Leu Arg Glu Gln Gly Ala Leu
225                 230                 235                 240

Pro Ile Thr Leu Ser Gly Asn Ala Asp Ala Phe Trp Gln Gln Arg Pro
            245                 250                 255

Leu Ala Cys Ser Gly Leu Arg Ala Gly Leu Phe His Pro Thr Thr Gly
        260                 265                 270

Tyr Ser Leu Pro Leu Ala Val Ala Val Ala Asp Arg Leu Ser Ala Leu
    275                 280                 285

Asp Val Phe Thr Ser Ala Ser Ile His Gln Ala Ile Thr His Phe Ala
290                 295                 300

Arg Glu Arg Trp Gln Gln Gln Arg Phe Phe Arg Met Leu Asn Arg Met
305                 310                 315                 320

Leu Phe Leu Ala Gly Pro Ala Asp Leu Arg Trp Arg Val Met Gln Arg
            325                 330                 335

Phe Tyr Gly Leu Pro Glu Asp Leu Ile Ala Arg Phe Tyr Ala Gly Lys
        340                 345                 350

Leu Thr Leu Thr Asp Arg Leu Arg Ile Leu Ser Gly Lys Pro Pro Val
    355                 360                 365

Pro Val Leu Ala Ala Leu Gln Ala Ile Met Thr Thr His Arg
370                 375                 380

<210> SEQ ID NO 19
<211> LENGTH: 777
<212> TYPE: DNA
<213> ORGANISM: Nostoc sp.

<400> SEQUENCE: 19
atggttcagt gtcaaccatc atctctgcat tcagaaaaac tggtgttatt gtcatcgaca      60
atcagagatg ataaaaatat taataagggt atatttattg cctgctttat cttatttta     120 tgggcaatta gttaatcttt attactctca atagatacat ccataattca taagagctta     180
ttaggtatag ccatgctttg gcagaccttc ttatatacag gtttatttat tactgctcat     240
gatgccatgc acggcgtagt ttatcccaaa atcccagaa taaataattt tataggtaag     300
ctcactctaa tcttgtatgg actactccct tataaagatt tattgaaaaa acattggtta     360
caccacggac atcctggtac tgatttagac cctgattatt acaatggtca tccccaaaac     420
ttctttcttt ggtatctaca ttttatgaag tcttattggc gatggacgca aattttcgga     480
ttagtgatga ttttcatgg acttaaaaat ctggtgcata taccagaaaa taatttaatt     540
atattttgga tgataccttc tatttaagt tcagtacaac tatttatttt ggtacatttt     600
ttgcctcata aaaagctaga aggtggttat actaaccccc attgtgcgcg cagtatccca     660
```

```
ttacctcttt tttggtcttt tgttacttgt tatcacttcg gctaccacaa ggaacatcac      720
gaataccctc aacttccttg gtggaaatta cctgaagctc acaaaatatc tttataa        777
```

<210> SEQ ID NO 20
<211> LENGTH: 258
<212> TYPE: PRT
<213> ORGANISM: Nostoc sp.

<400> SEQUENCE: 20

```
Met Val Gln Cys Gln Pro Ser Ser Leu His Ser Glu Lys Leu Val Leu
 1               5                  10                  15

Leu Ser Ser Thr Ile Arg Asp Asp Lys Asn Ile Asn Lys Gly Ile Phe
            20                  25                  30

Ile Ala Cys Phe Ile Leu Phe Leu Trp Ala Ile Ser Leu Ile Leu Leu
        35                  40                  45

Leu Ser Ile Asp Thr Ser Ile Ile His Lys Ser Leu Leu Gly Ile Ala
    50                  55                  60

Met Leu Trp Gln Thr Phe Leu Tyr Thr Gly Leu Phe Ile Thr Ala His
65                  70                  75                  80

Asp Ala Met His Gly Val Val Tyr Pro Lys Asn Pro Arg Ile Asn Asn
                85                  90                  95

Phe Ile Gly Lys Leu Thr Leu Ile Leu Tyr Gly Leu Leu Pro Tyr Lys
            100                 105                 110

Asp Leu Leu Lys Lys His Trp Leu His His Gly His Pro Gly Thr Asp
        115                 120                 125

Leu Asp Pro Asp Tyr Tyr Asn Gly His Pro Gln Asn Phe Phe Leu Trp
    130                 135                 140

Tyr Leu His Phe Met Lys Ser Tyr Trp Arg Trp Thr Gln Ile Phe Gly
145                 150                 155                 160

Leu Val Met Ile Phe His Gly Leu Lys Asn Leu Val His Ile Pro Glu
                165                 170                 175

Asn Asn Leu Ile Ile Phe Trp Met Ile Pro Ser Ile Leu Ser Ser Val
            180                 185                 190

Gln Leu Phe Tyr Phe Gly Thr Phe Leu Pro His Lys Lys Leu Glu Gly
        195                 200                 205

Gly Tyr Thr Asn Pro His Cys Ala Arg Ser Ile Pro Leu Pro Leu Phe
    210                 215                 220

Trp Ser Phe Val Thr Cys Tyr His Phe Gly Tyr His Lys Glu His His
225                 230                 235                 240

Glu Tyr Pro Gln Leu Pro Trp Trp Lys Leu Pro Glu Ala His Lys Ile
                245                 250                 255

Ser Leu
```

<210> SEQ ID NO 21
<211> LENGTH: 528
<212> TYPE: DNA
<213> ORGANISM: Pantoea ananatis

<400> SEQUENCE: 21

```
atgttgtgga tttggaatgc cctgatcgtt tcgttaccg tgattggcat ggaagtggtt       60
gctgcactgg cacacaaata catcatgcac ggctggggtt ggggatggca tctttcacat    120
catgaaccgc gtaaaggtgc gtttgaagtt aacgatcttt atgccgtggt ttttgctgca    180
ttatcgatcc tgctgattta tctgggcagt acaggaatgt ggccgctcca gtggattggc    240
gcaggtatga cggcgtatgg attactctat tttatggtgc acgacgggct ggtgcatcaa    300
```

```
cgttggccat tccgctatat tccacgcaag ggctacctca aacggttgta tatggcgcac    360
cgtatgcatc acgccgtcag gggcaaagaa ggttgtgttt cttttggctt cctctatgcg    420
ccgcccctgt caaaacttca ggcgacgctc cgggaaagac atggcgctag agcgggcgct    480
gccagagatg cgcagggcgg ggaggatgag cccgcatccg gaagtaa                  528
```

<210> SEQ ID NO 22
<211> LENGTH: 175
<212> TYPE: PRT
<213> ORGANISM: Pantoea ananatis

<400> SEQUENCE: 22

```
Met Leu Trp Ile Trp Asn Ala Leu Ile Val Phe Val Thr Val Ile Gly
1               5                   10                  15

Met Glu Val Val Ala Ala Leu Ala His Lys Tyr Ile Met His Gly Trp
            20                  25                  30

Gly Trp Gly Trp His Leu Ser His His Glu Pro Arg Lys Gly Ala Phe
        35                  40                  45

Glu Val Asn Asp Leu Tyr Ala Val Val Phe Ala Ala Leu Ser Ile Leu
    50                  55                  60

Leu Ile Tyr Leu Gly Ser Thr Gly Met Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Gly Ala Arg Ala Gly Ala
145                 150                 155                 160

Ala Arg Asp Ala Gln Gly Gly Glu Asp Glu Pro Ala Ser Gly Lys
                165                 170                 175
```

<210> SEQ ID NO 23
<211> LENGTH: 1119
<212> TYPE: DNA
<213> ORGANISM: Corynebacterium glutamicum

<400> SEQUENCE: 23

```
atggacaatg gcatgacaat caccacagaa cattcaactc atcctgatct tgatttcaat    60
gatgagattt tcgggaact aaaccgcatc tgcgcttcgc tatctcaaca gtgcagcaca   120
tatcaaccag agttccgtac ctgcctagat gctgcttttcc aagctttgcg aggtggcaag   180
ttaatccgcc ctcgaatgct actggggcta caacacgc ttgtagacga tgacattgag    240
gtcaaactca acaccgtttt acaggtagca gtggctttag aactactgca tttttccctt   300
ttggttcatg acgatgttat tgacggagac ctctatcgcc gaggcaaact taatttatt    360 gggcagattc tcatgcatcg cacacctgaa agttttgcac aaatccagcg cgatccagag   420
catctagatt gggcacaatc taatggactg cttatgggaa atcttttctc tgctgccacc   480
catcaaatct tcgcgcgcct tgaccttcca catcaccaac gggttcgact tttagattta   540
ctcaaccaca cgataaatga cactattgtg ggtgagtttc ttgatgtggg attaagcagc   600
aaagccatca gccccaatat ggacattgct ctagaaatga gtcggctaaa aacagccaca   660
```

```
tacactttg aacttccaat gagagcagcg gcaattctcg cggaactacc tcaggagatt      720
gaaacaaaga taggtgagat aggcacaaac ttgggcatcg cttatcaatt gcaggacgat      780
tacttatcta cttttggtga cgcagccgaa cacggcaaag atgcctttc tgaccttcga       840 gaaggaaaag aaactacaat tatcgccttc gctcgagata ctgctaaatg gactgatatt      900
caagacaact tcggctccgc agatctgagc acctctcagg cagagcgaat tcaacatctt      960
ctcatacagt gtggagcaaa gaatcactcc ttgaatgcca tctccgacca cttaaatatc     1020
tgccgttcga tgatcaaaac actaagcccc caggtagatc ccaaggctca aaatttatta     1080
cttaaacaag ttgagcaact agccagccgc aaatcttag                            1119
```

<210> SEQ ID NO 24
<211> LENGTH: 372
<212> TYPE: PRT
<213> ORGANISM: Corynebacterium glutamicum

<400> SEQUENCE: 24

```
Met Asp Asn Gly Met Thr Ile Thr Thr Glu His Ser Thr His Pro Asp
1               5                   10                  15

Leu Asp Phe Asn Asp Glu Ile Tyr Arg Glu Leu Asn Arg Ile Cys Ala
            20                  25                  30

Ser Leu Ser Gln Gln Cys Ser Thr Tyr Gln Pro Glu Phe Arg Thr Cys
        35                  40                  45

Leu Asp Ala Ala Phe Gln Ala Leu Arg Gly Gly Lys Leu Ile Arg Pro
    50                  55                  60

Arg Met Leu Leu Gly Leu Tyr Asn Thr Leu Val Asp Asp Ile Glu
65                  70                  75                  80

Val Lys Leu Asn Thr Val Leu Gln Val Ala Val Ala Leu Glu Leu Leu
                85                  90                  95

His Phe Ser Leu Leu Val His Asp Asp Val Ile Asp Gly Asp Leu Tyr
            100                 105                 110

Arg Arg Gly Lys Leu Asn Phe Ile Gly Gln Ile Leu Met His Arg Thr
        115                 120                 125

Pro Glu Ser Phe Ala Gln Ile Gln Arg Asp Pro Glu His Leu Asp Trp
    130                 135                 140

Ala Gln Ser Asn Gly Leu Leu Met Gly Asn Leu Phe Leu Ala Ala Thr
145                 150                 155                 160

His Gln Ile Phe Ala Arg Leu Asp Leu Pro His His Gln Arg Val Arg
                165                 170                 175

Leu Leu Asp Leu Leu Asn His Thr Ile Asn Asp Thr Ile Val Gly Glu
            180                 185                 190

Phe Leu Asp Val Gly Leu Ser Ser Lys Ala Ile Ser Pro Asn Met Asp
        195                 200                 205

Ile Ala Leu Glu Met Ser Arg Leu Lys Thr Ala Thr Tyr Thr Phe Glu
    210                 215                 220

Leu Pro Met Arg Ala Ala Ala Ile Leu Ala Glu Leu Pro Gln Glu Ile
225                 230                 235                 240

Glu Thr Lys Ile Gly Glu Ile Gly Thr Asn Leu Gly Ile Ala Tyr Gln
                245                 250                 255

Leu Gln Asp Asp Tyr Leu Ser Thr Phe Gly Asp Ala Ala Glu His Gly
            260                 265                 270

Lys Asp Ala Phe Ser Asp Leu Arg Glu Gly Lys Glu Thr Thr Ile Ile
        275                 280                 285
```

Ala Phe Ala Arg Asp Thr Ala Lys Trp Thr Asp Ile Gln Asp Asn Phe
290                 295                 300

Gly Ser Ala Asp Leu Ser Thr Ser Gln Ala Glu Arg Ile Gln His Leu
305                 310                 315                 320

Leu Ile Gln Cys Gly Ala Lys Asn His Ser Leu Asn Ala Ile Ser Asp
            325                 330                 335

His Leu Asn Ile Cys Arg Ser Met Ile Lys Thr Leu Ser Pro Gln Val
            340                 345                 350

Asp Pro Lys Ala Gln Asn Leu Leu Lys Gln Val Glu Gln Leu Ala
        355                 360                 365

Ser Arg Lys Ser
    370

<210> SEQ ID NO 25
<211> LENGTH: 915
<212> TYPE: DNA
<213> ORGANISM: Corynebacterium glutamicum

<400> SEQUENCE: 25
atgacacacc aaaattcgcc tctcttcctt aaaagtgcac tgagacttta caatcgggcc    60
tcattcaagg cttacataaa agtgatcgaa gaatattcga cgagcttcag tctgtctacg   120
tggttgctat ccccacgcat acgaaatgac atacgaaatc tctatgcagt agttcgtatc   180
gccgatgaga ttgtcgacgg cactgcacat gccgctggtt gctcaactgc aaaatcgaa    240 gagattctcg atgcctatga aattgcggtt cttgcagcac acaacaacg cttcaacaca    300 gatcttgttt tacaagctta tggtgaaact gcccgacgct gtgatttcga acaagagcat   360
gtaatagcct tctttgcatc aatgcgtaag gacctcaaag ctaatacaca cgacccagat   420
agcttcacaa cgtatgtcta tggctccgcg gaagttatag gcctgctttg tctcagcgtt   480
ttcaaccaag gtagaacgat tagcaaaaaa cggctagaga ttatgcaaaa cggagcccgc   540
tcattgggag cggcattcca gaaaattaac tttctccgtg acttggcaga agatcagcaa   600
aatttgggcc gattttattt ccccaaaacc agccaaggaa ctcttactaa agaacaaaaa   660
gaagatctca tcgctgatat ccgtcaagac ctagcaattg cccacgatgc atttccagaa   720
ataccagtgc aggctcgcat cggagtgatc tctgcttatt tgctctttca aaaactcact   780
gaccgaattg aggctactcc taccgccgat ttattgcggg agcgaatcag agttccactt   840
catatcaaac tctctacact cgctagagcc acgatgaaag gtctatctat gagcatctac   900
agaaagaatt cgtga                                                    915

<210> SEQ ID NO 26
<211> LENGTH: 304
<212> TYPE: PRT
<213> ORGANISM: Corynebacterium glutamicum

<400> SEQUENCE: 26

Met Thr His Gln Asn Ser Pro Leu Phe Leu Lys Ser Ala Leu Arg Leu
1               5                   10                  15

Tyr Asn Arg Ala Ser Phe Lys Ala Ser His Lys Val Ile Glu Glu Tyr
            20                  25                  30

Ser Thr Ser Phe Ser Leu Ser Thr Trp Leu Leu Ser Pro Arg Ile Arg
        35                  40                  45

Asn Asp Ile Arg Asn Leu Tyr Ala Val Val Arg Ile Ala Asp Glu Ile
    50                  55                  60

Val Asp Gly Thr Ala His Ala Ala Gly Cys Ser Thr Ala Lys Ile Glu

```
                65                  70                  75                  80
Glu Ile Leu Asp Ala Tyr Glu Ile Ala Val Leu Ala Ala Pro Gln Gln
                        85                  90                  95

Arg Phe Asn Thr Asp Leu Val Leu Gln Ala Tyr Gly Glu Thr Ala Arg
                100                 105                 110

Arg Cys Asp Phe Glu Gln Glu His Val Ile Ala Phe Phe Ala Ser Met
                115                 120                 125

Arg Lys Asp Leu Lys Ala Asn Thr His Asp Pro Asp Ser Phe Thr Thr
                130                 135                 140

Tyr Val Tyr Gly Ser Ala Glu Val Ile Gly Leu Leu Cys Leu Ser Val
145                 150                 155                 160

Phe Asn Gln Gly Arg Thr Ile Ser Lys Lys Arg Leu Glu Ile Met Gln
                        165                 170                 175

Asn Gly Ala Arg Ser Leu Gly Ala Ala Phe Gln Lys Ile Asn Phe Leu
                180                 185                 190

Arg Asp Leu Ala Glu Asp Gln Gln Asn Leu Gly Arg Phe Tyr Phe Pro
                195                 200                 205

Lys Thr Ser Gln Gly Thr Leu Thr Lys Glu Gln Lys Glu Asp Leu Ile
                210                 215                 220

Ala Asp Ile Arg Gln Asp Leu Ala Ile Ala His Asp Ala Phe Pro Glu
225                 230                 235                 240

Ile Pro Val Gln Ala Arg Ile Gly Val Ile Ser Ala Tyr Leu Leu Phe
                        245                 250                 255

Gln Lys Leu Thr Asp Arg Ile Glu Ala Thr Pro Thr Ala Asp Leu Leu
                260                 265                 270

Arg Glu Arg Ile Arg Val Pro Leu His Ile Lys Leu Ser Thr Leu Ala
                275                 280                 285

Arg Ala Thr Met Lys Gly Leu Ser Met Ser Ile Tyr Arg Lys Asn Ser
                290                 295                 300
```

<210> SEQ ID NO 27
<211> LENGTH: 1647
<212> TYPE: DNA
<213> ORGANISM: Corynebacterium glutamicum

<400> SEQUENCE: 27

```
atgaaggtct cgactaaaac tccacgctcc tcaggtaccg ccgtagtcat aggcgcaggt    60
gttgctggtt tagccacttc tgcactttta gcacgtgatg gctggcaagt aactgttttg   120
gaaaaaaata ctgatgtcgg tggccgagct ggatcgcttg aaatatcagg ctttcctggc   180
tttcgatggg ataccggacc tcttggtac ctcatgcccg aggcctttga ccatttcttc   240
gcacttttg gtgcatgtac ttctgattat ctcgatttgg tagaattaac gcctggttat   300
cgagtttttt ctggcacaca tgacgctgtc gatgtcccca ctgggcgtga agaagcaatt   360
gcgctattcg aatccatcga acccggcgcg ggtgcaaaac taggaaatta tcttgatagc   420
gcggcagacg cctatgacat tgccattgat agattccttt ataataattt ctccacgtta   480
ggcccgctgc ttcaccggga tgtactgacc cgagctggcc gactgttttc tctactgacc   540
cgttctttac aaaagtacgt aaatagtcaa ttcagtagcc cggtgttgcg ccagatccta   600
acctatccag cagtcttcct gtcttcccga cccactacta ccccatcgat gtaccacttg   660
atgagtcata ccgatttggt gcagggagtg aaataccctca taggtggttt tactgcagtg   720
gttaacgctc tgcatcagtt agcgctggaa aacgggggttg agtttcaact cgattctgag   780
gtcatttcca tcaacactgc ttcatcgagg ggcaacacaa gcgccacagg tgtgagcttg   840
```

-continued

```
cttcacaaca gaaaagtgca aaatctagat gcggatcttg tggtttcagc aggcgaccta    900
caccatacag aaaataatct gcttccccgg gaacttcgaa cctatcccga acgatattgg    960
tccaatcgca atcctggaat tggagcggta ttaatcctcc tgggcgtaaa aggagagtta   1020
ccccagctcg accatcacaa ccttttcttc agtgaagatt ggacagatga ttttgctgta   1080
gttttcgacg ggcctcaact tacccgcccc cacaatgcat caaattccat ttatgtctcc   1140
aagccttcaa cgtccgaaga cggcgttgca cctgctggac gaaaaacctt tttgtttta    1200 attccgacca aggcctctag cagcatcggc cacggtgatg cgtatatgca gtcggcttca   1260
gcatccgtgg aaacaatcgc gtcacatgca atcaatcaaa ttgctacgca agccggcatc   1320
cctgacctca ctgaccgaat tgtggtcaaa cgcaccattg ccctgcgga ttttgagcac    1380 cgctaccatt catgggtagg cagtgcgctg gtccagcac ataccctcag acagtccgct    1440
ttcttaagag ggcgcaatag ctcccgcaag gtcaataacc tcttctattc cggtgccacc   1500
accgtcccgg gtgtaggaat acccatgtgt taatttctg ccagaatat tattaagcgt     1560 ttacatgccg ataccagtgc aggaccactg cccgaaccat tgccgcctaa aacgacacca   1620
tctcaaaaga cctcatacga tcattaa                                       1647
```

<210> SEQ ID NO 28
<211> LENGTH: 548
<212> TYPE: PRT
<213> ORGANISM: Corynebacterium glutamicum

<400> SEQUENCE: 28

```
Met Lys Val Ser Thr Lys Thr Pro Arg Ser Ser Gly Thr Ala Val Val
1               5                   10                  15

Ile Gly Ala Gly Val Ala Gly Leu Ala Thr Ser Ala Leu Leu Ala Arg
            20                  25                  30

Asp Gly Trp Gln Val Thr Val Leu Glu Lys Asn Thr Asp Val Gly Gly
        35                  40                  45

Arg Ala Gly Ser Leu Glu Ile Ser Gly Phe Pro Gly Phe Arg Trp Asp
    50                  55                  60

Thr Gly Pro Ser Trp Tyr Leu Met Pro Glu Ala Phe Asp His Phe Phe
65                  70                  75                  80

Ala Leu Phe Gly Ala Cys Thr Ser Asp Tyr Leu Asp Leu Val Glu Leu
                85                  90                  95

Thr Pro Gly Tyr Arg Val Phe Ser Gly Thr His Asp Ala Val Asp Val
            100                 105                 110

Pro Thr Gly Arg Glu Glu Ala Ile Ala Leu Phe Glu Ser Ile Glu Pro
        115                 120                 125

Gly Ala Gly Ala Lys Leu Gly Asn Tyr Leu Asp Ser Ala Ala Asp Ala
    130                 135                 140

Tyr Asp Ile Ala Ile Asp Arg Phe Leu Tyr Asn Asn Phe Ser Thr Leu
145                 150                 155                 160

Gly Pro Leu Leu His Arg Asp Val Leu Thr Arg Ala Gly Arg Leu Phe
                165                 170                 175

Ser Leu Leu Thr Arg Ser Leu Gln Lys Tyr Val Asn Ser Gln Phe Ser
            180                 185                 190

Ser Pro Val Leu Arg Gln Ile Leu Thr Tyr Pro Ala Val Phe Leu Ser
        195                 200                 205

Ser Arg Pro Thr Thr Thr Pro Ser Met Tyr His Leu Met Ser His Thr
    210                 215                 220
```

```
Asp Leu Val Gln Gly Val Lys Tyr Pro Ile Gly Gly Phe Thr Ala Val
225                 230                 235                 240

Val Asn Ala Leu His Gln Leu Ala Leu Glu Asn Gly Val Glu Phe Gln
                245                 250                 255

Leu Asp Ser Glu Val Ile Ser Ile Asn Thr Ala Ser Ser Arg Gly Asn
            260                 265                 270

Thr Ser Ala Thr Gly Val Ser Leu Leu His Asn Arg Lys Val Gln Asn
        275                 280                 285

Leu Asp Ala Asp Leu Val Val Ser Ala Gly Asp Leu His His Thr Glu
    290                 295                 300

Asn Asn Leu Leu Pro Arg Glu Leu Arg Thr Tyr Pro Glu Arg Tyr Trp
305                 310                 315                 320

Ser Asn Arg Asn Pro Gly Ile Gly Ala Val Leu Ile Leu Leu Gly Val
                325                 330                 335

Lys Gly Glu Leu Pro Gln Leu Asp His His Asn Leu Phe Phe Ser Glu
            340                 345                 350

Asp Trp Thr Asp Asp Phe Ala Val Val Phe Asp Gly Pro Gln Leu Thr
        355                 360                 365

Arg Pro His Asn Ala Ser Asn Ser Ile Tyr Val Ser Lys Pro Ser Thr
    370                 375                 380

Ser Glu Asp Gly Val Ala Pro Ala Gly Tyr Glu Asn Leu Phe Val Leu
385                 390                 395                 400

Ile Pro Thr Lys Ala Ser Ser Ile Gly His Gly Asp Ala Tyr Met
                405                 410                 415

Gln Ser Ala Ser Ala Ser Val Glu Thr Ile Ala Ser His Ala Ile Asn
            420                 425                 430

Gln Ile Ala Thr Gln Ala Gly Ile Pro Asp Leu Thr Asp Arg Ile Val
        435                 440                 445

Val Lys Arg Thr Ile Gly Pro Ala Asp Phe Glu His Arg Tyr His Ser
    450                 455                 460

Trp Val Gly Ser Ala Leu Gly Pro Ala His Thr Leu Arg Gln Ser Ala
465                 470                 475                 480

Phe Leu Arg Gly Arg Asn Ser Ser Arg Lys Val Asn Asn Leu Phe Tyr
                485                 490                 495

Ser Gly Ala Thr Thr Val Pro Gly Val Gly Ile Pro Met Cys Leu Ile
            500                 505                 510

Ser Ala Glu Asn Ile Ile Lys Arg Leu His Ala Asp Thr Ser Ala Gly
        515                 520                 525

Pro Leu Pro Glu Pro Leu Pro Lys Thr Thr Pro Ser Gln Lys Thr
    530                 535                 540

Ser Tyr Asp His
545

<210> SEQ ID NO 29
<211> LENGTH: 735
<212> TYPE: DNA
<213> ORGANISM: Brevundimonas aurantiaca

<400> SEQUENCE: 29
atgaccgccg ccgtcgccga gccacgcacc gtcccgcgcc agacctggat cggtctgacc      60
ctggcgggaa tgatcgtggc gggatgggcg ttctgcatg tctacggcgt ctattttcac     120
cgatgggggc cgttgaccct ggtgatcgcc ccggcgatcg tggcggtcca gacctggttg     180
tcggtcggcc ttttcatcgt cgcccatgac gccatgcacg gctccctggc gccgggacgg     240
```

-continued

```
ccgcggctga acgccgcagt cggccggctg accctggggc tctatgcggg cttccgcttc    300
gatcggctga agacggcgca ccacgcccac cacgccgcgc cggcacggc cgacgacccg    360 gattttcacg ccccggcgcc ccgcgccttc cttccctggt tcctgaactt ctttcgcacc    420
tatttcggct ggcgcgagat ggcggtcctg accgccctgg tcctgatcgc cctcttcggc    480
ctgggggcgc ggccggccaa tctcctgacc ttctgggccg cgccggccct gctttcagcg    540
cttcagctct tcaccttcgg cacctggctg ccgcaccgcc acaccgacca gccgttcgcc    600
gacgcgcacc acgcccgcag cagcggctac ggccccgtgc tttccctgct cacctgtttc    660
cacttcggcc gccaccacga acaccatctg agccctggc ggccctggtg gcgtctgtgg    720
cgcggcgagt cttga                                                    735
```

<210> SEQ ID NO 30
<211> LENGTH: 244
<212> TYPE: PRT
<213> ORGANISM: Brevundimonas aurantiaca

<400> SEQUENCE: 30

```
Met Thr Ala Ala Val Ala Glu Pro Arg Thr Val Pro Arg Gln Thr Trp
1               5                   10                  15

Ile Gly Leu Thr Leu Ala Gly Met Ile Val Ala Gly Trp Ala Val Leu
            20                  25                  30

His Val Tyr Gly Val Tyr Phe His Arg Trp Gly Pro Leu Thr Leu Val
        35                  40                  45

Ile Ala Pro Ala Ile Val Ala Val Gln Thr Trp Leu Ser Val Gly Leu
    50                  55                  60

Phe Ile Val Ala His Asp Ala Met His Gly Ser Leu Ala Pro Gly Arg
65                  70                  75                  80

Pro Arg Leu Asn Ala Ala Val Gly Arg Leu Thr Leu Gly Leu Tyr Ala
                85                  90                  95

Gly Phe Arg Phe Asp Arg Leu Lys Thr Ala His His Ala His His Ala
            100                 105                 110

Ala Pro Gly Thr Ala Asp Asp Pro Asp Phe His Ala Pro Ala Pro Arg
        115                 120                 125

Ala Phe Leu Pro Trp Phe Leu Asn Phe Phe Arg Thr Tyr Phe Gly Trp
    130                 135                 140

Arg Glu Met Ala Val Leu Thr Ala Leu Val Leu Ile Ala Leu Phe Gly
145                 150                 155                 160

Leu Gly Ala Arg Pro Ala Asn Leu Leu Thr Phe Trp Ala Ala Pro Ala
                165                 170                 175

Leu Leu Ser Ala Leu Gln Leu Phe Thr Phe Gly Thr Trp Leu Pro His
            180                 185                 190

Arg His Thr Asp Gln Pro Phe Ala Asp Ala His Ala Arg Ser Ser
        195                 200                 205

Gly Tyr Gly Pro Val Leu Ser Leu Leu Thr Cys Phe His Phe Gly Arg
    210                 215                 220

His His Glu His His Leu Ser Pro Trp Arg Pro Trp Trp Arg Leu Trp
225                 230                 235                 240

Arg Gly Glu Ser
```

<210> SEQ ID NO 31
<211> LENGTH: 80
<212> TYPE: DNA
<213> ORGANISM: Artificial Sequence
<220> FEATURE:

```
<223> OTHER INFORMATION: primer

<400> SEQUENCE: 31
gaatcgtgag cggataacaa tttcacacaa ggagactgcc atgttgtgga tttggaatgc      60
cctgatcgtt ttcgttaccg                                                  80

<210> SEQ ID NO 32
<211> LENGTH: 31
<212> TYPE: DNA
<213> ORGANISM: Artificial Sequence
<220> FEATURE:
<223> OTHER INFORMATION: primer

<400> SEQUENCE: 32
ttacttcccg gatgcgggct catcctcccc g                                     31

<210> SEQ ID NO 33
<211> LENGTH: 2062
<212> TYPE: DNA
<213> ORGANISM: Pantoea ananatis

<400> SEQUENCE: 33
tttgcgcctg caacgtaggt tgcgtggtgc ttggagtggt gaagctccat gatttcagcg      60
gcgatgtgtg gctcgagagc atcgtatgcg tagtcgagtt ctgggagttc gtatacagcc     120
atgggtaaaa aatcctttcg taggtttccg caccgagcat atacatcttt tgaaaatccg     180
tcagatggcg cttcgcaaaa gtacttggtg cgacacttcc caatgatagg cctttttgtt     240
gatattgcaa cgaaattttt cagccgacct atttatcggg tagtgggtca caagcccgga     300
ataattggca gctaagtagg gttgaagggc ataaggcttc ctcaatttc gaaaggaaca      360 ttcctgttat gcaaccgcat tatgatctga ttctcgtggg ggctggactc gcgaatggcc     420
ttatcgccct gcgtcttcag cagcagcaac ctgatatgcg tatttttgctt atcgacgccg    480 caccccaggc gggcggaaat catacgtggt catttcacca cgatgatttg actgagagcc     540
aacatcgttg gatagcgccg ctggtggttc atcactggcc cgactatcag gtgcgctttc     600
ccacacgccg tcgtaagctg aacagcggct acttctgtat tacttctcag cgtttcgctg     660 aggtttact gcgacagttt ggcccgcact tgtggatgga taccgcggtc gcagaggtta      720
atgcggaatc tgttcggttg aaaaagggtc aggttatcgg tgcccgcgcg gtgattgacg     780
ggcggggtta tgcggcaaac tcagcactga gcgtgggctt ccaggcgttt attggccagg     840
aatggcgatt gagccgcccg catggtttat cgtctcccat tatcatggat gccacggtcg     900
atcagcaaaa tggttatcgc ttcgtgtaca gcctgccgct ctcgccgacc agattgttaa     960
ttgaagacac gcactatatc gataatgcga cattagatcc tgaacgcgcg cggcaaaata    1020
tttgcgacta tgccgcgcaa cagggttggc agcttcagac tctgctgcgt gaagaacagg    1080
gcgccttacc cattaccctg tcgggcaatg ccgacgcatt ctggcagcag cgcccctgg    1140 cctgtagtgg attacgtgcc ggtctgttcc atcctaccac cggctattca ctgccgctgg    1200
cggttgccgt ggccgaccgc ctgagcgcac ttgatgtctt tacgtcggcc tcaattcatc    1260
aggccattac gcattttgcc cgcgagcgct ggcagcagca gcgcttttc cgcatgctga    1320 atcgcatgct gttttagcc gggcccgccg atttacgctg gcgggttatg cagcgttttt    1380
atggtttacc tgaagattta attgcccgtt tttatgcggg aaaactcacg ctgaccgatc    1440
ggctacgtat tctgagcggc aagccgcctg ttccggtatt agcagcattg caagccatta    1500
tgacgactca tcgttaagaa aggaggccct tcagatgttg tggatttgga atgccctgat    1560
```

```
cgttttcgtt accgtgattg gcatggaagt ggttgctgca ctggcacaca aatacatcat    1620
gcacggctgg ggttggggat ggcatctttc acatcatgaa ccgcgtaaag gtgcgtttga    1680
agttaacgat ctttatgccg tggttttgc tgcattatcg atcctgctga tttatctggg     1740
cagtacagga atgtggccgc tccagtggat tggcgcaggt atgacggcgt atggattact    1800
ctattttatg gtgcacgacg ggctggtgca tcaacgttgg ccattccgct atattccacg    1860
caagggctac ctcaaacggt tgtatatggc gcaccgtatg catcacgccg tcaggggcaa    1920
agaaggttgt gtttcttttg cttcctcta tgcgccgccc ctgtcaaaac ttcaggcgac     1980
gctccgggaa agacatggcg ctagagcggg cgctgccaga gatgcgcagg gcggggagga    2040
tgagcccgca tccgggaagt aa                                             2062

<210> SEQ ID NO 34
<211> LENGTH: 69
<212> TYPE: DNA
<213> ORGANISM: Artificial Sequence
<220> FEATURE:
<223> OTHER INFORMATION: primer

<400> SEQUENCE: 34
aatcccgtcg gagtggcgcg ttacctggta gcgcgccatt tgaagcctgc ttttttatac    60
taagttggc                                                            69

<210> SEQ ID NO 35
<211> LENGTH: 50
<212> TYPE: DNA
<213> ORGANISM: Artificial Sequence
<220> FEATURE:
<223> OTHER INFORMATION: primer

<400> SEQUENCE: 35
gcattccaaa tccacaacat ggcagtctcc ttgtgtgaaa ttgttatccg                50

<210> SEQ ID NO 36
<211> LENGTH: 80
<212> TYPE: DNA
<213> ORGANISM: Artificial Sequence
<220> FEATURE:
<223> OTHER INFORMATION: primer

<400> SEQUENCE: 36
acaataatct gccagttcac ggtacagcag acttagtgac tcgcgcagcg ttacttcccg    60
gatgcgggct catcctcccc                                                80

<210> SEQ ID NO 37
<211> LENGTH: 486
<212> TYPE: DNA
<213> ORGANISM: Brevundimonas sp.

<400> SEQUENCE: 37
atggcctggc tgacgtggat cgcgctgttc ctgaccgcct ttttgggcat ggaggcgttc    60
gcctggatca tgcaccgcta tgtgatgcac ggtttcctgt ggtcctggca ccgcagccat    120
catgagccgc acgatcaccc cctggagaag aacgacctgt tcgccgtggt cttcgccgcc    180
ccggccatcg tcatggtggc cgtgggtctg cacctgtggc cctgggccct gccggtcggc    240
ctggggatca cggcctatgg gatggtctat ttcttcttcc acgacggcct ggtgcaccgg    300
cggttcccga cgggctttc cggcggtcc ggcttctgga cgcggcgcat ccaggcgcac    360
```

```
cgtctgcatc acgccgtgcg cacgcgcgaa ggctgcgtct ccttcggctt tctgtgggtg    420
cggtcggcgc gggcgctgaa ggccgaactg gctcagaagc ggggctcttc cagcagcggc    480
gcctga                                                                486
```

<210> SEQ ID NO 38
<211> LENGTH: 56
<212> TYPE: DNA
<213> ORGANISM: Artificial Sequence
<220> FEATURE:
<223> OTHER INFORMATION: primer

<400> SEQUENCE: 38

```
cggataacaa tttcacacaa ggagactgcc atggcctggc tgacgtggat cgcgct    56
```

<210> SEQ ID NO 39
<211> LENGTH: 71
<212> TYPE: DNA
<213> ORGANISM: Artificial Sequence
<220> FEATURE:
<223> OTHER INFORMATION: primer

<400> SEQUENCE: 39

```
acaataatct gccagttcac ggtacagcag acttagtgac tcgcgcagcg tcaggcgccg    60
ctgctggaag a                                                          71
```

<210> SEQ ID NO 40
<211> LENGTH: 80
<212> TYPE: DNA
<213> ORGANISM: Artificial Sequence
<220> FEATURE:
<223> OTHER INFORMATION: primer

<400> SEQUENCE: 40

```
atgactcacc cggacggtat gcaaatcaaa attacccgtc aggaaattgg tgaagcctgc    60 tttttttatac taagttggca                                                80
```

<210> SEQ ID NO 41
<211> LENGTH: 56
<212> TYPE: DNA
<213> ORGANISM: Artificial Sequence
<220> FEATURE:
<223> OTHER INFORMATION: primer

<400> SEQUENCE: 41

```
agcgcgatcc acgtcagcca ggccatggca gtctccttgt gtgaaattgt tatccg    56
```

<210> SEQ ID NO 42
<211> LENGTH: 489
<212> TYPE: DNA
<213> ORGANISM: Paracoccus sp.

<400> SEQUENCE: 42

```
atgaccaatt tcctgatcgt cgtcgccacc gtgctggtga tggagttgac ggcctattcc    60
gtccaccgct ggatcatgca cggcccctg ggctggggct ggcacaagtc ccaccacgag    120
gaacacgacc acgcgctgga aaagaacgac ctgtacggcc tggtctttgc ggtgatcgcc    180
acggtgctgt tcacggtggg ctggatctgg gcgccggtcc tgtggtggat cgccttgggc    240
atgactgtct atgggctgat ctatttcgtc ctgcatgacg ggctggtgca tcagcgctgg    300
ccgttccgtt atatcccgcg caagggctat gccagacgcc tgtatcaggc ccaccgcctg    360
caccatgcgg tcgaggggcg cgaccattgc gtcagcttcg gcttcatcta tgcgccccg    420
```

```
gtcgacaagc tgaagcagga cctgaagatg tcgggcgtgc tgcgggccga ggcgcaggag    480
cgcacgtga                                                             489
```

<210> SEQ ID NO 43
<211> LENGTH: 53
<212> TYPE: DNA
<213> ORGANISM: Artificial Sequence
<220> FEATURE:
<223> OTHER INFORMATION: primer

<400> SEQUENCE: 43

```
cggataacaa tttcacacaa ggagactgcc atgaccaatt tcctgatcgt cgt            53
```

<210> SEQ ID NO 44
<211> LENGTH: 80
<212> TYPE: DNA
<213> ORGANISM: Artificial Sequence
<220> FEATURE:
<223> OTHER INFORMATION: primer

<400> SEQUENCE: 44

```
acaataatct gccagttcac ggtacagcag acttagtgac tcgcgcagcg tcacgtgcgc    60
tcctgcgcct cggcccgcag                                                 80
```

<210> SEQ ID NO 45
<211> LENGTH: 53
<212> TYPE: DNA
<213> ORGANISM: Artificial Sequence
<220> FEATURE:
<223> OTHER INFORMATION: primer

<400> SEQUENCE: 45

```
acgacgatca ggaaattggt catggcagtc tccttgtgtg aaattgttat ccg            53
```

<210> SEQ ID NO 46
<211> LENGTH: 489
<212> TYPE: DNA
<213> ORGANISM: Alcaligenes sp.

<400> SEQUENCE: 46

```
atgacgcaat tcctcattgt cgtggcgaca gtcctcgtga tggagctgac cgcctattcc    60
gtccaccgct ggattatgca cggcccccta ggctggggct ggcacaagtc ccatcacgaa   120
gagcacgacc acgcgttgga gaagaacgac ctctacggcg tcgtcttcgc ggtgctggcg   180
acgatcctct tcaccgtggg cgcctattgg tggccggtgc tgtggtggat cgccctgggc   240
atgacggtct atgggttgat ctatttcatc ctgcacgacg ggcttgtgca tcaacgctgg   300
ccgtttcggt atattccgcg gcggggctat ttccgcaggc tctaccaagc tcatcgcctg   360
caccacgcgg tcgaggggcg ggaccactgc gtcagcttcg gcttcatcta tgccccaccc   420
gtggacaagc tgaagcagga tctgaagcgg tcgggtgtcc tgcgccccca ggacgagcgt   480
ccgtcgtga                                                            489
```

<210> SEQ ID NO 47
<211> LENGTH: 58
<212> TYPE: DNA
<213> ORGANISM: Artificial Sequence
<220> FEATURE:
<223> OTHER INFORMATION: primer

<400> SEQUENCE: 47
cggataacaa tttcacacaa ggagactgcc atgacgcaat tcctcattgt cgtggcga       58

<210> SEQ ID NO 48
<211> LENGTH: 79
<212> TYPE: DNA
<213> ORGANISM: Artificial Sequence
<220> FEATURE:
<223> OTHER INFORMATION: primer

<400> SEQUENCE: 48
acaataatct gccagttcac ggtacagcag acttagtgac tcgcgcagcg tcacgacgga       60
cgctcgtcct gggggcgca                                                   79

<210> SEQ ID NO 49
<211> LENGTH: 58
<212> TYPE: DNA
<213> ORGANISM: Artificial Sequence
<220> FEATURE:
<223> OTHER INFORMATION: primer

<400> SEQUENCE: 49
tcgccacgac aatgaggaat tgcgtcatgg cagtctcctt gtgtgaaatt gttatccg        58

<210> SEQ ID NO 50
<211> LENGTH: 762
<212> TYPE: DNA
<213> ORGANISM: Nostoc punctiforme

<400> SEQUENCE: 50
atgattcagc tggaacagcc gctgagccat caggcgaaac tgaccccggt gctgcgcagc       60
aaaagccagt ttaaaggcct gtttattgcg attgtgattg tgagcgcgtg ggtgattagc      120
ctgagcctgc tgctgagcct ggatattagc aaactgaaat tttggatgct gctgccggtg      180
attctgtggc agacctttct gtataccggc ctgtttatta ccagccatga tgcgatgcat      240
ggcgtggtgt ttccgcagaa caccaaaatt aaccatctga ttggcaccct gaccctgagc      300
ctgtatggcc tgctgccgta tcagaaactg ctgaaaaaac attggctgca tcatcataac      360
ccggcgagca gcattgatcc ggattttcat aacggcaaac atcagagctt ttttgcgtgg      420
tattttcatt ttatgaaagg ctattggagc tggggccaga ttattgcgct gaccatcatt      480
tacaactttg cgaaatatat cctgcatatt ccgagcgata acctgaccta ttttttgggtg      540
ctgccgagcc tgctgagcag cctgcagctg tttttatttttg gcacctttct gccgcatagc      600
gaaccgattg gcggctatgt gcagccgcat tgcgcgcaga ccattagccg cccgatttgg      660
tggagcttta ttacctgcta tcattttggc tatcatgaag aacatcatga atatccgcat      720
attagctggt ggcagctgcc ggaaatttat aaagcgaaat aa                          762

<210> SEQ ID NO 51
<211> LENGTH: 42
<212> TYPE: DNA
<213> ORGANISM: Artificial Sequence
<220> FEATURE:
<223> OTHER INFORMATION: primer

<400> SEQUENCE: 51
tttcctgggg gtcgacatga ttcagctgga acagccgctg ag                         42

<210> SEQ ID NO 52
<211> LENGTH: 39
<212> TYPE: DNA
<213> ORGANISM: Artificial Sequence

```
<220> FEATURE:
<223> OTHER INFORMATION: primer

<400> SEQUENCE: 52
aattctgttt tctagattat ttcgctttat aaatttccg                              39

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53 gtcgacccccc aggaaaaatt ggtt                                             24

<210> SEQ ID NO 54
<211> LENGTH: 24
<212> TYPE: DNA
<213> ORGANISM: Artificial Sequence
<220> FEATURE:
<223> OTHER INFORMATION: primer

<400> SEQUENCE: 54
tctagaaaac agaatttgcc tggc                                              24

<210> SEQ ID NO 55
<211> LENGTH: 902
<212> TYPE: DNA
<213> ORGANISM: Brevundimonas aurantiaca

<400> SEQUENCE: 55
ccctgttgac aattaatcat cggctcgtat aatgtgtgga atcgtgagcg gataacaatt       60
tcacacaagg agactgccat gaccgccgcc gtcgccgagc cacgcaccgt cccgcgccag      120
acctggatcg gtctgaccct ggcgggaatg atcgtggcgg gatgggcggt tctgcatgtc      180
tacggcgtct attttcaccg atgggggccg ttgaccctgg tgatcgcccc ggcgatcgtg      240
gcggtccaga cctggttgtc ggtcggcctt ttcatcgtcg cccatgacgc catgcacggc      300
tccctggcgc cgggacggcc gcggctgaac gccgcagtcg gccggctgac cctggggctc      360
tatgcgggct ccgcttcga tcggctgaag acggcgcacc acgcccacca cgccgcgccc      420
ggcacggccg acgacccgga ttttcacgcc ccggcgcccc gcgccttcct tccctggttc      480
ctgaacttct ttcgcaccta tttcggctgg cgcgagatgg cggtcctgac cgccctggtc      540
ctgatcgccc tcttcggcct gggggcgcgg ccggccaatc tcctgacctt ctgggccgcg      600
ccggccctgc tttcagcgct tcagctcttc accttcggca cctggctgcc gcaccgccac      660
accgaccagc cgttcgccga cgcgcaccac gcccgcagca gcggctacgg ccccgtgctt      720
tccctgctca cctgtttcca cttcggccgc caccacgaac accatctgag cccctggcgg      780
ccctggtggc gtctgtggcg cggcgagtct tgagcccgcc ataaactgcc aggcatcaaa      840
ttaagcagaa ggccatcctg acggatggcc tttttgcgtt tctacaaact cttcctgtcg      900
tc                                                                    902

<210> SEQ ID NO 56
<211> LENGTH: 35
<212> TYPE: DNA
<213> ORGANISM: Artificial Sequence
<220> FEATURE:
<223> OTHER INFORMATION: primer
```

```
<400> SEQUENCE: 56
attcgagctc ggtactgaag cctgctttt tatac                              35

<210> SEQ ID NO 57
<211> LENGTH: 35
<212> TYPE: DNA
<213> ORGANISM: Artificial Sequence
<220> FEATURE:
<223> OTHER INFORMATION: primer

<400> SEQUENCE: 57
gcaggtcgac tctagctaga gcgggcgctg ccaga                             35

<210> SEQ ID NO 58
<211> LENGTH: 161
<212> TYPE: PRT
<213> ORGANISM: Brevundimonas sp.

<400> SEQUENCE: 58
```

Met Ala Trp Leu Thr Trp Ile Ala Leu Phe Leu Thr Ala Phe Leu Gly
1               5                   10                  15

Met Glu Ala Phe Ala Trp Ile Met His Arg Tyr Val Met His Gly Phe
            20                  25                  30

Leu Trp Ser Trp His Arg Ser His Glu Pro His Asp His Pro Leu
        35                  40                  45

Glu Lys Asn Asp Leu Phe Ala Val Val Phe Ala Ala Pro Ala Ile Val
    50                  55                  60

Met Val Ala Val Gly Leu His Leu Trp Pro Trp Ala Leu Pro Val Gly
65                  70                  75                  80

Leu Gly Ile Thr Ala Tyr Gly Met Val Tyr Phe Phe His Asp Gly
                85                  90                  95

Leu Val His Arg Arg Phe Pro Thr Gly Phe Ser Gly Arg Ser Gly Phe
            100                 105                 110

Trp Thr Arg Arg Ile Gln Ala His Arg Leu His His Ala Val Arg Thr
        115                 120                 125

Arg Glu Gly Cys Val Ser Phe Gly Phe Leu Trp Val Arg Ser Ala Arg
    130                 135                 140

Ala Leu Lys Ala Glu Leu Ala Gln Lys Arg Gly Ser Ser Ser Ser Gly
145                 150                 155                 160

Ala

```
<210> SEQ ID NO 59
<211> LENGTH: 162
<212> TYPE: PRT
<213> ORGANISM: Paracoccus sp.

<400> SEQUENCE: 59
```

Met Thr Asn Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Leu Val Phe Ala Val Ile Ala Thr Val Leu Phe
    50                  55                  60

Thr Val Gly Trp Ile Trp Ala Pro Val Leu Trp Trp Ile Ala Leu Gly
65                  70                  75                  80

```
Met Thr Val Tyr Gly Leu Ile Tyr Phe Val Leu His Asp Gly Leu Val
                    85                  90                  95

His Gln Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Met Ser Gly Val Leu Arg Ala Glu Ala Gln Glu
145                 150                 155                 160

Arg Thr

<210> SEQ ID NO 60
<211> LENGTH: 162
<212> TYPE: PRT
<213> ORGANISM: Alcaligenes sp.

<400> SEQUENCE: 60

Met Thr Gln Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Val Val Phe Ala Val Leu Ala Thr Ile Leu Phe
    50                  55                  60

Thr Val Gly Ala Tyr Trp Pro Val Leu Trp Ile Ala Leu Gly
65                  70                  75                  80

Met Thr Val Tyr Gly Leu Ile Tyr Phe Ile Leu His Asp Gly Leu Val
                    85                  90                  95

His Gln Arg Trp Pro Phe Arg Tyr Ile Pro Arg Arg Gly Tyr Phe Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Arg Ser Gly Val Leu Arg Pro Gln Asp Glu Arg
145                 150                 155                 160

Pro Ser

<210> SEQ ID NO 61
<211> LENGTH: 253
<212> TYPE: PRT
<213> ORGANISM: Nostoc punctiforme

<400> SEQUENCE: 61

Met Ile Gln Leu Glu Gln Pro Leu Ser His Gln Ala Lys Leu Thr Pro
1               5                   10                  15

Val Leu Arg Ser Lys Ser Gln Phe Lys Gly Leu Phe Ile Ala Ile Val
            20                  25                  30

Ile Val Ser Ala Trp Val Ile Ser Leu Ser Leu Leu Ser Leu Asp
        35                  40                  45

Ile Ser Lys Leu Lys Phe Trp Met Leu Leu Pro Val Ile Leu Trp Gln
    50                  55                  60

Thr Phe Leu Tyr Thr Gly Leu Phe Ile Thr Ser His Asp Ala Met His
65                  70                  75                  80
```

-continued

```
Gly Val Val Phe Pro Gln Asn Thr Lys Ile Asn His Leu Ile Gly Thr
                85                  90                  95
Leu Thr Leu Ser Leu Tyr Gly Leu Leu Pro Tyr Gln Lys Leu Leu Lys
                100                 105                 110
Lys His Trp Leu His His His Asn Pro Ala Ser Ser Ile Asp Pro Asp
            115                 120                 125
Phe His Asn Gly Lys His Gln Ser Phe Phe Ala Trp Tyr Phe His Phe
        130                 135                 140
Met Lys Gly Tyr Trp Ser Trp Gly Gln Ile Ile Ala Leu Thr Ile Ile
145                 150                 155                 160
Tyr Asn Phe Ala Lys Tyr Ile Leu His Ile Pro Ser Asp Asn Leu Thr
                165                 170                 175
Tyr Phe Trp Val Leu Pro Ser Leu Leu Ser Ser Leu Gln Leu Phe Tyr
                180                 185                 190
Phe Gly Thr Phe Leu Pro His Ser Glu Pro Ile Gly Gly Tyr Val Gln
            195                 200                 205
Pro His Cys Ala Gln Thr Ile Ser Arg Pro Ile Trp Trp Ser Phe Ile
        210                 215                 220
Thr Cys Tyr His Phe Gly Tyr His Glu Glu His His Glu Tyr Pro His
225                 230                 235                 240
Ile Ser Trp Trp Gln Leu Pro Glu Ile Tyr Lys Ala Lys
                245                 250
```